(12) United States Patent
Cobbold et al.

(10) Patent No.: US 10,441,649 B2
(45) Date of Patent: Oct. 15, 2019

(54) TARGETING MOIETY PEPTIDE EPITOPE COMPLEXES HAVING A PLURALITY OF T-CELL EPITOPES

(71) Applicant: The University of Birmingham, Birmingham (GB)

(72) Inventors: Mark Cobbold, Winchester, MA (US); David Millar, Winchester, MA (US)

(73) Assignee: The University of Birmingham, Birmingham (GB)

( * ) Notice: Subject to any disclaimer, the term of this patent is extended or adjusted under 35 U.S.C. 154(b) by 0 days.

(21) Appl. No.: 15/012,115

(22) Filed: Feb. 1, 2016

(65) Prior Publication Data
US 2016/0220665 A1 Aug. 4, 2016

Related U.S. Application Data

(60) Provisional application No. 62/111,069, filed on Feb. 2, 2015.

(51) Int. Cl.
| | |
|---|---|
| A61K 47/68 | (2017.01) |
| C07K 16/30 | (2006.01) |
| A61K 39/12 | (2006.01) |
| A61K 39/245 | (2006.01) |
| A61K 47/64 | (2017.01) |
| A61K 39/00 | (2006.01) |

(52) U.S. Cl.
CPC .......... *A61K 39/245* (2013.01); *A61K 47/646* (2017.08); *A61K 47/6811* (2017.08); *A61K 47/6849* (2017.08); *A61K 47/6881* (2017.08); A61K 2039/585 (2013.01); A61K 2039/6056 (2013.01); C12N 2710/16134 (2013.01)

(58) Field of Classification Search
CPC ............ A61K 47/6881; A61K 47/6889; A61K 47/6851; A61K 47/6855; A61K 47/6811; A61K 47/646; A61K 2039/585; A61K 2319/24; A61K 2319/50; A61K 2317/24; A61K 38/08; A61K 38/162; A61K 39/12; A61K 39/39558; A61K 39/145; A61K 39/29; A61K 39/165; A61K 39/20; C07K 16/30; C07K 16/3007; C07K 14/005
See application file for complete search history.

(56) References Cited

U.S. PATENT DOCUMENTS

| | | | |
|---|---|---|---|
| 5,229,490 A * | 7/1993 | Tam ..................... | C07K 14/001 424/185.1 |
| 5,583,202 A | 12/1996 | Zanetti | |
| 5,585,089 A | 12/1996 | Queen et al. | |
| 5,658,762 A | 8/1997 | Zanetti et al. | |
| 5,693,762 A | 12/1997 | Queen et al. | |
| 5,698,679 A | 12/1997 | Nemazee | |
| 5,739,116 A | 4/1998 | Hamann et al. | |
| 5,767,285 A | 6/1998 | Hamann et al. | |
| 5,773,001 A | 6/1998 | Hamann et al. | |
| 5,877,293 A | 3/1999 | Adair et al. | |
| 5,969,109 A | 10/1999 | Bona et al. | |
| 6,737,057 B1 | 5/2004 | Zaghouani | |
| 7,151,164 B2 | 12/2006 | Hansen et al. | |
| 7,247,303 B2 * | 7/2007 | Thorpe ................ | A61K 39/395 424/141.1 |
| 7,482,435 B2 | 1/2009 | Bowdish et al. | |
| 7,524,503 B2 * | 4/2009 | Khanna ................ | C07K 14/005 424/186.1 |
| 7,659,241 B2 | 2/2010 | Senter et al. | |
| 7,884,184 B2 | 2/2011 | De Groot et al. | |
| 8,187,600 B2 | 5/2012 | Durrant et al. | |
| 8,372,640 B2 | 2/2013 | Zanetti | |
| 8,742,088 B2 | 6/2014 | Durrant et al. | |
| 8,771,932 B2 | 7/2014 | Bowdish et al. | |
| 8,809,290 B2 | 8/2014 | Bot et al. | |
| 2002/0038002 A1 | 3/2002 | Zaghouani | |
| 2002/0081298 A1 | 6/2002 | Zaghouani | |
| 2004/0001853 A1 | 1/2004 | George et al. | |
| 2005/0037001 A1 | 2/2005 | Germeraad et al. | |
| 2005/0048550 A1 | 3/2005 | Storkus et al. | |

(Continued)

FOREIGN PATENT DOCUMENTS

| | | |
|---|---|---|
| EP | 460076 B1 | 12/1991 |
| EP | 0659438 A1 | 6/1995 |
| EP | 1292621 B1 | 9/2006 |
| EP | 1948802 A1 | 7/2008 |
| EP | 2134357 A2 | 12/2009 |
| EP | 1539819 B1 | 3/2010 |
| EP | 2193803 B1 | 10/2011 |
| EP | 1642910 B1 | 2/2012 |
| EP | 1664270 B1 | 5/2014 |
| GB | 1216649 | 3/2014 |

(Continued)

OTHER PUBLICATIONS

Joshi et al., Infection and immunity 69(8): 2001.*

(Continued)

*Primary Examiner* — Phuong Huynh
(74) *Attorney, Agent, or Firm* — McNeill Baur PLLC

(57) ABSTRACT

A variety of targeting moiety peptide epitope complexes (TPECs) are described in different embodiments. In each of the embodiments, however, a targeting moiety may be used to deliver the TPEC to an area of unwanted cells, allowing for a therapeutic effect to be delivered locally. The TPEC also contains a plurality of T-cell epitopes. The TPEC further comprises cleavage sites that release the T-cell epitopes from the targeting agent, and in some embodiments from each other, when they are in the microenvironment of the unwanted cells. Although the arrangement and number of T-cell epitopes varies in different embodiments described herein, once cleaved from the targeting agent (and any neighboring T-cell epitopes), the T-cell epitopes function by stimulating an immune response against the unwanted cells.

Figure 2C:
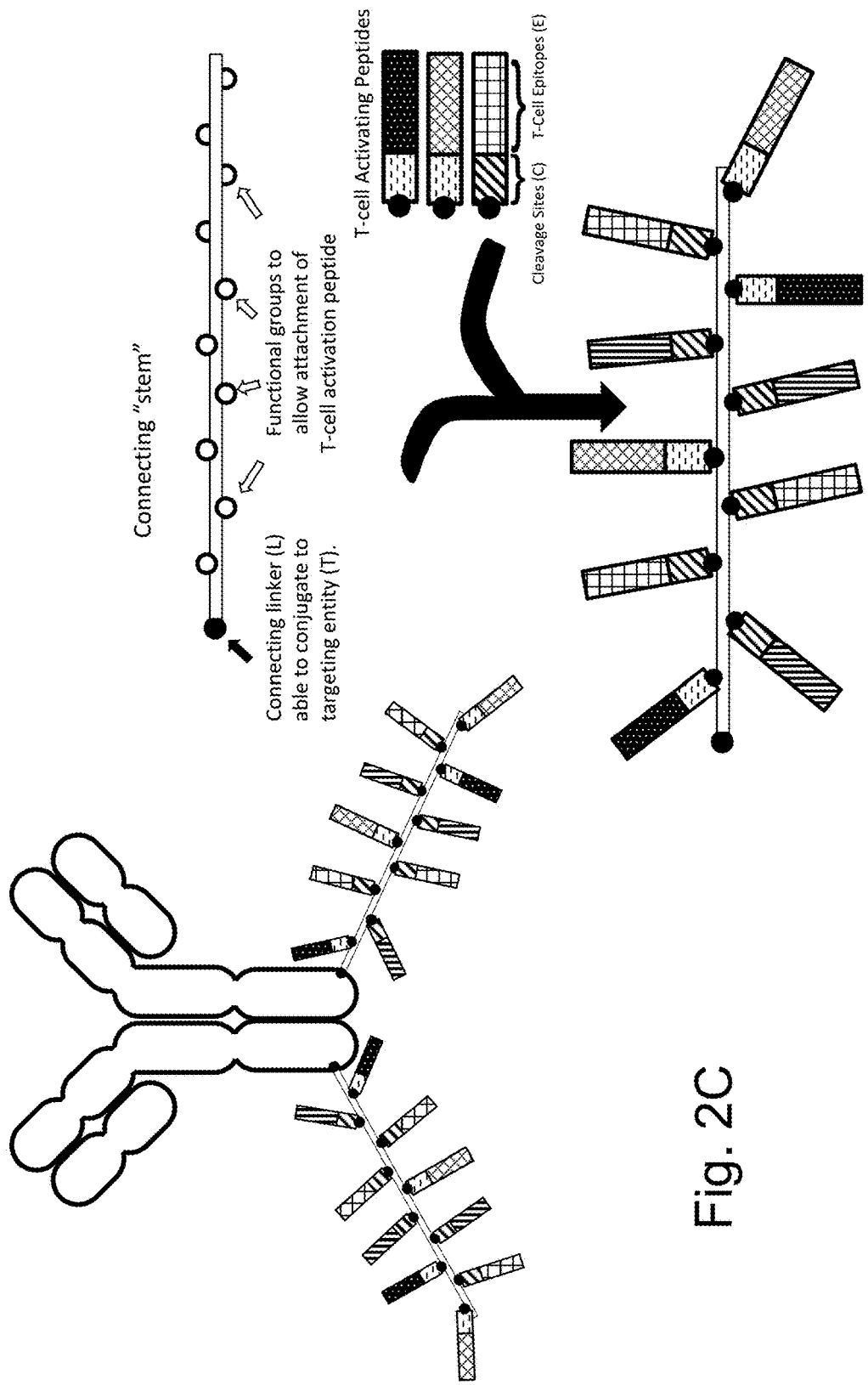

16 Claims, 12 Drawing Sheets
Specification includes a Sequence Listing.

(56) References Cited

U.S. PATENT DOCUMENTS

| | | |
|---|---|---|
| 2006/0034864 A1 | 2/2006 | Zaghouani |
| 2006/0045881 A1 | 3/2006 | Molldrem |
| 2006/0088522 A1 | 4/2006 | Boghaert et al. |
| 2006/0193855 A1 | 8/2006 | Bot et al. |
| 2006/0286604 A1* | 12/2006 | Mullins ................ A61K 38/168 435/7.1 |
| 2007/0122409 A1 | 5/2007 | Zaghouani |
| 2007/0218053 A1 | 9/2007 | Zaghouani |
| 2008/0069816 A1 | 3/2008 | Yazaki et al. |
| 2009/0181011 A1 | 7/2009 | Zaghouani |
| 2009/0214543 A1 | 8/2009 | Zangemeister-Wittke et al. |
| 2009/0280132 A1 | 11/2009 | Zaghouani |
| 2010/0291082 A1 | 11/2010 | Zurawski et al. |
| 2011/0008840 A1 | 1/2011 | Hoffee et al. |
| 2011/0110965 A1* | 5/2011 | Fraser .................... A61K 47/64 424/185.1 |
| 2013/0011424 A1* | 1/2013 | Maksyutov ........ A61K 39/0011 424/185.1 |
| 2013/0183347 A1 | 7/2013 | Zanetti |
| 2014/0271618 A1 | 9/2014 | Markel et al. |

FOREIGN PATENT DOCUMENTS

| | | | |
|---|---|---|---|
| WO | | 1991014438 A1 | 10/1991 |
| WO | | 1995017212 A1 | 6/1995 |
| WO | | 1996034892 A1 | 11/1996 |
| WO | | 1997023237 A1 | 7/1997 |
| WO | | 1998010651 A1 | 3/1998 |
| WO | | 1998018493 A2 | 5/1998 |
| WO | | 1998024478 A2 | 6/1998 |
| WO | | 1998041641 A1 | 9/1998 |
| WO | | 1999002175 A1 | 1/1999 |
| WO | | 00006605 | 2/2000 |
| WO | | 0244197 | 6/2002 |
| WO | | 2003027135 A2 | 4/2003 |
| WO | | 2004032962 A1 | 4/2004 |
| WO | | 2004069876 A2 | 8/2004 |
| WO | | 2005052004 A2 | 6/2005 |
| WO | | 2005061547 A2 | 7/2005 |
| WO | | 2005082003 A2 | 9/2005 |
| WO | | 2005082004 A2 | 9/2005 |
| WO | | 2005083431 A2 | 9/2005 |
| WO | | 2005087813 A1 | 9/2005 |
| WO | | 2007022477 A2 | 2/2007 |
| WO | | 2007057922 A1 | 5/2007 |
| WO | | 2007107764 A1 | 9/2007 |
| WO | | 2008019366 A2 | 2/2008 |
| WO | | 2008052322 A1 | 5/2008 |
| WO | | 2008097866 A2 | 8/2008 |
| WO | | 2009024771 A2 | 2/2009 |
| WO | | 2009025846 A2 | 2/2009 |
| WO | | 2008063113 | 7/2009 |
| WO | WO 2009/102421 | * | 8/2009 |
| WO | | 2010037837 A2 | 4/2010 |
| WO | | 2010081173 A2 | 7/2010 |
| WO | | 2011056721 A2 | 5/2011 |
| WO | | 2011110953 A2 | 9/2011 |
| WO | | 2012123755 A1 | 9/2012 |
| WO | WO2012123755 | * | 9/2012 |
| WO | | 2013082366 A1 | 6/2013 |
| WO | | 2013128194 A1 | 9/2013 |
| WO | | 2013139789 A1 | 9/2013 |
| WO | | 2014043523 A1 | 3/2014 |

OTHER PUBLICATIONS

Kowalczyk et al., Bioconjugate Chem 21: 102-110, 2010.*
Koide et al., J Mol Biol 284: 1141-1151, 1998.*
Bloom et al., Drug Discovery Today 14(19): 949-955, 2009.*
Yu et al., Investigative Ophthalmology & Visual Science 49(2): 522-527, Feb. 2008.*
Cochran et al., J. Immunol. Meth. 287: 147-158, 2004.*
Goel et al., J Immunology 173(12): 7358-7367, Dec. 15, 2004.*
Adis R&D Profile: Brentuximab Vedotin, Drugs RD 11(1):85-95 (2011).
Adler et al., Therapeutic Antibodies Against Cancer, Hematol Oncol Clin North Am. 26(3):447-481 (2012).
Akiyama et al., "Characterization of cytomegalovirus pp65-HLA-A24 peptide-specific CTL lines from metastatic melanoma patients", Oncology Reports 22: pp. 185-191 (Mar. 3, 2009).
Alderson RF, et al. CAT-8015: a second-generation pseudomonas exotoxin A-based immunotherapy targeting CD22-expressing hematologic malignancies. Clin Cancer Res. 15(3):832-9. Feb 1, 2009.
Alegretti AP, et al. Expression of CD55 and CD59 on peripheral blood cells from systemic lupus erythematosus (SLE) patients. Cell Immunol. 265(2):127-32. 2010; Epub Aug. 2, 2010.
Alexander, J., et al., "Linear PADRE T Helper Epitope and Carbohydrate B Cell Epitope Conjugates Induce Specific High Titer IgG Antibody Responses," J. Immunol. 164:1625-1633 (2000).
Alisa A, et al. "Human CD4(+) T cells recognize an epitope within alpha-fetoprotein sequence and develop into TGF-beta-producing CD4(+) T cells," J Immunol. Apr. 1, 2008;180(7):5109-17.
Andersen, M. H. et al. "Cytotoxic T Cells" Journal of Investigative Dermatology 126: 32-41 (2006).
Appay V. The physiological role of cytotoxic CD4(+) T-cells: the holy grail? Clin Exp Immunol. 138(1):10-13. 2004.
Arai K, et al., "Preventing effect of anti-ICAM-1 and anti-LFA-1 monoclonal antibodies on murine islet allograft rejection," International Journal of Pancreatology, Aug. 1999, vol. 26, Issue 1, pp. 23-31.
Ariel O, et al. Signal transduction by CD58: the transmembrane isoform transmits signals outside lipid rafts independently of the GPI-anchored isoform. Cell Signal. 21(7):1100-8. Jul. 2009. Epub Mar. 5, 2009.
Baeuerle P.A., et al. "BiTE: Teaching antibodies to engage T-cells for cancer therapy." Curr Opin Mol Therapeutics. 11(1):22-30. (Feb 1, 2009).
Baeuerle, P.A. and Reinhardt, C., "Bispecific T-Cell Engaging Antibodies for Cancer Therapy," Cancer Res. 69 ( 12):4941-4944 (2009).
Bargou, R., et al., "Tumor Regression in Cancer Patients by Very Low Doses of a T-Cell Engaging Antibody," Science 321:974-977 (2008).
Becker-Herman S, et al. CD74 is a member of the regulated intramembrane proteolysis-processed protein family. Mol Biol Cell. 16(11):5061-9. Nov. 2005. Epub Aug 17, 2005.
Bellosillo, B., et al., "Complement-Mediated Cell Death Induced by Rituximab in B-Cell Lymphoproliferative Disorders Is Mediated in vitro by a Caspase-Independent Mechanism Involving the Generation of Reactive Oxygen Species," Blood 98(9)2771-2777 (2001).
Bertilaccio, M.T.S., et al., "A Novel Rag2-Gamma2-Xenograft Model of Human CLL," Blood 115(8):1605-1609 (2010).
Bonnet, D. and Dick, J.E., "Human Acute Myeloid Leukemia is Organized as a Hierarchy that Originates from a Primitive Hematopoietic Cell," Nat Med. 3(7):730-737 (1997).
Borche L, et al. CD43 monoclonal antibodies recognize the large sialoglycoprotein of human leukocytes. Eur J Immunol. 17(10):1523-6. Oct. 1987.
Brodsky FM. A matrix approach to human class II histocompatibility antigens: reactions of four monoclonal antibodies with the products of nine haplotypes. Immunogenetics. 19(3)179-94. 1984.
Bruhl, H., et al., "Depletion of CCR5-Expressing Cells with Bispecific Antibodies and Chemokine Toxins: A New Strategy in the Treatment of Chronic Inflammatory Diseases and HIV," The Journal of Immunology, vol. 166, pp. 2420-2426 (2001).
Carter, P.J., "Introduction to Current and Future Protein Therapeutics: A Protein Engineering Perspective," Exp. Cell Res. 317:1261-1269 (2011).
Carter, P.J., "Potent Antibody Therapeutics by Design," Nat. Rev. Immunol 6:343-357 (2006).
Chinese Office Action in corresponding CN application No. 201280024084.1, dated Jul. 21, 2015.
Clark, E.A., et al., "Role ofBp35 Cell Surface Polypeptide in Human B-Cell Activation," Proc. Natl. Acad. Sci. 82: 1766-1770 (1985).

(56) References Cited

OTHER PUBLICATIONS

Clarke, et al., "Gemtuzumab Ozogamicin: Is There Room for Salvage?" Blood 116(14):2618-2619 (2010).
Cochran, Domain-level antibody epitope mapping through yeast surface display of epidermal growth factor receptor fragments, J of Immunological Methods 287:147-158 (2004).
De Groot, A.S., et al., "Activation of Natural Regulatory T Cells by IgG Fe-derived Peptide 'Tregitopes'," Blood 112(8):3303-3311 (2008).
Deckert M, et al. CD59 molecule: a second ligand for CD2 in T cell adhesion. Eur J Immunol. 22(11):2943-7. Nov. 1992.
Dermer, Another anniversary for the war on cancer, Bio/technology 12:320 (1994).
Donda, A., et al., "In vivo Targeting of an Anti-Tumor Antibody Coupled to Antigenic MHC Class I Complexes Induces Specific Growth Inhibition and Regression of Established Syngeneic Tumor Grafts," Cancer Immunity 3:11 (2003).
Duncan RJS et al., "A new reagent which may be used to introduce sulfhydryl groups into proteins, and its use in the preparation of conjugates for immunoassay," Analytical Biochemistry, 132(1):68-73 (Jul. 1, 1983).
Eberl, G., et al., "An Anti-CD19 Antibody Coupled to a Tetanus Toxin Peptide Induces Efficient Fas Ligand (FasL)-Mediated Cytotoxicity of a Transformed Human B Cell Line by Specific CD4+ T Cells," Clinical and Experimental Immunology 114:173-178 (1998).
Engleman EG, et al. Studies of a human T lymphocyte antigen recognized by a monoclonal antibody. Proc Natl Acad Sci U S A. 78(3):1791-5. Mar. 1981.
Eno-Amooquaye, E.A., et al., "Altered Biodistribution of an Antibody-Enzyme Conjugate Modified with Polyethylene Glycol," Br. J. Cancer 73:1323-1327 (1996).
Epstein AL, et al. Two new monoclonal antibodies (LN-1, LN-2) reactive in B5 formalin-fixed, paraffin-embedded tissues with follicular center and mantle zone human B lymphocytes and derived tumors. J Immunol. 133(2):1028-1036. Aug. 1984.
European Office Action in corresponding EP Application No. 12718715.1, dated Jul. 23, 2015.
Fattah, O.M., et al., "Peptabody-EGF: A Novel Apoptosis Inducer Targeting ErbB 1 Receptor Overexpressing Cancer Cells," Int. J. Cancer 119:2455-2463 (2006).
First Office Action and Search Report from the State Intellectual Property Office of the People's Republic of China for Application No. 201280024084.1, dated Nov. 15, 2014 (18 pages).
Fluhr H, et al. Interferon-gamma and tumor necrosis factor-alpha sensitize primarily resistant human endometrial stromal cells to Fas-mediated apoptosis. J Cell Sci. 120(Pt 23):4126-33. Dec. 1, 2007; Epub Nov. 14, 2007.
Germain, C., et al., "MHC Class I-Related Chain A Conjugated to Antitumor Antibodies can Sensitize Tumor Cells to Specific Lysis by Natural Killer Cells," Clin. Cancer Res. 11(20):7516-7522 (2005).
Ghanekar et al., Gamma Interferon Expression in CD8+ T Cells is a Marker for Circulating Cytotoxic T Lymphocytes that Recognize an HLA A2-Restricted Epitope of Human Cytomegalovirus Phosphoprotein p65, Clin Diagn Lab Immunol 8(3):628-31 (2001).
Giovannoni, L., et al., "Isolation of Anti-angiogenesis Antibodies from a Large Combinatorial Repertoire by Colony Filter Screening," Nucleic Acids Research 29(5):E27 (2001).
Golay, Mechanisms of action of therapeutic monoclonal antibodies: promises and pitfalls of in vitro and in vivo assays, Archives of Biochemistry and Biophysics 526:146-153 (2012).
Grimbert P. Thrombospondin/CD47 interaction: a pathway to generate regulatory T cells from human CD4+ CD25− T cells in response to inflammation. J Immunol. 177(6):3534-41. Sep. 15, 2006.
Gura, Systems for identifying new drugs are often faulty, Science 278:1041-1042 (1997).
Hellstrom, I., et al., "Monoclonal Mouse Antibodies Raised Against Human Lung Carcinoma," Cancer Research 46:3917-3923 (1986).
Hislop, A.D., et al., "Cellular Responses to Viral Infection in Humans: Lessons from Epstein-Barr Virus," Annu. Rev. Immunol. 25:587-617 (2007).
Horie R, Watanabe T. CD30: expression and function in health and disease. Semin Immunol. 10(6):457-70. Dec. 1998.
Howland, S.W., et al., "Inducing Efficient Cross-Priming Using Antigen-Coated Yeast Particles," J. Immunother. 31(7):607-619 (2008).
International Search Report and Written Opinion issued in corresponding PCT Application No. PCT/US2016/015983, dated Jun. 2, 2016.
Ishioka et al., "Utilization of MHC Class I Transgenic Mice for Development of Minigene DNA Vaccines Encoding Multiple HLA-Restricted CTL Epitopes," J. Immunol. 1999; 162:3915-3925, http://www.jimmunol.org/content/162/7/3915.
Millar, David G. et al., "Engineered release and presentation of antibody-bound viral antigens: A highly specific and novel immunotherapeutic approach to target cancer in vivo," Cancer Research, American Assoc. for Cancer Research, U.S., vol. 74, No. 19, supp. S, Oct. 1, 2014, pp. 1-3.
Morton, L.T. et al., "Redirection of CMV-specific CD8 T-cell immunity in chronic lymphocytic leukaemia by manipulating the antigen expression profile," Immunology, Wiley-Blackwell Publishing Ltd., GB, vol. 143, No. Supp. 2, Dec. 1, 2014, p. 146.
Pishraft Sabet et al., "Immunogenicity of Multi-Epitope DNA and Peptide Vaccine Candidates Based on Core, E2, NS3 and NS5B HCV Epitopes in BALB/c Mice," Hepat Mon. Oct. 2014, 14(10): e22215, pp. 1-9.
Suhrbier, A., "Multi-epitope DNA vaccines," Immunology and Cell Biology (1997) 75, pp. 402-408.
R.L. Metheringham, et al. mAbs 1(1):71-85 (2009).
O'Sullivan, M.J., et al., "Comparison of Two Methods of Preparing Enzyme-Antibody Conjugates: Application of these Conjugates for Enzyme Immunoassay," Analytical Biochemistry 100: 100-108(1979).
Park, B.-W., et al., "Rationally Designed Anti-HER2/neu Peptide Mimetic Disables P185HER2/neu Tyrosine Kinases in vitro and in vivo," Nature Biotechnology 18: 194-198 (2000).
Plant, A, et al., "Phospholipid/Alkanethiol Bilayers For Cell-Surface Receptor Studies by Surface Plasmon Resonance," Analytical Biochemistry, vol. 226, pp. 342-348 (1995).
Polski JM and Janney CG. Ber-H2 (CD30) immunohistochemical staining in malignant melanoma. Mod Pathol. 12(9):903-6. Sep. 1999.
Ponde, D.E., et al., "Development of Anti-EGF Receptor Peptidomimetics (AERP) as Tumor Imaging Agent," Bioorganic & Medicinal Chemistry Letters 21:2550-2553 (2011).
Poon, Ka, "Safety Assessment of Antibody Drug Conjugates," Presentation at Northern California Society of Toxicology. May 6, 2010.
Porcelli, S., et al., "Recognition of Cluster of Differentiation 1 Antigens by Human CD4-CD8-Cytolytic T Lymphocytes," Nature 341:447-450 (1989).
Rader, C., "DARTs Take Aim at BiTEs," Blood 117:4403-4404 (2011).
Rajasagi M. CD44 promotes progenitor homing into the thymus and T cell maturation. J Leukoc Biol. 85(2):251-61. Feb. 2009; Epub Oct. 27, 2008.
Rawlings, N. D., et al., "MEROPS: The Peptidase Database," Nucleic Acids Research 36:D320-D325 (2008).
Response to Office Action from European Patent Office dated Nov. 8, 2013, filed Apr. 14, 2014, for European Patent Application No. 12718715.1 (21 pages).
Rich, D.H., "Inhibitors of cysteine proteases." In Research monographs in cell and tissue physiology vol. 12, Proteinase inhibitors. Barrett AJ, Salvesen G, eds. (Amsterdam: Elsevier.) pp. 153-178 (1986).
Romagnoli, P., et al., "Selective Interaction of Ni with an MHC-Bound Peptide," The EMBO Journal 10(6):1303-1306 (1991).
Romero, P., et al., "Photoaffinity Labeling of the T Cell Receptor on Living Cytotoxic T Lymphocytes," The Journal of Immunology 150(9):3825-3831 (1993).

(56) References Cited

OTHER PUBLICATIONS

Sathish, Challenges and approaches for the development of safer immunomodulatory biologics, Nature Reviews Drug Discovery 12:306-324 (2013).
Savage, P., et al., "Induction of Viral and Tumour Specific CTL Responses Using Antibody Targeted HLA Class I Peptide Complexes," British Journal of Cancer 86:1336-1342 (2002).
Schaffitzel, C., et al., "Ribosome Display: an in vitro Method for Selection and Evolution of Antibodies from Libraries," Journal of Immunological Methods 231 :119-135 (1999).
Schmiegel, W., et al., "Cytokine-Mediated Enhancement of Epidermal Growth Factor Receptor Expression Provides an Immunological Approach to the Therapy of Pancreatic Cancer," Proc. Natl. Acad. Sci. 94:12622-12626 (1997).
Search report from Intellectual Property Office for GB1216649 dated Jan. 17, 2013.
Searle, F., et al., "A Human Choriocarcinoma Xenograft in Nude Mice; a Model for the Study of Antibody Localization," British Journal Cancer 44: 13 7-144 (1981 ).
Senter, P.D., et al., "Anti-Tumor Effects of Antibody-Alkaline Phosphatase Conjugates in Combination with Etoposide Phosphate," Proc. Natl. Acad. Sci. 85:4842-4846 (1988).
Shen, L., et al., "Important Role of Cathepin S in Generating Peptides for TAP-Independent MHC Class I Crosspresentation In Vivo," Immunity 21:155-165 (2004).
Sherman, D.B. and Spatola, A.F., "Compatibility of Thioamides with Reverse Turn Features: Synthesis and Conformational Analysis of Two Model Cyclic Pseudopeptides Containing Thioamides as Backbone Modifications," J. Am. Chem. Soc. 112:433-441 (1990).
Small, E.J., et al., "Placebo-Controlled Phase III Trial of Immunologic Therapy with Sipuleucel-T (APC8015) in Patients with Metastatic, Asymptomatic Hormone Refractory Prostate Cancer," Journal of Clinical Oncology 24(19):3089-3094 (2006).
Smith, D.C., et al., "Exogenous Peptides Delivered by Ricin Require Processing by Signal Peptidase for Transporter Associated with Antigen Processing-Independent MHC Class I restricted Presentation," J. Immunol. 169:99-107 (2002).
Staerz, U., et al., "Hybrid Antibodies Can Target Sites for Attack by T Cells," Nature, vol. 314, pp. 628-631 (Apr. 1985).
Staerz, U.D. and Bevan, M.J., "Hybrid Hybridoma Producing a Bispecific Monoclonal Antibody that can Focus Effector T-Cell Activity," Proc. Natl. Acad. Sci 83: 1453-1457 (1986).
Stein R, et al. Epitope specificity of the anti-(B cell lymphoma) monoclonal antibody, LL2. Cancer Immunol Immunother. 37(5):293-8. Oct. 1993.
Stirnemann, K., et al., "Sustained Activation and Tumor Targeting of NKT Cells Using a CDldanti-HER2-scFv Fusion Protein Induce Antitumor Effects in Mice," The Journal of Clinical Investigation 118(3 ):994-1005 (2008).
Sumida T, et al., "Regulatory T cell epitope recognized by T cells from labial salivary glands of patients with Sjögren's syndrome," Arthritis Rheum. Dec. 1997;40(12):2271-3.
Sykulev, Y., et al., "Evidence that a Single Peptide-MHC Complex on a Target Cell can Elicit a Cytolytic T Cell Response," Immunity 4:565-571 (1996).
Sylwester, A.W., et al., "Broadly Targeted Human Cytomegalovirus-Specific CD4+ and CD8+ T Cells Dominate the Memory Compartments of Exposed Subjects," The Journal of Experimental Medicine 202(5):673-685 (2005).
Tamiolakis D et al. Distribution of somatostatin in pancreatic ductal adenocarcinoma remodels the normal pattern of the protein during foetal pancreatic development: an immunohistochemical analysis. Clin Exp Med. 5(3):106-11. 2005.
Thorsett, E.D., et al., "Dipeptide Mimics. Conformationally Restricted Inhibitors of Angiotensin-Converting Enzyme," Biochemical and Biophysical Research Communications 111(1):166-171(1983).
Tosolini, M., et al., "Clinical Impact of Different Classes of Infiltrating T Cytotoxic and Helper Cells (ThI, Th2, Treg, ThI 7) in Patients with Colorectal Cancer," Cancer Res. 71 (4):1263-1271 (2011).
Trowbridge IS, et al. Biochemical characterization and cellular distribution of a polymorphic, murine cell-surface glycoprotein expressed on lymphoid tissues. Immunogenetics. 15(3):299-312. Mar. 1982.
Veber, D.F ., et al., "Conformationally Restricted Bicyclic Analogs of Somatostatin," Proc. Natl. Acad. Sci. 75 (6):2636-2640 (1978).
Vita, R., et al., "The Immune Epitope Database 2.0," Nucleic Acids Research 38:D854-D862 (2010).
Waldman, T.A., et al., "Immune Receptors: Targets for Therapy of Leukemia/Lymphoma, Autoimmune Diseases and for the Prevention of Allograft Rejection," Annu. Rev. Immunol. 10:675-704 (1992).
Wang, Q.-C., et al., "Induction of Hepatitis C Virus-Specific Cytotoxic T and B Cell Responses by Dendritic Cells Expressing a Modified Antigen Targeting Receptor," World Journal of Gastroenterology 11(4):557-560 (2005).
Webb S, et al., "Pharma interest surges in antibody drug conjugates," Nat Biotechnol. Apr. 2011;29(4):297-8.
Weiner, Monoclonal Antibodies for Cancer Immunotherapy, Lancet 373(9668):1033-1040 (2009).
Winter, G., et al., "Making Antibodies by Phage Display Technology," Annu. Rev. Immunol. 12:433-455 (1994).
Witte, Monoclonal antibodies targeting the VEGF receptor-2 (FIk1/KDR) as an anti-angiogenic therapeutic strategy, Cancer and Metastasis Reviews 17:155-151 (1998).
Written Opinion of the International Searching Authority for PCT/GB2013/050499 dated Jul. 24, 2013.
Yu, Interaction between Bevacizumab and Murine VEGF-A: A Reassessment, Investigative Ophthalmology & Visual Science 49(2):522 (2008).
Zhou, X., et al., "The Role of Complement in the Mechanism of Action of Rituximab for B-Cell Lymphoma: Implications for Therapy," The Oncologist 13:954-966 (2008).
Zinkernagel, R. M. et al. "Antigen localisation regulates immune responses in a dose- and time-dependent fashion: a geographical view of immune reactivity" Immunological Reviews 156: 199-209 (1997).
Hughes, B., "Antibody-Drug Conjugates for Cancer: Poised to Deliver?," Nature Reviews Drug Discovery 9:665-667 (2010).
International Preliminary Report on Patentability for International Application PCT/GB2012/050577; dated Sep. 17, 2013.
International Preliminary Report on Patentability for PCT/GB2013/050499 dated Sep. 2, 2014.
International Search Report and Written Opinion of the International Searching Authority for International Application No. PCT/GB2012/050577, "Re-Directed Immunotherapy," dated Jun. 29, 2012.
International Search Report for PCT/GB2013/050499 dated Jul. 24, 2013.
International Search Report for PCT/GB2013/052427 dated May 2, 2014.
Irvine, D.J., et al., "Direct Observation of Ligand Recognition by T Cells," Nature 419:845-849. (2002).
Jeffrey, S.C. et al. "Dipeptide-Based Highly Potent Doxorubicin Antibody Conjugates," Bioorganic & Medicinal Chemistry Letters 16:358-362 (2006).
Jilaveanu LB, et al. CD70 expression patterns in renal cell carcinoma. Hum Pathol. 43(9):1394-9. Sep. 2012; Epub Mar. 7, 2012.
Jubala, CD20 Expression in Normal Canine B Cells and in Canine non-Hodgkin Lymphoma, Vet Pathol 42:468-476 (2005).
Jutila MA, et al. L-selectin serves as an E-selectin ligand on cultured human T lymphoblasts. J Immunol. 169 (4):1768-73. Aug. 15, 2002.
Kang et al., Targeted Coating with Antigenic Peptide Renders Tumor Cells Susceptible to CD8+ T Cell-mediated Killing, Molecular Therapy 21(3):542-553 (2013).
Kawamura, K.S., et al., "In Vivo Generation of Cytotoxic T Cells from Epitopes Displayed on Peptide-Based Delivery Vehicles," Journal of Immunology 168:5709-5715 (2002).
Klechevsky E, et al. Cross-priming CD8+ T cells by targeting antigens to human dendritic cells through DCIR. Blood. 116(10):1685-97. Sep. 9, 2010; Epub Jun. 7, 2010.
Kohler, et al., "Continuous Cultures of Fused Cells Secreting Antibody of Predefined Specificity," Nature 256:495-497 (1975).

(56) References Cited

OTHER PUBLICATIONS

Kozak R.W., et al., "IL-2-PE40 Prevents the Development of Tumors in Mice Injected with IL-2 Receptor Expressing EL4 Transfectant Tumor Cells," Journal of Immunology 145 (8):2766-2771 (1990).
Kreitman RJ, et al. Phase I trial of anti-CD22 recombinant immunotoxin moxetumomab pasudotox (CAT-8015 or HA22) in patients with hairy cell leukemia. J Clin Oncol. 230(15):1822-8. May 20, 2012; Epub Feb. 21, 2012.
Kufer, P., et al., "Construction and Biological Activity of a Recombinant Bispecific Single-Chain Antibody Designed For Therapy of Minimal Residual Colorectal Cancer," Cancer Immunology Immunotherapy, vol. 45, pp. 193-197 (1997).
Lagadec P, et al. Involvement of a CD47-dependent pathway in platelet adhesion on inflamed vascular endothelium under flow. Blood. 101(12):4836-43. Jun. 15, 2003; Epub Feb. 27, 2003.
Lamb CA, et al. Invariant chain targets HLA class II molecules to acidic endosomes containing internalized influenza virus. Proc Natl Acad Sci U S A. 88(14):5998-6002. Jul. 15, 1991.
Larche, M., et al., "Functional Evidence for a Monoclonal Antibody that Binds to the Human IL-4 Receptor," Immunology 65:617-622 (1988).
Lash, A., "Making the Case for Antibody-Drug Conjugates," In Vivo: The Business and Medicine Report:32-38 (2010).
Lehmann JC, et al. Overlapping and selective roles of endothelial intercellular adhesion molecule-1 (ICAM-1) and ICAM-2 in lymphocyte trafficking. J Immunol. 171(5):2588-93. Sep. 1, 2003.
Lesley J, Trowbridge IS. Genetic characterization of a polymorphic murine cell-surface glycoprotein. Immunogenetics. 15(3):313-20. Mar. 1982.
Li S, et al., "Analysis of FOXP3+ regulatory T cells that display apparent viral antigen specificity during chronic hepatitis C virus infection," PLoS Pathog. Dec. 2009;5(12):e1000707. Epub Dec. 24, 2009.
Lim et al., Anti-CD20 monoclonal antibodies: historical and future perspectives, Hematologica 94(1):135-143 (2010).
Loffler et al. "A recombinant bispecific single-chain antibody, CD19 × CD3, induces rapid and high lymphoma-directed cytotoxicity by unstimulated T lymphocytes." 95(6): 2098-103. (Mar. 15, 2000).
Loisel, S., et al., "Establishment of a Novel Human B-CLL-like Xenograft Model in Nude Mouse," Leukemia Research 29:1347-1352 (2005).
Lorberboum-Galski, H., et al., "Cytotoxic Activity of an Interleukin 2-Pseudomonas Exotoxin Chimeric Protein Produced in *Escherichia coli*," Proc. Natl. Acad. Sci 85: 1922-1926 (1988).
Lutterbuese R. et al., "T cell-engaging BiTE antibodies specific for EGFR potently eliminate KRAS- and BRAF-mutated colorectal cancer cell", Proc. Natl. Acad. Sci. 107(28):12605-12610. (Jul. 13, 2010).
Lutterbuese, R., et al., "Potent Control of Tumor Growth by CENCD3-bispecific Single-Chain Antibody Constructs that are not Competitively Inhibited by Soluble CEA," J. Immunother. 32(4):341-352 (2009).
Mack, M., et al., "A Small Bispecific Antibody Construct Expressed as a Functional Single-Chain Molecule With High Tumor Cell Cytotoxicity," Proceedings of the National Academy of Sciences, vol. 93, pp. 7021-7025 (Jul. 1995).
Mack, M., et al., "Biologic Properties of a Bispecific Single-Chain Anitbody Directed Against 17-1A (EpCAM) and CD3; Tumor Cell-Dependent T Cell Stimulation and Cytotoxic Activity," The Journal of Immunology, vol. 158, pp. 3965-3971 (1997).
Mahato, R., et al., "Prodrugs for Improving Tumor Targetability and Efficiency," Adv. Drug. Deliv. Rev. 63(8):659-670 (2011).
Maiti A et al. TNF-alpha induction of CD44-mediated leukocyte adhesion by sulfation. Science. 282(5390):941-3. Oct. 30, 1998.
Matsumura, Y. and Maeda, H., "A New Concept for Macromolecular Therapeutics in Cancer Chemotherapy: Mechanism of Tumoritropic Accumulation of Proteins and the Antitumor Agent Smancs," Cancer Res. 46:6387-6392 (1986).

Mayes, S., et al., "New Antibody Drug Treatments for Lymphoma," Expert Opin. Biol. Ther. 11 ( 5):623-640 (2011 ).
Mazor R, et al. Identification and elimination of an immunodominant T-cell epitope in recombinant immunotoxins based on Pseudomonas exotoxin A. Proc Natl Acad Sci U S A. 109(51):E3597-603. Dec. 18, 2012. Epub Dec. 3, 2012.
Melton, R.G., et al., "Covalent Linkage of Carboxypeptidase G2 to Soluble Dextrams-1," Biochemical Pharmacology 36 (1):105-112 (1987).
Meziere, C., et al., "In Vivo T Helper Cell Response to Retro-Inverso Peptidomimetics," J. Immunol. 159:3230-323 7 (1997).
Molhoj et al. "CD19-/CD3-bispecific antibody of the BiTE class is far superior to tandem diabody with respect to redirected tumor cell lysis", Mol Immunol. 44(8):1935-1943. (Dec. 1, 2006).
Moore, P.A., et al., "Application of Dual Affinity Retargeting Molecules to Achieve Optimal Redirected T-Cell Killing of B-Cell Lymphoma," Blood 117(17):4542-4551 (2011).
Mous et al., "Redirection of CMV-specific CTL towards B-CLL via CD20-targeted HLA/CMV complexes," Leukemia 20, pp. 1096-1102 (2006).
Murphy, G., "The ADAMs: Signalling Scissors in the Tumour Microenvironment," Nature Reviews Cancer 8:929-941 (2008).
Non-Final Office Action in corresponding U.S. Appl. No. 14/005,452, dated Jul. 31, 2015.
Non-Final Office Action in corresponding U.S. Appl. No. 14/660,137, dated Oct. 22, 2015.
Ogg, G.S., et al., "Sensitization of Tumour Cells to Lysis by Virus-Specific CTL using Antibody-Targeted MHC Class I/Peptide Complexes," British Journal of Cancer 82( 5): 105 8-1062 (2000).
Onda M, et al. An immunotoxin with greatly reduced immunogenicity by identification and removal of B cell epitopes. Proc Natl Acad Sci U S A 2105(32):11311-6, Aug. 12, 2008; Epub Aug. 4, 2008.
Osborn L, et al. Amino acid residues required for binding of lymphocyte function-associated antigen 3 (CD58) to its counter-receptor CD2. J Exp Med. 181(1):429-34. Jan. 1995.
Markovic et al., "Current role of EGF receptor monoclonal antibodies and tyrosine kinase inhibitors in the management of head and neck squamous cell carcinoma," Expert Rev. Anticancer Ther. 12(9):1149-1149, Sep. 2012.
Blumenthal-RD et al. Expression patterns of CEACAM5 and CEACAM6 in primary and metastatic cancers. BMC cancer 7:2 (2007).
Japink D et al. CEA in activated macrophages. New diagnostic possibilities for tumor markers in early colorectal cancer. Anticancer Res 29(8):3245-51 (2009).
Kirshner J et al. CEACAM1, a cell-cell adhesion molecule, directly associates with annexin II in a three-dimensional model of mammary morphogenesis. Journal of Biological Chemistry 278(50):50338-50345 (2003).
Ma X et al. Flow injection chemiluminescent immunoassay for carcinoembryonic antigen using boronic immunoaffinity column. Sensors 9(12):10389-99 (2009).
Meyer T et al. A Phase I Trial of Radioimmunotherapy with 131I-A5B7 Anti-CEA Antibody in Combination with Combretastatin-A4-Phosphate in Advanced Gastrointestinal Carcinomas. Clin Cancer Res 15(13):4484-4492 (2009).
Schoffelen R et al. Pretargeted immuno-positron emission tomography imaging of carcinoembryonic antigen-expressing tumors with a bispecific antibody and a 68Ga- and 18F-labeled hapten peptide in mice with human tumor xenografts. Mol Cancer Ther 9(4):1019-27 (2010).
Shibata S et al. A phase I study of a combination of yttrium-90-labeled anti-carcinoembryonic antigen (CEA) antibody and gemcitabine in patients with CEA-producing advanced malignancies. Clin Cancer Res 15(8):2935-41 (2009).
Sienel W et al. Elevated Expression of Carcinoembryonic Antigen-related Cell Adhesion Molecule 1 Promotes Progression of Non-Small Cell Lung Cancer1Clinical Cancer Research. 9:2260-2266. (2003).
Skubitz KM and Skubitz AP Interdependency of CEACAM-1, -3, -6, and -8 induced human neutrophil adhesion to endothelial cells. J Transl Med. 6:78 (2008).

(56) References Cited

OTHER PUBLICATIONS

Urva SR and JP Balthasar. Target mediated disposition of T84.66, a monoclonal anti-CEA antibody: application in the letection of colorectal cancer xenografts. MAbs 22(1):67-72 (2010).
Yu Q et al. CEACAM1 (CD66a) promotes human monocyte survival via a phosphatidylinositol 3-kinase- and AKT-dependent pathway. Journal of Biological Chemistry. 281(51):39179-39193 (2006).
Pavoni et al., "Selection, affinity maturation, and characterization of a human scFv antibody against CEA protein," BMC Canter 20016, 6:41, pp. 1-15.

* cited by examiner

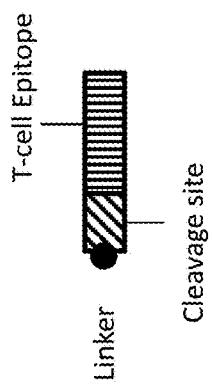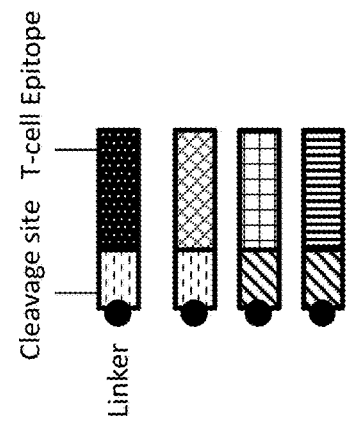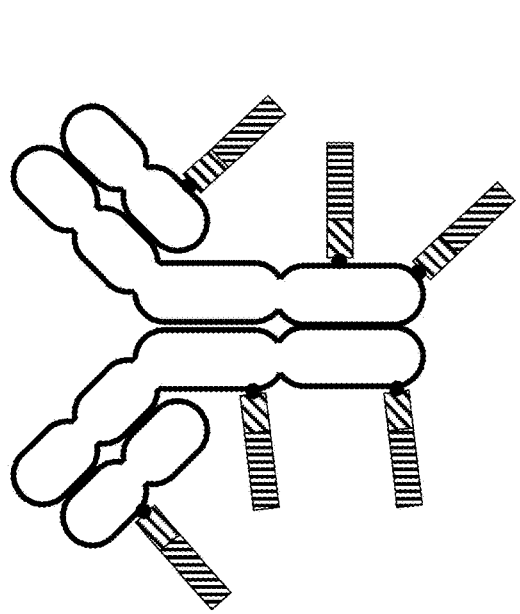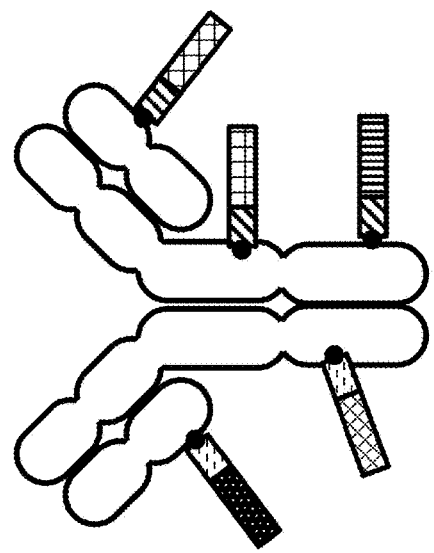
Fig. 1A
Fig. 1B

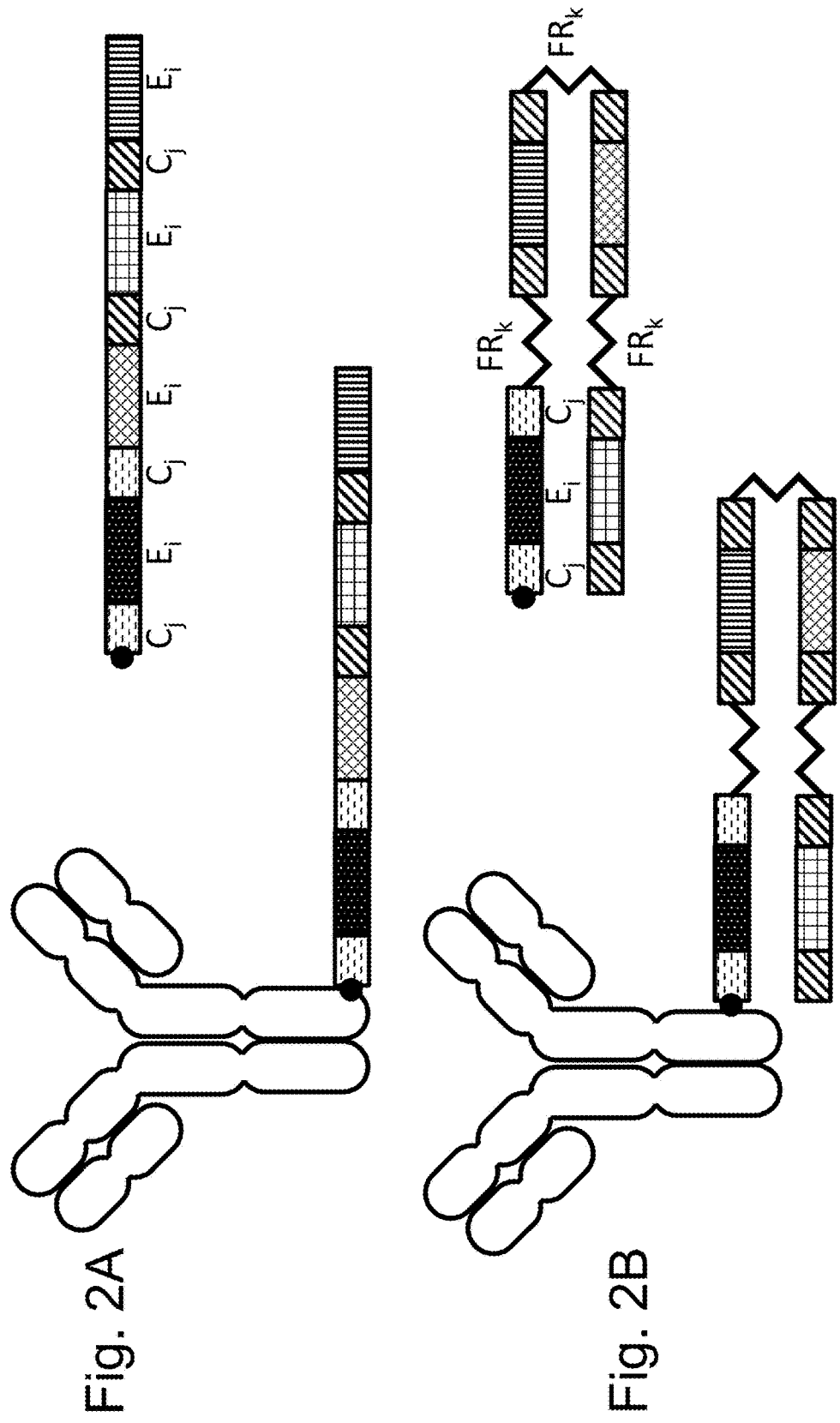

SASGGGGSGGGGSVSDVPRDLEVVAATPTSLLISWDAPAVGGGGSGGGGSTIPVSLRS*TPRVTGGGAM*TI
PVSLRSGGGGSGGGGSTVRYYRITYGETGGNSPVQEFTVPGSKSTATISGLKPGVDYTITVYAVTGGGGG
SGGGGSTIPVSLRS*NLVPMVATV*TIPVSLRSGGGGSGGGGSSPASSKPISINYRTGGGGSGGGGSTIPVS
LRS*VLEETSVML* (SEQ ID NO: 187)

TARGETING MOIETY PEPTIDE EPITOPE COMPLEXES HAVING A PLURALITY OF T-CELL EPITOPES

FIELD

This application relates to immuno therapeutic agents employing a plurality of T-cell epitopes. In particular, it relates to agents that can be used to treat a condition characterized by the presence of unwanted cells, such as cancer or other disease-causing cells.

BACKGROUND

Cancer and other diseases caused by the presence of unwanted cells create significant loss of life, suffering, and economic impact. Immunotherapeutic strategies for targeting cancer have been an active area of translational clinical research.

WO 2012/123755 discusses the concept of re-directed immunotherapy. In this application, an agent for preventing or treating a condition characterized by the presence of unwanted cells includes a targeting moiety that is capable of targeting to the unwanted cells and a T-cell epitope that can be released from the targeting moiety by selective cleavage of a cleavage site in the agent in the vicinity of the unwanted cells.

WO 2014/043523 teaches an agent based on an ScFV directed to cancer cells including from 1-10 immunogenic CD8 T-cell epitopes in one of the following two arrangements: T-c-En-c-Fcn or T-c-Fcn-c-En, where T is the ScFv, En is from 1-10 CD8 T-cell epitopes, c: is a protease cleavage site, and Fcn is from 1-10 Fc portions of an IgG antibody. In this reference, the 1-10 immunogenic CD8 T-cells are released from the ScFv and Fc portions of the agent in a single polypeptide chain, still conjugated to each other.

While some positive test data has been shown with prior approaches, clinically-effective therapeutic strategies must be able to elicit a strong immune response in an individual suffering from a disease such as cancer. Additionally, effective therapies should work well in a wide cross-section of patients from different racial and ethnic groups. Maximally-effective therapies would also generate an immune response against the unwanted cells without generating an inhibitory immune response against the therapeutic agent itself so that multiple rounds of treatment could be administered over a period of time. Therefore, additional developments in this field of re-directed immunotherapy are required.

SUMMARY

In accordance with the description, a variety of targeting moiety peptide epitope complexes (TPECs) are described in different embodiment of this application. In each of the embodiments, however, a targeting moiety may be used to deliver the TPEC to an area of unwanted cells, allowing for a therapeutic effect to be delivered locally. The TPEC also contains a plurality of T-cell epitopes. The TPEC further comprises cleavage sites that release the T-cell epitopes from the targeting agent, and in some embodiments from each other, when they are in the microenvironment of the unwanted cells. Although the arrangement and number of T-cell epitopes varies in different embodiments described herein, once cleaved from the targeting agent (and any neighboring T-cell epitopes), the T-cell epitopes function by stimulating an immune response against the unwanted cells.

In some embodiments, maximal benefits may be achieved by releasing all of the T-cell epitopes from both the targeting agent and from each other in the cleavage process, allowing each T-cell epitope the structural freedom to attract an immune response to the unwanted cell.

Having a plurality of T-cell epitopes, as discussed in detail below, enhances the immune response against the unwanted cells, either by stimulating a stronger immune response in a given patient or by allowing the TPEC to stimulate an immune response across a wide variety of patients in different ethnic and racial groups.

In one embodiment, a composition for retargeting an immune response to unwanted cells comprises a TPEC wherein:
a. T is a targeting moiety that is capable of targeting unwanted cells;
b. L is at least one linker capable of chemical linkage to T where L may be a peptide bond, at least one peptide, or a chemical linker;
c. C is at least one cleavage site
  i. cleaved by an enzyme expressed by the unwanted cells;
  ii. cleaved through a pH-sensitive cleavage reaction inside the unwanted cell;
  iii. cleaved by a complement-dependent cleavage reaction; or
  iv. cleaved by a protease that is colocalized to the unwanted cell by a targeting moiety that is the same or different from the targeting moiety in the TPEC; and
d. E is at least one T-cell epitope,
wherein the L, C, and E moieties are arranged in at least one of the following patterns:
  i. a plurality of L-C-E, each attached separately to T,
  ii. at least one of L-(C-E)n, with each C-E attached to the L in parallel, and/or
  iii. at least one of L-(C-E)n, with each C-E attached to the L in series.

In one embodiment, a composition for retargeting an immune response to unwanted cells comprises a TPEC having a plurality of T-cell epitopes separately conjugated to a targeting moiety comprising the formula $T\text{-}(L\text{-}C\text{-}E)_n$ or $T\text{-}(L\text{-}C_i\text{-}E_j)_n$, wherein:
a. T is a targeting moiety that is capable of targeting unwanted cells;
b. L is a linker capable of chemical linkage to T;
c. C is a cleavage site
  i. cleaved by an enzyme expressed by the unwanted cells;
  ii. cleaved through a pH-sensitive cleavage reaction inside the unwanted cell;
  iii. cleaved by a complement-dependent cleavage reaction; or
  iv. cleaved by a protease that is colocalized to the unwanted cell by a targeting moiety that is the same or different from the targeting moiety in the TPEC; and
b. E is a T-cell epitope
wherein n is an integer of at least 2 (optionally from about 2 to 50), i is an integer of at least 2 (optionally from about 1 to 50), and j is an integer of at least 2 (optionally from about 1 to 50). The "n" integer refers to the number of L-C-E moieties on the targeting moiety and the "i" and "j" integers refer to how many different types of cleavage sites and epitopes are within the construct.

In some embodiments, a composition for retargeting an immune response to unwanted cells comprises a TPEC with either a (i) linear and/or bundled polytope or a (ii) branched polytope. Such a TPEC may comprise the formula $T-L-(C_i-E_j)_n$, wherein:
a. T is a targeting moiety that is capable of targeting unwanted cells;
b. L is an optional linker capable of chemical or peptide linkage to T;
c. C is a cleavage site
   i. cleaved by an enzyme expressed by the unwanted cells;
   ii. cleaved through a pH-sensitive cleavage reaction inside the unwanted cell;
   iii. cleaved by a complement-dependent cleavage reaction; or
   iv. cleaved by a protease that is colocalized to the unwanted cell by a targeting moiety that is the same or different from the targeting moiety in the TPEC; and
d. E is a T-cell epitope;

wherein n is an integer of at least 2 (optionally from about 2 to 50), i is an integer of at least 2 (optionally from about 1 to 50), and j is an integer of at least 2 (optionally from about 1 to 50). The "n" integer refers to the number of C-E moieties on the targeting moiety and the "i" and "j" integers refer to how many different types of cleavage sites and epitopes are within the construct.

Further, in some embodiments, a composition for retargeting an immune response to unwanted cells comprises a TPEC having:
a. a targeting moiety that is capable of targeting unwanted cells;
b. a plurality of more than 10 T-cell epitopes conjugated to the targeting moiety with at least one cleavage site, wherein the cleavage site is
   i. cleaved by an enzyme expressed by the unwanted cells;
   ii. cleaved through a pH-sensitive cleavage reaction inside the unwanted cell;
   iii. cleaved by a complement-dependent cleavage reaction; or
   iv. cleaved by a protease that is colocalized to the unwanted cell by a targeting moiety that is the same or different from the targeting moiety in the TPEC.

Additional objects and advantages will be set forth in part in the description which follows, and in part will be obvious from the description, or may be learned by practice. The objects and advantages will be realized and attained by means of the elements and combinations particularly pointed out in the appended claims.

It is to be understood that both the foregoing general description and the following detailed description are exemplary and explanatory only and are not restrictive of the claims.

The accompanying drawings, which are incorporated in and constitute a part of this specification, illustrate one (several) embodiment(s) and together with the description, serve to explain the principles described herein.

BRIEF DESCRIPTION OF THE DRAWINGS

FIGS. 1A-B show certain embodiments of TPECs. In FIG. 1A, a targeting moiety, optionally an antibody, has a plurality of copies of the same T-cell epitope affixed to it using a chemical linker and a cleavage site. In FIG. 1B, a targeting moiety, optionally an antibody, has a plurality of different T-cell epitopes affixed to it using a chemical linker and a cleavage site. The linker-cleavage site-T-cell-epitopes may be affixed to the targeting moiety in random locations and in random amounts, creating a heterogeneous population of TPECs. In these embodiments, the TPEC comprises a plurality of L-C-E, each attached separately to T, where L is linker, C is cleavage site, E is epitope, and T is targeting moiety.

FIGS. 2A-C show certain embodiments of TPECs. In FIG. 2A, a targeting moiety, optionally an antibody, has a plurality of different T-cell epitopes affixed to it using a chemical or peptide linker, wherein the plurality of T-cell epitopes is separated by cleavage sites and affixed to the targeting moiety in a bundle. FIG. 2B shows the bundle of T-cell epitopes having immunoglobulin framework regions flanking certain domains. Both FIGS. 2A and 2B include polytopes with a linear configuration. In the embodiments of FIGS. 2A and 2B, the TPEC comprises at least one of L-(C-E)n, with each C-E attached to the L in series (in a bundled and/or linear configuration), and wherein n is an integer of at least 2 (optionally from about 2 to 50) and where L is linker, C is cleavage site, E is epitope, and T is targeting moiety. FIG. 2C shows one embodiment of a TPEC comprising a polytope with a branched configuration. In another embodiment, not shown, the polytope with a branched configuration may have identical T-cell epitopes. In the embodiments of FIG. 2C, the TPEC comprises at least one of L-(C-E)n, with each C-E attached to the L in parallel (in a branched configuration), and wherein n is an integer of at least 2 (optionally from about 2 to 50) and where L is linker, C is cleavage site, E is epitope, and T is targeting moiety.

FIGS. 3A-C show in vitro activity of re-directed virus specific T cells (Multiple Peptide TPEC approach). Recognition of a lymphoblastoid lymphoma cell line by CD8+ cytomegalovirus-specific cytotoxic T lymphocytes through conjugation of two different viral peptides, RPHERNGFTVL (SEQ ID NO: 2) and NLVPMVATV (SEQ ID NO: 1), to the anti-CD20 antibody Rituximab. Antibody is conjugated using sulfo-SMCC to peptides NLVPMVATVASGV{CIT}GC (SEQ ID NO: 3) and RPHERNGFTVLASGFKGC (SEQ ID NO: 4) at different ratios from 100% NLV:0% RPH through to 0% NLV:100% RPH. Target lymphoma cells labeled with TPEC are recognized by lymphocytes specific towards the NLV peptide (A) at all ratios down to 10% of the conjugated peptide being NLVPMVATVASGV{CIT}GC (SEQ ID NO: 3) Similarly, target lymphoma cells are recognized by lymphocytes specific towards the RPH peptide (B) at all ratios down to 10% of the conjugated peptide being the RPHERNGFTVLASGFKGC (SEQ ID NO: 4). In both (A) and (B), there is no T cell recognition by peptide-specific T cells when the ratio of the conjugated peptide recognized by the T cells is 0%. (C) Overlaid plots of (A) and (B) demonstrating activity of both NLV and RPH specific T cells using Rituximab TPECs conjugated with the two different peptides.

FIG. 4 illustrates recognition of a lymphoblastoid lymphoma cell line by CD8+ cytomegalovirus-specific cytotoxic T lymphocytes through conjugation of three different viral peptides, VLEETSVML (SEQ ID NO: 5), CRVLCCYVL (SEQ ID NO: 17) and YILEETSVM (SEQ ID NO: 7), to the anti-CD20 antibody Rituximab. Antibody is conjugated using sulfo-SMCC to equal amount of peptides VLEETSVMLASGFKGC (SEQ ID NO: 8), BRVLBBYVLASGFKGC (SEQ ID NO: 9) where B is amino butyric acid, a homolog for cysteine and YILEETSVMASGFKGC (SEQ ID NO: 10). Target lymphoma cells labeled with the TPEC are recognized by T cells specific for each of the three peptides conjugated to the antibody. Untreated target cells are not recognized by any of the peptide-specific T cells (negative control) and free peptide pulsed target cells are strongly recognized by T cells (positive control).

Figure 5:
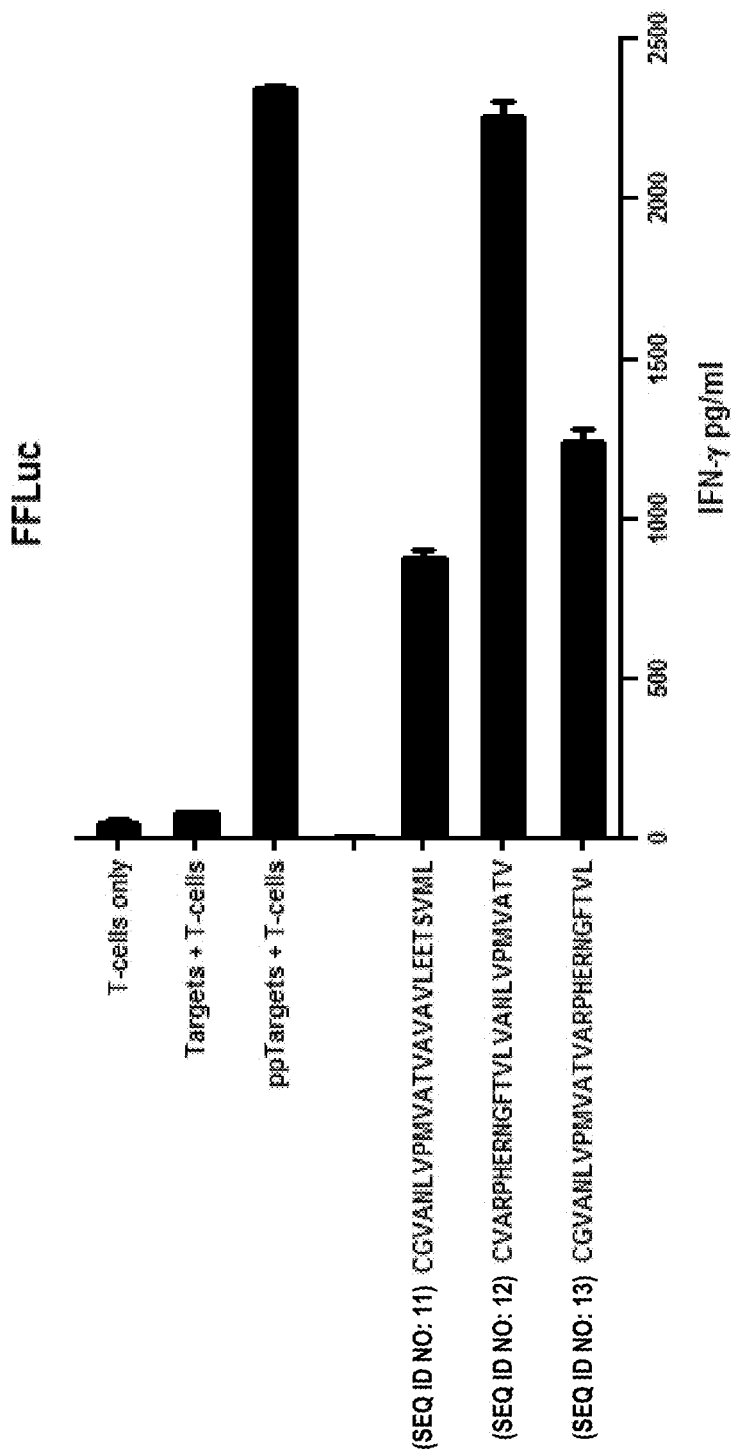

FIG. 5 demonstrates recognition of a lymphoblastoid lymphoma cell line by CD8+ cytomegalovirus-specific cytotoxic T lymphocytes through conjugation of polytope peptides. Antibody is conjugated using sulfo-SMCC to peptides (i) CGVANLVPMVATVAVAVLEETSVML (SEQ ID NO: 11), (ii) CVARPHERNGFTVLVANLVPMVATV (SEQ ID NO: 12) and (iii) CGVANLVPMVATVARPHERNGFTVL (SEQ ID NO: 13). Target lymphoma cells labeled with TPEC are recognized by T cells specific for the NLVPMVATV (SEQ ID NO: 1) peptide. Untreated target cells are not recognized by the peptide-specific T cells (negative control) and free peptide pulsed target cells are strongly recognized by T cells (positive control).

Figures 6A, 6B:
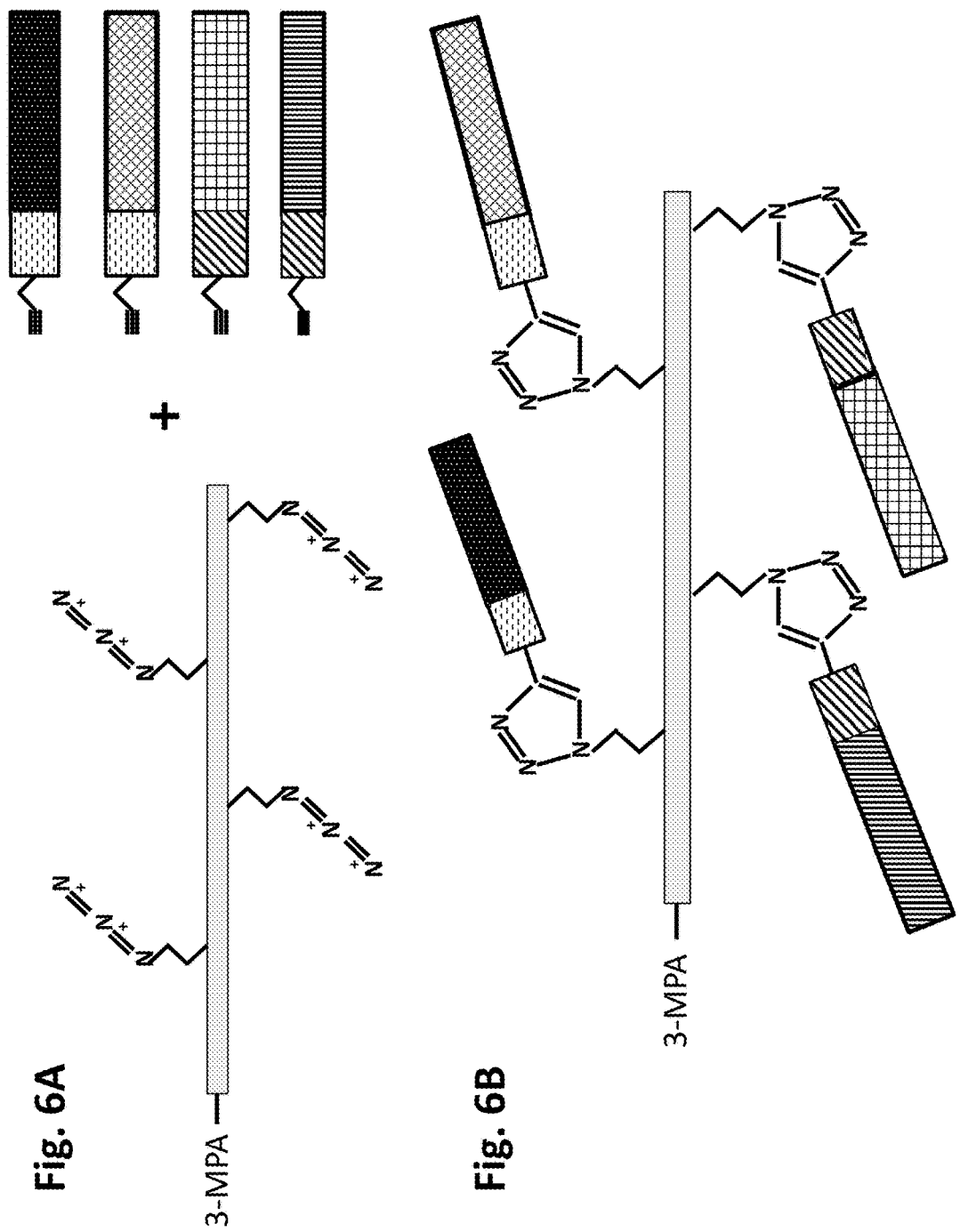

FIGS. 6A-B demonstrate the protein conjugation chemistry of one embodiment of the branched peptide using a stem peptide that contains four azidonorleucine residues and peptides (branches) that contain propargyl glycine at the amino terminus (FIG. 6A). Incubation of equimolar concentrations of the branches with the stem peptide in DMSO in the presence of 10 mg in 4 ml of the CuSO$_4$5H2O catalyst mixed with 10 mg in 4 ml ascorbic acid overnight resulted in the formation of the branched peptide used for conjugation. The final concentration of DMSO for the reaction was 50%. The branched peptides were purified using HPLC and verified using mass spectrometry (FIG. 6B). The peptides contain an N-terminal amide group (-nh2) which is useful in peptide stability compared with the usual carboxyl group (—COOH).

Figure 7B:
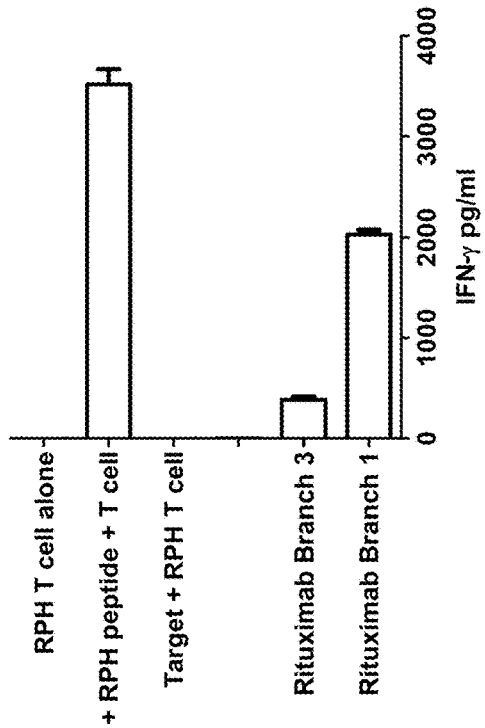
Figure 7A:
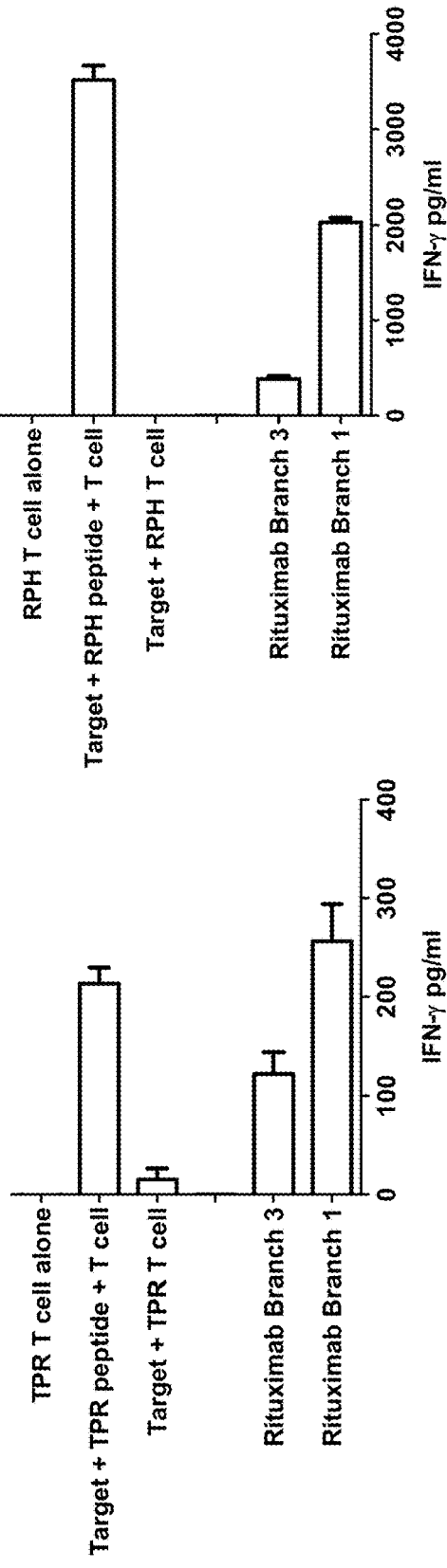

FIGS. 7A-B demonstrate recognition of a lymphoblastoid lymphoma cell line by CD8+ cytomegalovirus-specific cytotoxic T lymphocytes through conjugation of polytope peptides in the branched peptide format. Antibody is conjugated using the embodiment in FIG. 6B using the following peptides:

Stem:
(SEQ ID NO: 168)
SEEZSEEZSEEZSEEZ (Z: Azidonorleucine);

For Branch 1 TPEC:
branch 1-1:
(SEQ ID NO: 169)
BKPAKFFRLTPRVTGGGAM-nh2 (B: propargyl glycine);

Branch 1-2:
(SEQ ID NO: 170)
BKPAKFFRLRPHERNGFTVL-nh2 (B: propargyl glycine);

Branch 1-3:
(SEQ ID NO: 171)
BKPAKFFRLRELRRKMMYM-nh2 (B: propargyl glycine);
and Branch 1-4:
(SEQ ID NO: 172)
BKPAKFFRLNLVPMVATV-nh2 (B: propargyl glycine);
and For Branch 3 TPEC, branch 3-1:
(SEQ ID NO: 173)
BAIPVSLRTPRVTGGGAM-nh2 (B: propargyl glycine);

Branch 3-2:
(SEQ ID NO: 174)
BAIPVSLRRPHERNGFTVL-nh2 (B: propargyl glycine);

Branch 3-3:
(SEQ ID NO: 175)
BAIPVSLRELRRKMMYM-nh2 (B: propargyl glycine);
and

Branch 3-4:
(SEQ ID NO: 176)
BAIPVSLVTEHDTLLY-nh2 (B: propargyl glycine).

Target lymphoma cells labeled with branched peptide TPEC are recognized by T cells specific for the RPHERNGFTVL (SEQ ID NO: 2) and TPRVTGGGAM (SEQ ID NO: 49) peptides. Untreated target cells are not recognized by the peptide-specific T cells (negative control) and free peptide pulsed target cells are strongly recognized by T cells (positive control).

Figure 8A:
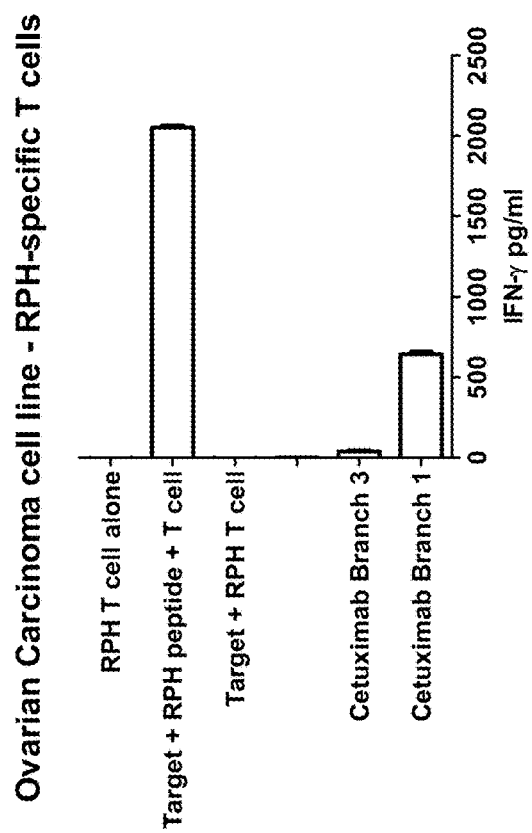
Figure 8B:
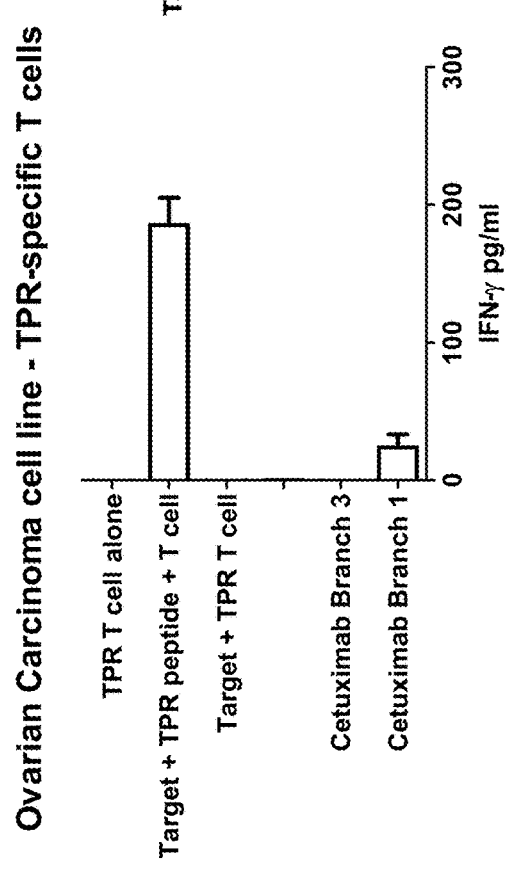

FIGS. 8A-B demonstrate recognition of an ovarian carcinoma cell line by CD8+ cytomegalovirus-specific cytotoxic T lymphocytes through conjugation of polytope peptides in the branched peptide format. Antibody is conjugated using the embodiment in FIG. 6B using peptides Stem:
(SEQ ID NO: 168)
SEEZSEEZSEEZSEEZ (Z: Azidonorleucine);

For Branch 1 TPEC, branch 1-1:
(SEQ ID NO: 169)
BKPAKFFRLTPRVTGGGAM-nh2 (B: Propargyl glycine);

Branch 1-2:
(SEQ ID NO: 170)
BKPAKFFRLRPHERNGFTVL-nh2 (B: Propargyl glycine);

Branch 1-3:
(SEQ ID NO: 171)
BKPAKFFRLRELRRKMMYM-nh2 (B: Propargyl glycine);

Branch 1-4:
(SEQ ID NO: 172)
BKPAKFFRLNLVPMVATV-nh2 (B: Propargyl glycine);
and

For Branch 3 TPEC, branch 3-1:
(SEQ ID NO: 173)
BAIPVSLRTPRVTGGGAM-nh2 (B: Propargyl glycine);

Branch 3-2:
(SEQ ID NO: 174)
BAIPVSLRRPHERNGFTVL-nh2 (B: Propargyl glycine);

Branch 3-3:
(SEQ ID NO: 175)
BAIPVSLRELRRKMMYM-nh2 (B: Propargyl glycine);
and

Branch 3-4:
(SEQ ID NO: 176)
BAIPVSLVTEHDTLLY-nh2 (B: Propargyl glycine).

Target lymphoma cells labeled with branched peptide TPEC are recognized by T cells specific for the RPHERNGFTVL (SEQ ID NO: 2) and TPRVTGGGAM (SEQ ID NO: 49) peptides. Untreated target cells are not recognized by the peptide-specific T cells (negative control) and free peptide pulsed target cells are strongly recognized by T cells (positive control).

Figures 9A, 9B:
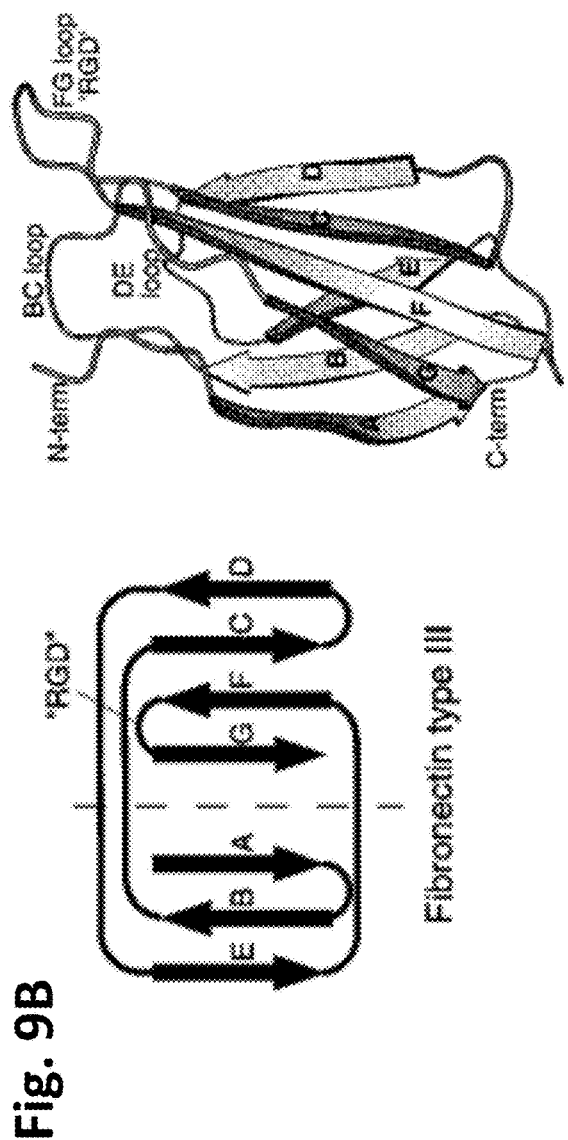
Figure 9C:
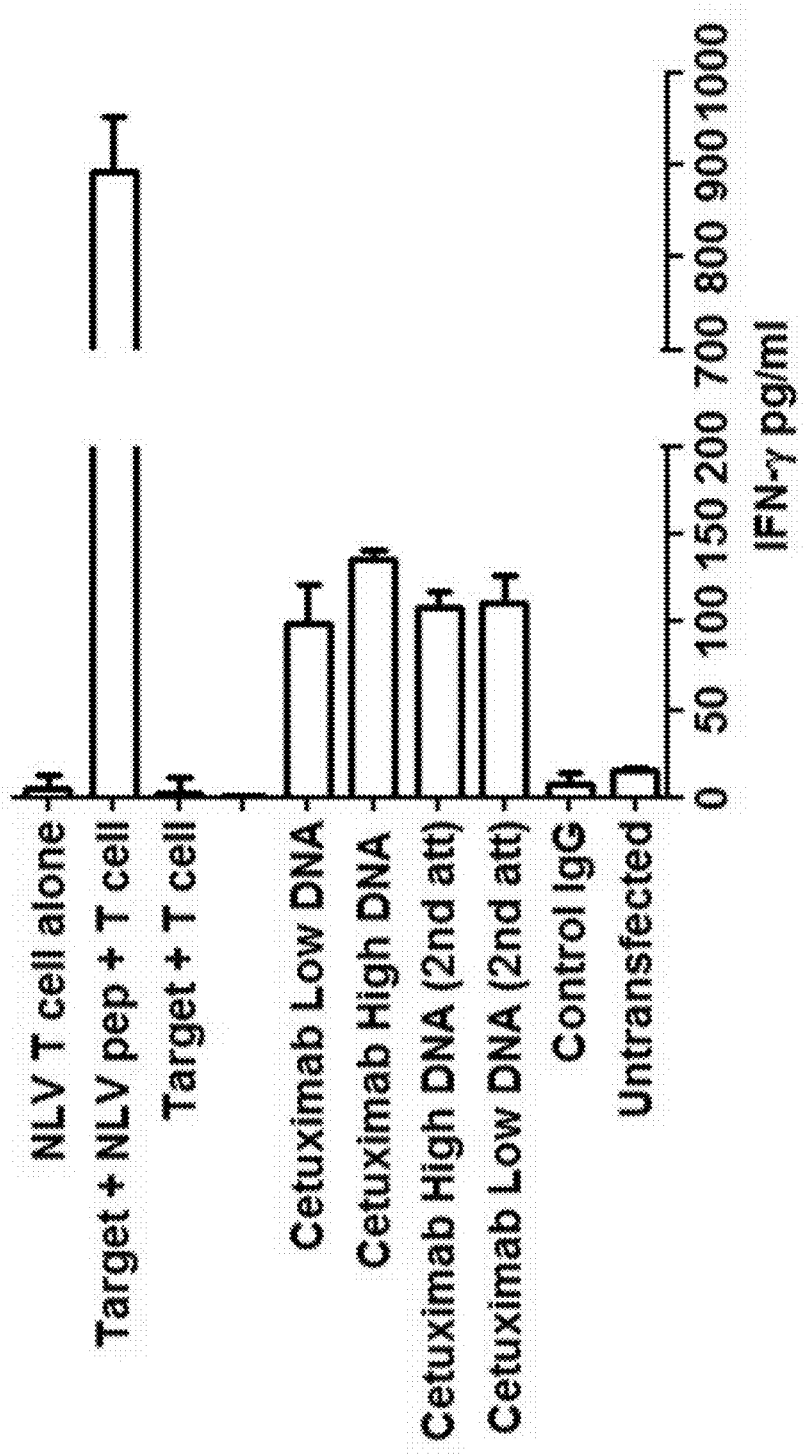

FIGS. 9A-C provide an embodiment of the bundled domain TPEC.

FIG. 9A demonstrates the scaffold (Fibronectin type 3 domain from the fibronectin 1 protein) used for the bundled domain TPEC. The bundled domain sequence (FIG. 9A) demonstrates the mutations made in the outer loops of the domain and contains viral epitopes separated from the fibronectin sequence on both sides by a protease recognition sequence specific for MMP2. The protease cleavage sites are underlined and the viral epitope are shown in bold and italics. FIG. 9B demonstrates the structure of the bundled domain and the "BC", "DE" and "FG" loops that contain the viral epitopes. FIG. 9C demonstrates recognition of an ovarian carcinoma cell line by CD8+ cytomegalovirus specific cytotoxic T lymphocytes. CMV epitopes are contained within an additional protein domain linked to the heavy chain of Cetuximab. The viral epitopes are flanked by an MMP2 protease recognition sequence which will allow release of the viral epitopes in the presence of MMP2, produced by the target cell line. The bundled domain TPEC is produced in Expi293 cells and purified using protein A sepharose beads.

Target ovarian carcinoma cells labelled with the bundled domain TPEC are recognized by T cells specific for the viral epitope NLVPMVATV (SEQ ID NO: 1) by release of IFN-γ. Four different preparations (two TPECs produced on each of two days using different concentrations of DNA) of the bundled domain were used, all of which produced similar amounts of bundled domain TPEC and produced similar recognition of target cells by the peptide-specific T cells. Untreated target cells are not recognized by the peptide-specific T cells (negative control) and free peptide pulsed target cells are strongly recognized by T cells (positive control).

DESCRIPTION OF THE SEQUENCES

Table 1 provides a listing of certain sequences referenced herein.

TABLE 1

Description of the Sequences and SEQ ID NOs

| Description | Sequence | # |
|---|---|---|
| T-cell epitope from cytomegalovirus (CMV TCE) (pp65, position 495-503, HLA-A2) | NLVPMVATV | 1 |
| CMV TCE (pp65, position 265-275, HLA-B7) | RPHERNGFTVL | 2 |
| CMV TCE and cleavage site from capthepsin B | NLVPMVATVASG**V{Cit}**GC cleavage site in bold. {Cit} = citrulline | 3 |
| CMV TCE and cleavage site from capthepsin B | RPHERNGFTVLASGFKGC cleavage site in bold | 4 |
| CMV TCE (IE1, position 316-324, HLA-A2) | VLEETSVML | 5 |
| CMV TCE (IE1, 309-317, HLA-C7) (Peptidomimetic of SEQ ID NO: 17) | BRVLBBYVL, where B is alpha-aminobutyric acid, a homolog for cysteine | 6 |
| CMV TCE (1E1,315-323, HLA-A2) | YILEETSVM | 7 |
| CMV TCE and cleavage site from capthepsin B | VLEETSVMLASGFKGC cleavage site in bold | 8 |
| CMV TCE and cleavage site from capthepsin B | BRVLBBYVLASGFKGC, where B is alpha-aminobutyric acid cleavage site in bold | 9 |
| CMV TCE and cleavage site from capthepsin B | YILEETSVMASGFKGC cleavage site in bold | 10 |
| Polytope containing two different CMV-derived epitopes separated by cathepsin B cleavage site | CGVANLVPMVATVAVAVLEETSVML cleavage sites in bold | 11 |
| Polytope containing two different CMV-derived epitopes separated by cathepsin B cleavage site | CVARPHERNGFTVLVANLVPMVATV cleavage sites in bold | 12 |
| Polytope containing two different CMV-derived epitopes separated by cathepsin B cleavage site | CGVANLVPMVATVARPHERNGFTVL cleavage sites in bold | 13 |
| Polytope containing five different CMV-derived epitopes separated by cathepsin B cleavage sites | CGSFRVTEHDTLLYGSFRRPHERNGFTVLGSFRELKRKMIYMGSFRNLVPMVATV cleavage sites in bold | 14 |

TABLE 1-continued Description of the Sequences and SEQ ID NOs

| Description | Sequence | # |
|---|---|---|
| CMV TCE (IE1,32-41, HLA-A68) | ATTFLQTMLR | 15 |
| CMV TCE (pp65, 103-114, HLA-B35) | CPSQEPMSIYVY | 16 |
| CMV TCE (IE1, 309-317, HLA-C7) | CRVLCCYVL | 17 |
| CMV TCE (IE1, 279-287, HLA-A1/B18) | CVETMCNEY | 18 |
| CMV TCE (IE1, 198-206, HLA-A1/B18) | DELRRKMMY | 19 |
| CMV TCE (pp65,31-40, HLA-A68) | DTPVLPHETR | 20 |
| CMV TCE (IE1, 381-389, HLA-B44) | EEAIVAYTL | 21 |
| CMV TCE (pp65, 512-521, HLA-B44) | EFFDANDIY | 22 |
| CMV TCE (IE1, 199-207, HLA-B8) | ELKRKMIYM | 23 |
| CMV TCE (IE1, 199-207, HLA-B8) | ELRRKMMYM | 24 |
| CMV TCE (IE1, 334-342, HLA-A68) | EVISVMKRR | 25 |
| CMV TCE (IE2,381-389, HLA-B41) | FEQPTETPP | 26 |
| CMV TCE (IE1, 221-231, HLA-B55) | FPKTTNGCSQA | 27 |
| CMV TCE (pp65, 188-195, HLA-B35) | FPTKDVAL | 28 |
| CMV TCE (pp65, 369-379, HLA-A24) | FTSQYRIQGKL | 29 |
| CMV TCE (pp65, 186-196, HLA-A68) | FVFPTKDVALR | 30 |
| CMV TCE (IE2, 242-250, HLA-A2) | IIYTRNHEVK | 31 |
| CMV TCE (pp65, 123-131, HL.A-B35) | IPSINVHHY | 32 |
| CMV TCE (pp150, 101-109, HLA-B7) | KARDHLAVL | 33 |
| CMV TCE (IE1, 42-50, HLA-B40) | KEVNSQLSL | 34 |
| CMV TCE (IE1, 201-209, HLA-B27) | KRKMIYMCY | 35 |
| CMV TCE (pp65, 120-128, HLA-A2) | MLNIPSINV | 36 |
| CMV TCE (pp150, 212-220, HLA-B7) | NVRRSWEEL | 37 |
| CMV TCE (IE1, 88-96, HLA-B8) | QIKVRVDMV | 38 |
| CMV TCE (pp65, 52-61, HLA-B35) | QPSLILVSQY | 39 |
| CMV TCE (pp150, 792-802, HLA-A68) | QTVTSTPVQGR | 40 |

TABLE 1-continued

Description of the Sequences and SEQ ID NOs

| Description | Sequence | # |
|---|---|---|
| CMV TCE (pp65, 341-349, HLA-A24) | QYDVPAALF | 41 |
| CMV TCE (pp65, 222-231, HLA-A24) | QYVKVYLESF | 42 |
| CMV TCE (pp50, 274-282, HLA-A1) | RGDPFDKNY | 43 |
| CMV TCE (pp65, 522-530, HLA-A2) | RIFAELEGV | 44 |
| CMV TCE (gB, 4-12, HLA-A2) | RIWCLWCV | 45 |
| CMV TCE (IE1, 341-349, HLA-B27) | RRIEEICMK | 46 |
| CMV TCE (IE1, 201-209, HLA-B27) | RRKMMYMCY | 47 |
| CMV TCE (pp65, 364-373, HLA-B44) | SEHPTFTSQY | 48 |
| CMV TCE (pp65, 417-426, HLA-B7) | TPRVTGGGAM | 49 |
| CMV TCE (pp150, 945-955, HLA-A3) | TTVYPPSSTAK | 50 |
| CMV TCE (pp50, 52-60, HLA-A3) | TVRSHCVSK | 51 |
| CMV TCE (IE1, 81-89, HLA-A2) | VLAELVKQI | 52 |
| CMV TCE (pp50, 245-253, HLA-A1) | VTEHDTLLY | 53 |
| CMV TCE (pp65, 113-121, HLA-A24) | VYALPLKML | 54 |
| CMV TCE (pp65, 363-373, HLA-A1) | YSEHPTFTSQY | 55 |
| CMV TCE (pp65, 61-70, HLA-A68) | YTPDSTPCHR | 56 |
| CMV TCE (IE1, 316-324, HLA-A2) | YVLEETSVM | 57 |
| CMV TCE and cleavage site from ADAM28 | CKPAKFFRLNLVPMVATV | 58 |
| CMV TCE and cleavage site from ADAM28 | CKPAKFFRLRPHERNGFTVL | 59 |
| CMV TCE and cleavage site from capthepsin D | CPRSFFRLGKVLEETSVML | 60 |
| CMV TCE and cleavage site from ADAM28 | CKPAKFFRLELRKMIYM | 61 |
| CMV TCE and cleavage site from capthepsin D | CPRSFFRLGKQIKVRVDMV | 62 |
| Polytope comprising four different cytomegalovirus epitopes, each separated by either an ADAM28 or cathepsin D cleavage site | CGSKPAKFFRLYSEHPTFTSQYGSPRSFFRLGKTPRVTGGGAMGSKPAKFFRLQIKVRVDMVGSPRSFFRLGKELRRKMMYM | 63 |
| T-cell epitope from Epstein Barr Virus (EBV TCE) EBNA1 | RPQKRPSCI | 64 |
| EBV TCE EBNA1 | HPVGEADYF | 65 |
| EBV TCE EBNA1 | HPVGEADYFEY | 66 |
| EBV TCE EBNA1 | IPQCRLTPL | 67 |

TABLE 1-continued

Description of the Sequences and SEQ ID NOs

| Description | Sequence | # |
|---|---|---|
| EBV TCE EBNA1 | VLKDAIKDL | 68 |
| EBV TCE EBNA2 | YHLIVDTDSL | 69 |
| EBV TCE EBNA2 | DTPLIPLTIF | 70 |
| EBV TCE EBNA2 | RPTELQPTP | 71 |
| EBV TCE EBNA3A | QAKWRLQTL | 72 |
| EBV TCE EBNA3A | AYSSWMYSY | 73 |
| EBV TCE EBNA3A | RYSIFFDY | 74 |
| EBV TCE EBNA3A | FLRGRAYGL | 75 |
| EBV TCE EBNA3A | KRPPIFIRRL | 76 |
| EBV TCE EBNA3A | RPPIFIRRL | 77 |
| EBV TCE EBNA3A | LEKARGSTY | 78 |
| EBV TCE EBNA3A | HLAAQGMAY | 79 |
| EBV TCE EBNA3A | YPLHEQHGM | 80 |
| EBV TCE EBNA3A | VFSDGRVAC | 81 |
| EBV TCE EBNA3A | VPAPAGPIV | 82 |
| EBV TCE EBNA3A | SVRDRLARL | 83 |
| EBV TCE EBNA3A | RLRAEAQVK | 84 |
| EBV TCE EBNA3A | VQPPQLTLQV | 85 |
| EBV TCE EBNA3B | HRCQAIRKK | 86 |
| EBV TCE EBNA3B | TYSAGIVQI | 87 |
| EBV TCE EBNA3B | RRARSLSAERY | 88 |
| EBV TCE EBNA3B | VSFIEFVGW | 89 |
| EBV TCE EBNA3B | AVFDRKSDAK | 90 |
| EBV TCE EBNA3B | IVTDFSVIK | 91 |
| EBV TCE EBNA3B | AVLLHEESM | 92 |
| EBV TCE EBNA3B | VEITPYKPTW | 93 |
| EBV TCE EBNA3C | EGGVGWRHW | 94 |
| EBV TCE EBNA3C | QNGALAINTF | 95 |
| EBV TCE EBNA3C | LRGKWQRRYR | 96 |
| EBV TCE EBNA3C | RRIYDLIEL | 97 |
| EBV TCE EBNA3C | HHIWQNLL | 98 |
| EBV TCE EBNA3C | EENLLDFVRF | 99 |
| EBV TCE EBNA3C | LLDFVRFMGV | 100 |
| EBV TCE EBNA3C | LDFVRFMGV | 101 |
| EBV TCE EBNA3C | KEHVIQNAF | 102 |
| EBV TCE EBNA3C | FRKAQIQGL | 103 |
| EBV TCE EBNA3C | QPRAPIRPI | 104 |
| EBV TCE EBNA-LP | SLREWLLRI | 105 |

TABLE 1-continued

Description of the Sequences and SEQ ID NOs

| Description | Sequence | # |
|---|---|---|
| EBV TCE LMP1 | FWLYIVMSD | 106 |
| EBV TCE LMP1 | FRRDLLCPLGA | 107 |
| EBV TCE LMP1 | YLLEMLWRL | 108 |
| EBV TCE LMP1 | YLQQNWWTL | 109 |
| EBV TCE LMP1 | TLLVDLLWL | 110 |
| EBV TCE LMP1 | DPHGPVQLSYYD | 111 |
| EBV TCE LMP2 | MGSLEMVPM | 112 |
| EBV TCE LMP2 | EDPYWGNGDRHSDYQ | 113 |
| EBV TCE LMP2 | NPVCLPVIVAPYLF | 114 |
| EBV TCE LMP2 | LPVIVAPYL | 115 |
| EBV TCE LMP2 | PYLFWLAAI | 116 |
| EBV TCE LMP2 | ASCFTASVSTVVTA | 117 |
| EBV TCE LMP2 | FTASVSTVV | 118 |
| EBV TCE LMP2 | IEDPPFNSL | 119 |
| EBV TCE LMP2 | RRRWRRLTV | 120 |
| EBV TCE LMP2 | RRWRRLTVC | 121 |
| EBV TCE LMP2 | RRLTVCGGIMF | 122 |
| EBV TCE LMP2 | TVCGGIMFL | 123 |
| EBV TCE LMP2 | MFLACVLVLIVDAV | 124 |
| EBV TCE LMP2 | LIVDAVLQL | 125 |
| EBV TCE LMP2 | GLGTLGAAI | 126 |
| EBV TCE LMP2 | LLWTLVVLL | 127 |
| EBV TCE LMP2 | SSCSSCPLSKI | 128 |
| EBV TCE LMP2 | ILLARLFLY | 129 |
| EBV TCE LMP2 | FLYALALLL | 130 |
| EBV TCE LMP2 | TYGPVFMCL | 131 |
| EBV TCE LMP2 | CLGGLLTMV | 132 |
| EBV TCE LMP2 | VMSNTLLSAW | 133 |
| EBV TCE LMP2 | LTAGFLIFL | 134 |
| EBV TCE LMP2 | LLSAWILTA | 135 |
| EBV TCE BRLF1 | LVSDYCNVLNKEFT | 136 |
| EBV TCE BRLF1 | LVSDYCNVL | 137 |
| EBV TCE BRLF1 | DYCNVLNKEF | 138 |
| EBV TCE BRLF1 | AENAGNDAC | 139 |
| EBV TCE BRLF1 | IACPIVMRYYVLDHLI | 140 |
| EBV TCE BRLF1 | YVLDHLIVV | 141 |
| EBV TCE BRLF1 | FFIQAPSNRVMIPAT | 142 |
| EBV TCE BRLF1 | ATIGTAMYK | 143 |

TABLE 1-continued

Description of the Sequences and SEQ ID NOs

| Description | Sequence | # |
|---|---|---|
| EBV TCE BRLF1 | KHSRVRAYTYSKVLG | 144 |
| EBV TCE BRLF1 | RALIKTLPRASYSSH | 145 |
| EBV TCE BRLF1 | ERPIFPHPSKPTFLP | 146 |
| EBV TCE BRLF1 | QKEEAAICGQMDLS | 147 |
| EBV TCE BRLF1 | EVCQPKRIRPFHPPG | 148 |
| EBV TCE BZLF1 | LPEPLPQGQLTAY | 149 |
| EBV TCE BZLF1 | EPLPQGQLTAY | 150 |
| EBV TCE BZLF1 | APENAYQAY | 151 |
| EBV TCE BZLF1 | LQHYREVAA | 152 |
| EBV TCE BZLF1 | DSELEIKRYKNR | 153 |
| EBV TCE BZLF1 | RKCCRAKFKQLLQHYR | 154 |
| EBV TCE BZLF1 | RAKFKQLL | 155 |
| EBV TCE BZLF1 | SENDRLRLL | 156 |
| T-cell epitope from Influenza A Virus (IAV TCE) PR8 | CTELKLSDY | 157 |
| IAV TCE PB1 | VSDGGPNLY | 158 |
| IAV TCE MP | GILGFVFTL | 159 |
| IAV TCE MP | ILGFVFTLTV | 160 |
| IAV TCE PR8 | ILRGSVAHK | 161 |
| IAV TCE MP | SIIPSGPLK | 162 |
| IAV TCE MP1 | RMVLASTTAK | 163 |
| IAV TCE MP2 | KSMREEYRK | 164 |
| IAV TCE NP | SPIVPSFDM | 165 |
| IAV TCE PB1 | QPEWFRNVL | 166 |
| IAV TCE NP | SRYWAIRTR | 167 |
| Stem for branched peptide | SEEZSEEZSEEZSEEZ, wherein Z is Az idonorleucine | 168 |
| Branch 1-1 for branched peptide | BKPAKFFRLTPRVTGGGAM-nh2, wherein B is propargyl glycine | 169 |
| Branch 1-2 for branched peptide | BKPAKFFRLRPHERNGFTVL-nh2, wherein B is propargyl glycine | 170 |
| Branch 1-3 for branched peptide | BKPAKFFRLRELRRKMMYM-nh2, wherein B is propargyl glycine | 171 |
| Branch 1-4 for branched peptide | BKPAKFFRLNLVPMVATV-nh2, wherein B is propargyl glycine | 172 |
| Branch 3-1 for branched peptide | BAIPVSLRTPRVTGGGAM-nh2, wherein B is propargyl glycine | 173 |

TABLE 1-continued

Description of the Sequences and SEQ ID NOs

| Description | Sequence | # |
|---|---|---|
| Branch 3-2 for branched peptide | BAIPVSLRRPHERNGFTVL-nh2, wherein B is propargyl glycine | 174 |
| Branch 3-3 for branched peptide | BAIPVSLRELRRKMMYM-nh2, wherein B is propargyl glycine | 175 |
| Branch 3-4 for branched peptide | BAIPVSLVTEHDTLLY-nh2, wherein B is propargyl glycine | 176 |
| C1s cleavage site | YLGRSYKV | 177 |
| C1s cleavage site | MQLGRX | 178 |
| MASP2 cleavage site | SLGRKIQI | 179 |
| C2a cleavage site | GLARSNLDE | 180 |
| Cathepsin D cleavage site | PRSFFRLGK | 181 |
| ADAM28 cleavage site | KPAKFFRL | 182 |
| ADAM28 cleavage site | DPAKFFRL | 183 |
| ADAM28 cleavage site | KPMKFFRL | 184 |
| ADAM28 cleavage site | LPAKFFRL | 185 |
| MMP2 cleavage site | AIPVSLR | 186 |
| Bundled domain sequence | SASGGGSGGGSVSDVPRDLEVVAATPTSLLISWDAPAVGGGGSGGGGSTIPVSLRSTPRVTGGGAMTIPVSLRSGGGGSGGGGSTVRYYRITYGETGGNSPVQEFTVPGSKSTATISGLKPGVDYTITVYAVTGGGGGSGGGGSTIPVSLRSNLVPMVATVTIPVSLRSGGGGSGGGGSSPASSKPISINYRTGGGGSGGGGSTIPVSLRSVLEETSVML | 187 |
| MA4P2 cleavage site | TIPVSLRS | 188 |

DESCRIPTION OF THE EMBODIMENTS

I. Targeting Moiety Peptide Epitope Complexes Having a Plurality of T-Cell Epitopes A variety of targeting moiety peptide epitope complexes (TPECs) are described in different embodiments. In each of the embodiments, however, a targeting moiety may be used to deliver the TPEC to an area of unwanted cells, allowing for a therapeutic effect to be delivered locally. The TPEC also contains a plurality of T-cell epitopes. The TPEC further comprises cleavage sites that release the T-cell epitopes from the targeting agent, and in some embodiments from each other, when they are in the microenvironment of the unwanted cells. Although the arrangement and number of T-cell epitopes varies in different embodiments described herein, once cleaved from the targeting agent (and any neighboring T-cell epitopes), the T-cell epitopes function by stimulating an immune response against the unwanted cells. In some embodiments, maximal benefits may be achieved by releasing all of the T-cell epitopes from both the targeting agent and from each other in the cleavage process, allowing each T-cell epitope to attract an immune response to the unwanted cell.

Having a plurality of T-cell epitopes, as discussed in detail below, enhances the immune response against the unwanted cells, either by stimulating a stronger immune response in a given patient or by allowing the TPEC to stimulate an immune response across a wide variety of patients in different ethnic and racial groups. In one embodiment, and while not being bound by theory, the cleavage at the cleavage site allows the T-cell epitopes to be trimmed at either or both ends to the appropriate length to produce a peptide that can fit in the peptide-binding groove of HLA class I and be recognized by T-cells, so as to initiate an immune response.

Without cleavage of these epitopes, the prior art fails to stimulate a sufficient T-cell response because the T-cell epitopes fused together would not be adequately recognized by the patients T-cells and would, thus, not initiate an immune response against the cancer cells.

A. TPECs with a Plurality of T-Cell Epitopes Separately Conjugated

In one embodiment, the TPEC comprises a plurality of T-cell epitopes that are separately conjugated to the targeting moiety. Because the T-cell epitopes will be separately conjugated to the targeting moiety, with two exemplary embodiments shown in FIGS. 1A and 1B, this embodiment may be termed the "hairy" embodiment as the T-cell epitopes protrude from the targeting moiety like individual hairs from a person's skin. In other words, in some embodiments, a composition for retargeting an immune response to unwanted cells may comprise a TPEC comprising the formula T-(L-C-E)$_n$. In such embodiments, a plurality of L-C-E, each attach separately to T, wherein:

(a) T is a targeting moiety that is capable of targeting unwanted cells;

(b) L is a linker capable of chemical linkage to T;

(c) C is a cleavage site that is (i) cleaved by an enzyme expressed by the unwanted cells; (ii) cleaved through a pH-sensitive cleavage reaction inside the unwanted cell; (iii) cleaved by a complement-dependent cleavage reaction; or (iv) cleaved by a protease that is colocalized to the unwanted cell by a targeting moiety that is the same or different from the targeting moiety in the TPEC; and (d) E is a T-cell epitope.

N is an integer of at least 2 (optionally from about 2 to 50). The same cleavage site may optionally be used multiple times in the TPEC and the same epitope may optionally be used multiple times in the TPEC.

The C and E moieties may be the same in the plurality of L-C-E moieties affixed to a single T or a single T may have different C and E moieties in the plurality of L-C-E moieties. Thus, there may be more than one type of cleavage site or only one type of cleavage site. There may also, independently, be more than one type of T-cell epitope or only one type of T-cell epitope.

In certain aspects of the embodiments discussed in this section, the L-C-E complexes may be affixed to the targeting moiety in a random fashion. Thus, in a preparation of TPECs with a plurality of T-cell epitopes separately conjugated to the targeting moiety, some TPECs may have greater numbers of T-cell epitopes and some may have fewer numbers. Additionally, in a preparation of TPECs with a plurality of T-cell epitopes separately conjugated to the targeting moiety, the location of TPECs may differ throughout the preparation. In this vein, when these compounds are administered to a patient suffering from a disease such as cancer, the patient's body will have a much more difficult time mounting an inhibitory immune response against the preparation of TPECs. This may allow the patient to receive multiple doses of the TPEC preparation over a significant period of time, as discussed further below in Section III.B below.

B. TPECs with at Least One Polytope

In another embodiment, the TPEC comprises a plurality of T-cell epitopes that are conjugated to the targeting moiety as a polytope (for poly-epitope), but the conjugation within the polytope and to the targeting moiety occurs through cleavage sites allowing the release of the individual T-cell epitopes in the microenvironment of the unwanted cells. Several embodiments of this arrangement are shown in FIGS. 2A, 2B, and 2C. Thus, the polytope itself can have a linear and/or bundled configuration (like FIGS. 2A and 2B) or a branched configuration like a hairbrush with bristles (like FIG. 2C).

In FIGS. 2A-B, a composition for retargeting an immune response to unwanted cells comprises a TPEC having at least one of L-(C-E)n with each C-E attached to the L in series and the L attached to the T. It may have one or a plurality of L-(C-E)n attached to the T. In the embodiments of FIGS. 2A-B, the linker may be either a chemical linker, a peptide bond, or at least one peptide.

In FIG. 2C, a composition for retargeting an immune response to unwanted cells comprises at TPEC having at least one of L-(C-E)n with each C-E attached to the L in parallel and the L attached to the T. It may have one or a plurality of L-(C-E)n attached to the T. In embodiment 2C, the linker may be a chemical linker.

In all of the embodiments of FIG. 2A-C, (a) T is a targeting moiety that is capable of targeting unwanted cells;

(b) L is a linker capable of chemical or peptide linkage to T (including a peptide bond);

(c) C is a cleavage site (i) cleaved by an enzyme expressed by the unwanted cells; (ii) cleaved through a pH-sensitive cleavage reaction inside the unwanted cell; (iii) cleaved by a complement-dependent cleavage reaction; or (iv) cleaved by a protease that is colocalized to the unwanted cell by a targeting moiety that is the same or different from the targeting moiety in the TPEC; and (d) E is a T-cell epitope;

wherein n is an integer of at least 2 (optionally from about 2 to 50).

The C and E moieties may be the same in the plurality of C-E moieties affixed through L to a single T or a single T may have different C and E moieties in the plurality of C-E moieties. Thus, there may be more than one type of cleavage site or only one type of cleavage site. There may also, independently, be more than one type of T-cell epitope or only one type of T-cell epitope.

In some embodiments, the plurality of the T-cell epitopes being conjugated in a polytope allow for a uniform product to be produced that contains a standard group, number, and arrangement of T-cell epitopes, while still allowing for the release of all of the T-cell epitopes in the microenvironment of the unwanted cells. Microenvironment means the specific set of physical, chemical, and biological conditions in the vicinity of cells within a distance where these conditions can have an effect on or be sensed by the cells.

In some embodiments, more than one polytope are conjugated to the targeting moiety. In some embodiments from about 1 to 30, 1 to 20, or 1 to 10 polytopes are conjugated to the targeting moiety. In some embodiments, about 1, 2, 3, 4, 5, 6, 7, 8, 9, or 10 polytopes are conjugated to the targeting moiety, each group by one cleavage site. In these embodiments, the polytopes may be the same or different.

In some embodiments, the TPEC may have both at least one separately conjugated T-cell epitope and at least one polytope, according to sections I.A and I.B, respectively.

C. TPECs with More than 10 T-Cell Epitopes

In another embodiment, the TPEC comprises a plurality of T-cell epitopes that, irrespective of how they are arranged on the targeting moiety, comprise more than 10 T-cell epitopes. In these embodiments, the T-cell epitopes may be separately conjugated or conjugated in a polytope. In other words, a composition for retargeting an immune response to unwanted cells may comprise a TPEC having:

(a) a targeting moiety that is capable of targeting unwanted cells;

(b) a plurality of more than 10 T-cell epitopes conjugated to the targeting moiety with at least one cleavage site, wherein the cleavage site is (i) cleaved by an enzyme expressed by the unwanted cells; (ii) cleaved through a pH-sensitive cleavage reaction inside the unwanted cell; (iii) cleaved by a complement-dependent cleavage reaction; or (iv) cleaved by a protease that is colocalized to the unwanted cell by a targeting moiety that is the same or different from the targeting moiety in the TPEC.

In some embodiments, including TPECs with more than 10 T-cell epitopes, the immune response against the unwanted cells is notably stronger. In some embodiments, including TPECs with more than 10 T-cell epitopes, the TPEC can be used to treat a greater proportion of patients suffering from the condition characterized by unwanted cells.

In some compositions with TPECs having more than 10 T-cell epitopes, the T-cell epitopes may be separately conjugated to the targeting moiety, each T-cell epitope by a cleavage site. In some embodiments, with TPECs having more than 10 T-cell epitopes, the T-cell epitopes may be conjugated to the targeting moiety as at least one polytope, each polytope conjugated to the targeting moiety by a cleavage site. In some embodiments, the T-cell epitopes within a polytope have cleavage sites between them.

D. Compositions Comprising TPECs

A composition may comprise a plurality of TPECs. In some embodiments, all of the TPECs in the composition are the same. In some embodiments, at least some of the TPECs in the composition are not identical.

In some embodiments, each TPEC is conjugated to a plurality of identical T-cell epitopes.

In some embodiments, at least some of the TPECs in the composition are conjugated to a plurality of T-cell epitopes that are not identical.

In some embodiments, a composition may comprise at least about 2, 3, 4, 5, 6, 7, 8, 9, 10, 15, 20, 25, or more different TPECs.

E. T-Cell Epitopes

T-cell epitopes function in the TPECs to attract the patient's own immune response to attack the unwanted cell by labeling it with antigenic T-cell epitopes from infectious agents.

Depending on desired aspects of the therapy, a variety of optional factors may be considered when choosing T-cell epitopes. Every person has six HLA class-I molecules that can bind peptides to present to CD8 T cells with some HLA types more prevalent in the population than others, such as HLA-A201 which is found in ~45% of the Caucasian population. In situations where the epitopes chosen for conjugation are able to bind to a limited set of HLA molecules that are only found in a proportion of the population, the TPEC may not have any or as much effectiveness in other segments of the population. Using HLA-A201 as an example, if the targeting moiety is conjugated with a T-cell epitope that binds to HLA-A201 then only patients that express HLA-A201 would bind the epitope and present it to T cells and initiate an immune response. However, in patients who are HLA-A201 negative the epitope may not be able to bind to their HLA molecules and there would be no or a lesser immune response. In situations where the therapy may be provided to a wide segment of the population having different HLA molecules, using different epitopes that bind to more HLA molecules could enhance the effectiveness of the TPEC across the population.

As an additional factor to consider, in some embodiments, T-cell epitopes may be chosen from those that a particular person has been exposed to, a wide variety of people have been exposed to, or for which vaccines have or can be administered. T cells generally recognize the epitope in complex with an HLA molecule when the patient has been previously infected with the virus from which the epitope is derived (or in instances where the patient has previously received a vaccine containing those epitopes). Vaccines may have been administered for a prior purpose (such as childhood vaccines) or may be administered preceding TPEC treatment with the same epitope.

In certain instances, T-cell epitopes are chosen from cytomegalovirus (CMV), influenza, Epstein Barr virus (EBV), varicella zoster, mumps, measles, rubella, adenovirus, polio, vaccinia, RSV, rotavirus, tetanus, vaccinia, and yellow fever T-cell epitopes. Epitopes may be chosen from infectious agents that are prevalent across the population in question or for which there are vaccines that are regularly administered or could be administered as part of a combination therapy approach.

In certain embodiments, the T-cell epitopes are chosen from at least 2, 3, 4, or 5 different infectious agents. In certain embodiments, at least some of the T-cell epitopes are CMV epitopes.

In any of the various TPECs described herein, in some embodiments, the plurality of T-cell epitopes are not all identical. In some embodiments, the plurality of T-cell epitopes are the same. In certain embodiments, the plurality of T-cell epitopes comprise some that are the same and some that are different.

The T-cell epitopes may be all MHC Class I restricted peptides, all MHC class II restricted peptides, or a combination of both Class I and Class II.

In some embodiments, the plurality of T-cell epitopes are from about 7 to 14 amino acids in length, from about 8 to 13, from about 9 to 12, about 9, or about 10 amino acids.

In some embodiments, at least 2, 3, 4, 5, 6, 7, 8, 9, or 10 different T-cell epitopes are used in the TPECs, whether the TPECs are the same or different. In some embodiments, using a plurality of different T-cell epitopes allows the agent to stimulate a T-cell response in at least about 10%, 15%, 20%, 25%, 30%, 35%, 40%, 45%, 50%, 60%, 70%, 80%, or 90% of the human population.

In some embodiments, the T-cell epitopes are chosen from HLA-A, HLA-B, HLA-C, HLA-E, HLA-F, HLA-G, CD1d, and MR1. In certain embodiments, the T-cell epitopes are chosen from HLA-A*01, HLA-A*02, HLA-A*03, HLA-A*11, HLA-A*24, HLA-B*44, HLA-B*07, HLA-B*08, HLA-B*15, HLA-B*35, HLA-B*40, HLA-C*07, HLA-C*03, HLA-C*05, HLA-C*04, HLA-C*06, and HLA-E*0101 restricted antigens.

In certain embodiments, the composition comprises at least the following T-cell epitopes HLA-A*02, HLA-A*01, and HLA-A*03.

When desired, more immunodominant T-cell epitopes may be selected. By immunodominant, we mean those epitopes that elicit the strongest immune response in a given patient and/or those that are known to be immunogenic across a wide cross-section of people.

In some embodiments, the T-cell epitopes comprise at least one of the epitopes provided in Table 2. In some embodiments, the T-cell epitopes are chosen from the epitopes provided in Table 2.

TABLE 2

Exempla T-Cell Epitope

| Peptide from | Sequence | Position | HLA Type |
|---|---|---|---|
| Cytomegalovirus Epitopes | | | |
| IE1 | ATTFLQTMLR (SEQ ID NO: 15) | 32-41 | HLA-A68 |
| IE1 | BRVLBBYVL (SEQ ID NO: 6) (variant of SEQ ID NO: 17, | 309-317 | HLA-C7 |

TABLE 2-continued

Exempla T-Cell Epitope

| Peptide from | Sequence | Position | HLA Type |
|---|---|---|---|
| | where the C residues are changed to B residues, wherein B is alpha-aminobutyric acid) | | |
| pp65 | CPSQEPMSIYVY (SEQ ID NO: 16) | 103-114 | HLA-B35 |
| IE1 | CRVLCCYVL (SEQ ID NO: 17) | 309-317 | HLA-C7 |
| IE1 | CVETMCNEY (SEQ ID NO: 18) | 279-287 | HLA-A1/B18 |
| IE1 | DELRRKMMY (SEQ ID NO: 19) | 198-206 | HLA-A1/B18 |
| pp65 | DTPVLPHETR (SEQ ID NO: 20) | 31-40 | HLA-A68 |
| IE1 | EEAIVAYTL (SEQ ID NO: 21) | 381-389 | HLA-B44 |
| pp65 | EFFDANDIY (SEQ ID NO: 22) | 512-521 | HLA-B44 |
| IE1 | ELKRKMIYM (SEQ ID NO: 23) | 199-207 | HLA-B8 |
| IE1 | ELRRKMMYM (SEQ ID NO: 24) | 199-207 | HLA-B8 |
| IE1 | EVISVMKRR (SEQ ID NO: 25) | 334-342 | HLA-A68 |
| IE2 | FEQPTETPP (SEQ ID NO: 26) | 381-389 | |
| IE1 | FPKTTNGCSQA (SEQ ID NO: 27) | 221-231 | HLA-B55 |
| pp65 | FPTKDVAL (SEQ ID NO: 28) | 188-195 | HLA-B35 |
| pp65 | FTSQYRIQGKL (SEQ ID NO: 29) | 369-379 | HLA-A24 |
| pp65 | FVFPTKDVALR (SEQ ID NO: 30) | 186-196 | HLA-A68 |
| 1E2 | IIYTRNHEVK (SEQ ID NO: 31) | 242-250 | HLA-A2 |
| pp65 | IPSINVHHY (SEQ ID NO: 32) | 123-131 | HLA-B35 |
| pp150 | KARDHLAVL (SEQ ID NO: 33) | 101-109 | HLA-B7 |
| IE1 | KEVNSQLSL (SEQ ID NO: 34) | 42-50 | HLA-B40 |
| IE1 | KRKMIYMCY (SEQ ID NO: 35) | 201-209 | HLA-B27 |
| pp65 | MLNIPSINV (SEQ ID NO: 36) | 120-128 | HLA-A2 |
| pp65 | NLVPMVATV (SEQ ID NO: 1) | 495-503 | HLA-A2 |
| pp150 | NVRRSWEEL (SEQ ID NO: 37) | 212-220 | HLA-B7 |
| IE1 | QIKVRVDMV (SEQ ID NO: 38) | 88-96 | HLA-B8 |
| pp65 | QPSLILVSQY (SEQ ID NO: 39) | 52-61 | HLA-B35 |
| pp150 | QTVTSTPVQGR (SEQ ID NO: 40) | 792-802 | HLA-A68 |
| pp65 | QYDVPAALF (SEQ ID NO: 41) | 341-349 | HLA-A24 |
| pp65 | QYVKVYLESF (SEQ ID NO: 42) | 222-231 | HLA-A24 |
| pp50 | RGDPFDKNY (SEQ ID NO: 43) | 274-282 | HLA-A1 |
| pp65 | RIFAELEGV (SEQ ID NO: 44) | 522-530 | HLA-A2 |
| gB | RIWCLVVCV (SEQ ID NO: 45) | 4-12 | HLA-A2 |
| pp65 | RPHERNGFTVL (SEQ ID NO: 2) | 265-275 | HLA-B7 |
| IE1 | RRIEEICMK (SEQ ID NO: 46) | 341-349 | HLA-B27 |
| IE1 | RRKMMYMCY (SEQ ID NO: 47) | 201-209 | HLA-B27 |
| pp65 | SEHPTFTSQY (SEQ ID NO: 48) | 364-373 | HLA-B44 |
| pp65 | TPRVTGGGAM (SEQ ID NO: 49) | 417-426 | HLA-B7 |
| pp150 | TTVYPPSSTAK (SEQ ID NO: 50) | 945-955 | HLA-A3 |
| pp50 | TVRSHCVSK (SEQ ID NO: 51) | 52-60 | HLA-A3 |
| IE1 | VLAELVKQI (SEQ ID NO: 52) | 81-89 | HLA-A2 |
| IE1 | VLEETSVML (SEQ ID NO: 5) | 316-324 | HLA-A2 |
| pp50 | VTEHDTLLY (SEQ ID NO: 53) | 245-253 | HLA-A1 |
| pp65 | VYALPLKML (SEQ ID NO: 54) | 113-121 | HLA-A24 |
| IE1 | YILEETSVM (SEQ ID NO: 7) | 315-323 | HLA-A2 |
| pp65 | YSEHPTFTSQY (SEQ ID NO: 55) | 363-373 | HLA-A1 |
| pp65 | YTPDSTPCHR (SEQ ID NO: 56) | 61-70 | HLA-A68 |
| IE1 | YVLEETSVM (SEQ ID NO: 57) | 316-324 | HLA-A2 |

Epstein Barr Virus

| Peptide from | Sequence | Position | HLA Type |
|---|---|---|---|
| EBNA1 | RPQKRPSCI (SEQ ID NO: 64) | 72-80 | HLA-B7 |
| EBNA1 | HPVGEADYF (SEQ ID NO: 65) | 407-415 | HLA-B53 |
| EBNA1 | HPVGEADYFEY (SEQ ID NO: 66) | 407-417 | HLA-B35 |
| EBNA1 | IPQCRLTPL (SEQ ID NO: 67) | 528-536 | HLA-B7 |
| EBNA1 | VLKDAIKDL (SEQ ID NO: 68) | 574-582 | HLA-A2 |
| EBNA2 | YHLIVDTDSL (SEQ ID NO: 69) | 14-23 | HLA-B38 |
| EBNA2 | DTPLIPLTIF (SEQ ID NO: 70) | 42-51 | HLA-A2/B51 |
| EBNA2 | RPTELQPTP (SEQ ID NO: 71) | 234-242 | HLA-B55 |
| EBNA3A | QAKWRLQTL (SEQ ID NO: 72) | 158-166 | HLA-B8 |
| EBNA3A | AYSSWMYSY (SEQ ID NO: 73) | 176-184 | HLA-A30 |
| EBNA3A | RYSIFFDY (SEQ ID NO: 74) | 246-253 | HLA-A24 |
| EBNA3A | FLRGRAYGL (SEQ ID NO: 75) | 325-333 | HLA-B8 |
| EBNA3A | KRPPIFIRRL (SEQ ID NO: 76) | 378-387 | HLA-B27 |
| EBNA3A | RPPIFIRRL (SEQ ID NO: 77) | 379-387 | HLA-B7 |
| EBNA3A | LEKARGSTY (SEQ ID NO: 78) | 406-414 | HLA-B62 |
| EBNA3A | HLAAQGMAY (SEQ ID NO: 79) | 450-458 | HLA-A1 |
| EBNA3A | YPLHEQHGM (SEQ ID NO: 80) | 458-466 | HLA-B35 |
| EBNA3A | VFSDGRVAC (SEQ ID NO: 81) | 491-499 | HLA-A29 |
| EBNA3A | VPAPAGPIV (SEQ ID NO: 82) | 502-510 | HLA-B7 |
| EBNA3A | SVRDRLARL (SEQ ID NO: 83) | 596-604 | HLA-A2 |
| EBNA3A | RLRAEAQVK (SEQ ID NO: 84) | 603-611 | HLA-A3 |

TABLE 2-continued

Exempla T-Cell Epitope

| Peptide from | Sequence | Position | HLA Type |
|---|---|---|---|
| EBNA3A | VQPPQLTQV (SEQ ID NO: 85) | 617-625 | HLA-B46 |
| EBNA3B | HRCQAIRKK (SEQ ID NO: 86) | 149-157 | HLA-B27 |
| EBNA3B | TYSAGIVQI (SEQ ID NO: 87) | 217-225 | HLA-A24 |
| EBNA3B | RRARSLSAERY (SEQ ID NO: 88) | 244-254 | HLA-B27 |
| EBNA3B | VSFIEFVGW (SEQ ID NO: 89) | 279-287 | HLA-B58 |
| EBNA3B | AVFDRKSDAK (SEQ ID NO: 90) | 399-408 | HLA-A11 |
| EBNA3B | IVTDFSVIK (SEQ ID NO: 91) | 416-424 | HLA-A11 |
| EBNA3B | AVLLHEESM (SEQ ID NO: 92) | 488-496 | HLA-B35.01 |
| EBNA3B | VEITPYKPTW (SEQ ID NO: 93) | 657-666 | HLA-B44 |
| EBNA3C | EGGVGWRHW (SEQ ID NO: 94) | 163-171 | HLA-B44 |
| EBNA3C | QNGALAINTF (SEQ ID NO: 95) | 213-222 | HLA-B62 |
| EBNA3C | LRGKWQRRYR (SEQ ID NO: 96) | 249-258 | HLA-B27 |
| EBNA3C | RRIYDLIEL (SEQ ID NO: 97) | 258-266 | HLA-B27 |
| EBNA3C | HHIWQNLL (SEQ ID NO: 98) | 271-278 | HLA-B39 |
| EBNA3C | EENLLDFVRF (SEQ ID NO: 99) | 281-290 | HLA-B44 |
| EBNA3C | LLDFVRFMGV (SEQ ID NO: 100) | 284-293 | HLA-A2 |
| EBNA3C | LDFVRFMGV (SEQ ID NO: 101) | 285-293 | HLA-B37 |
| EBNA3C | KEHVIQNAF (SEQ ID NO: 102) | 335-343 | HLA-B44 |
| EBNA3C | FRKAQIQGL (SEQ ID NO: 103) | 343-351 | HLA-B27 |
| EBNA3C | QPRAPIRPI (SEQ ID NO: 104) | 881-889 | HLA-B7 |
| EBNA-LP | SLREWLLRI (SEQ ID NO: 105) | 284-292 | HLA-A2 (A*0203) |
| LMP1 | FWLYIVMSD (SEQ ID NO: 106) | 38-46 | MHC Class I |
| LMP1 | FRRDLLCPLGA (SEQ ID NO: 107) | 72-82 | HLA-B40 |
| LMP1 | YLLEMLWRL (SEQ ID NO: 108) | 125-133 | HLA-A2 |
| LMP1 | YLQQNWWTL (SEQ ID NO: 109) | 159-167 | HLA-A2 |
| LMP1 | TLLVDLLWL (SEQ ID NO: 110) | 166-174 | HLA-A2 |
| LMP1 | DPHGPVQLSYYD (SEQ ID NO: 111) | 375-386 | HLA-B51 |
| LMP2 | MGSLEMVPM (SEQ ID NO: 112) | 1-9 | HLA-B35 |
| LMP2 | EDPYWGNGDRHS DYQ (SEQ ID NO: 113) | 61-75 | MHC Class I |
| LMP2 | NPVCLPVIVAPYLF (SEQ ID NO: 114) | 121-134 | MHC Class I |
| LMP2 | LPVIVAPYL (SEQ ID NO: 115) | 125-133 | HLA-B53 |
| LMP2 | PYLFWLAAI (SEQ ID NO: 116) | 131-139 | HLA-A23 |
| LMP2 | ASCFTASVSTVVTA (SEQ ID NO: 117) | 141-154 | WIC Class I |
| LMP2 | FTASVSTVV (SEQ ID NO: 118) | 144-152 | HLA-A68 |
| LMP2 | IEDPPFNSL (SEQ ID NO: 119) | 200-208 | HLA-B40 |
| LMP2 | RRRWRRLTV (SEQ ID NO: 120) | 236-244 | HLA-B27 |
| LMP2 | RRWRRLTVC (SEQ ID NO: 121) | 237-245 | HLA-B14 |
| LMP2 | RRLTVCGGIMF (SEQ ID NO: 122) | 240-250 | HLA-B27 |
| LMP2 | TVCGGIMFL (SEQ ID NO: 123) | 243-251 | HLA-A1 |
| LMP2 | MFLACVLVLIVDAV (SEQ ID NO: 124) | 249-262 | MHC Class I |
| LMP2 | LIVDAVLQL (SEQ ID NO: 125) | 257-265 | HLA-A2 |
| LMP2 | GLGTLGAAI (SEQ ID NO: 126) | 293-301 | HLA-A2 |
| LMP2 | LLWTLVVLL (SEQ ID NO: 127) | 329-337 | HLA-A2 |
| LMP2 | SSCSSCPLSKI (SEQ ID NO: 128) | 340-350 | HLA-A11 |
| LMP2 | ILLARLFLY (SEQ ID NO: 129) | 349-358 | HLA-A29 |
| LMP2 | FLYALALLL (SEQ ID NO: 130) | 356-364 | HLA-A2 |
| LMP2 | TYGPVFMCL (SEQ ID NO: 131) | 419-427 | HLA-A24 |
| LMP2 | CLGGLLTMV (SEQ ID NO: 132) | 426-434 | HLA-A2 |
| LMP2 | VMSNTLLSAW (SEQ ID NO: 133) | 442-451 | HLA-A25 |
| LMP2 | LTAGFLIFL (SEQ ID NO: 134) | 453-461 | HLA-A2 |
| LMP2 | LLSAWILTA (SEQ ID NO: 135) | 447-455 | HLA-A2 |
| BRLF1 | LVSDYCNVLNKEFT (SEQ ID NO: 136) | 25-39 | MHC Class I |
| BRLF1 | LVSDYCNVL (SEQ ID NO: 137) | 25-33 | HLA-A2 |
| BRLF1 | DYCNVLNKEF (SEQ ID NO: 138) | 28-37 | HLA-A24 |
| BRLF1 | AENAGNDAC (SEQ ID NO: 139) | 91-99 | HLA-B45 |
| BRLF1 | IACPIVMRYYVLDHLI (SEQ ID NO: 140) | 101-115 | HLA-A24/C2 |
| BRLF1 | YVLDHLIVV (SEQ ID NO: 141) | 109-117 | HLA-A2 |
| BRLF1 | FFIQAPSNRVMIPAT (SEQ ID NO: 142) | 121-135 | MHC Class I |
| BRLF1 | ATIGTAMYK (SEQ ID NO: 143) | 134-142 | HLA-A11 |
| BRLF1 | KHSRVRAYTYSKVLG (SEQ ID NO: 144) | 145-159 | HLA-A3 |
| BRLF1 | RALIKTLPRASYSSH (SEQ ID NO: 145) | 225-239 | HLA-A2 |

TABLE 2-continued

Exempla T-Cell Epitope

| Peptide from | Sequence | Position | HLA Type |
|---|---|---|---|
| BRLF1 | ERPIFPHPSKPTFLP (SEQ ID NO: 146) | 393-407 | HLA-C4 |
| BRLF1 | QKEEAAICGQMDLS (SEQ ID NO: 147) | 529-543 | HLA-B61 |
| BRLF1 | EVCQPKRIRPFHPPG (SEQ ID NO: 148) | 441-455 | MHC Class I |
| BZLF1 | LPEPLPQGQLTAY (SEQ ID NO: 149) | 52-64 | MHC Class I |
| BZLF1 | EPLPQGQLTAY (SEQ ID NO: 150) | 54-63 | HLA-B35 |
| BZLF1 | APENAYQAY (SEQ ID NO: 151) | 81-89 | HLA-B35 |
| BZLF1 | LQHYREVAA (SEQ ID NO: 152) | 101-115 | HLA-C8 |
| BZLF1 | DSELEIKRYKNR (SEQ ID NO: 153) | 172-183 | HLA-B18 |
| BZLF1 | RKCCRAKFKQLLQHYR (SEQ ID NO: 154) | 186-201 | HLA-C6 |
| BZLF1 | RAKFKQLL (SEQ ID NO: 155) | 190-197 | HLA-B8 |
| BZLF1 | SENDRLRLL (SEQ ID NO: 156) | 209-217 | HLA-B60 |

Influenza A Virus

| Peptide from | Sequence | Position | HLA Type |
|---|---|---|---|
| PR8 | CTELKLSDY (SEQ ID NO: 157) | 44-52 | HLA-A1 |
| PB1 | VSDGGPNLY (SEQ ID NO: 158) | 591-599 | HLA-A1 |
| MP | GILGFVFTL (SEQ ID NO: 159) | 58-66 | HLA-A2 |
| MP | ILGFVFTLTV (SEQ ID NO: 160) | 59-68 | HLA-A2 |
| PR8 | ILRGSVAHK (SEQ ID NO: 161) | 265-274 | HLA-A3 |
| MP | SIIPSGPLK (SEQ ID NO: 162) | 13-21 | HLA-A11 |
| MP1 | RMVLASTTAK (SEQ ID NO: 163) | 178-187 | HLA-A11 |
| MP2 | KSMREEYRK (SEQ ID NO: 164) | 70-78 | HLA-A11 |
| NP | SPIVPSFDM (SEQ ID NO: 165) | 473-481 | HLA-B7 |
| PB1 | QPEWFRNVL (SEQ ID NO: 166) | 329-337 | HLA-B7 |
| NP | SRYWAIRTR (SEQ ID NO: 167) | 383-391 | HLA-B27 |

F. Targeting Moiety

The targeting moiety functions in the TPEC by delivering the TPEC to the local environment of the unwanted cells, enabling a localized treatment strategy. In certain embodiments, the targeting moiety targets the unwanted cells by specifically binding to the unwanted cells. In some instances, the targeting moiety specifically binds the unwanted cells even while the plurality of T-cell epitopes are conjugated to the targeting moiety.

In certain embodiments, the targeting moiety is an antibody or functional part thereof.

Certain antibody targets (with examples of unwanted cell types in parentheses) may include: Her2/Neu (Epithelial malignancies); CD22 (B cells, autoimmune or malignant); EpCAM (CD326) (Epithelial malignancies); EGFR (epithelial malignancies); PMSA (Prostate Carcinoma); CD30 (B cell malignancies); CD20 (B cells, autoimmune, allergic or malignant); CD33 (Myeloid malignancies); membrane lgE (Allergic B cells); lgE Receptor (CD23) (Mast cells or B cells in allergic disease), CD80 (B cells, autoimmune, allergic or malignant); CD86 (B cells, autoimmune, allergic or malignant); CD2 (T cell or NK cell lymphomas); CA125 (multiple cancers including Ovarian carcinoma); Carbonic Anhydrase IX (multiple cancers including Renal Cell Carcinoma); CD70 (B cells, autoimmune, allergic or malignant); CD74 (B cells, autoimmune, allergic or malignant); CD56 (T cell or NK cell lymphomas); CD40 (B cells, autoimmune, allergic or malignant); CD19 (B cells, autoimmune, allergic or malignant); c-met/HGFR (Gastrointestinal tract and hepatic malignancies); TRAIL-R1 (multiple malignancies including ovarian and colorectal carcinoma); DR5 (multiple malignancies including ovarian and colorectal carcinoma); PD-1 (B cells, autoimmune, allergic or malignant); PD1L (Multiple malignancies including epithelial adenocarcinoma); IGF-1R (Most malignancies including epithelial adenocarcinoma); VEGF-R2 (The vasculature associated with the majority of malignancies including epithelial adenocarcinomas; Prostate stem cell antigen (PSCA) (Prostate Adenocarcinoma); MUC1 (Epithelial malignancies); CanAg (tumors such as carcinomas of the colon and pancreas); Mesothelin (many tumors including mesothelioma and ovarian and pancreatic adenocarcinoma); P-cadherin (Epithelial malignancies, including breast adenocarcinoma); Myostatin (GDF8) (many tumors including sarcoma and ovarian and pancreatic adenocarcinoma; Cripto (TDGF1) (Epithelial malignancies including colon, breast, lung, ovarian, and pancreatic cancers); ACVRL 1/ALK1 (multiple malignancies including leukaemias and lymphomas); MUC5AC (Epithelial malignancies, including breast adenocarcinoma); CEACAM (Epithelial malignancies, including breast adenocarcinoma); CD137 (B cells or T cells, autoimmune, allergic or malignant); CXCR4 (B cells or T cells, autoimmune, allergic or malignant); Neuropilin 1 (Epithelial malignancies, including lung cancer); Glypicans (multiple cancers including liver, brain and breast cancers); HERS/EGFR (Epithelial malignancies); PDGFRa (Epithelial malignancies); EphA2 (multiple cancers including neuroblastoma, melanoma, breast cancer, and small cell lung carcinoma); CD38 (Myeloma); CD138 (Myeloma); α4-integrin (AML, myeloma, CLL, and most lymphomas).

In certain modes, antibodies include an anti-epidermal growth factor receptor antibody such as Cetuximab, an anti-Her2 antibody, an anti-CD20 antibody such as Rituximab, an anti-CD22 antibody such as Inotuzumab, G544 or BU59, an anti-CD70 antibody, an anti-CD33 antibody such as hp67.6 or Gemtuzumab, an anti-MUC1 antibody such as GP1.4 and SM3, an anti-CD40 antibody, an anti-CD74 antibody, an anti-P-cadherin antibody, an anti-EpCAM antibody, an anti-CD138 antibody, an anti-E-cadherin antibody, an anti-CEA antibody, an anti FGFR3 antibody, and an anti-α4-integrin antibody such as natalizumab.

G. Cleavage Sites

The cleavage sites function to release the T-cell epitope from the targeting moiety and, in some embodiments, to release the T-cell epitopes from each other. Releasing the T-cell epitopes into single epitopes allows them to most effectively label the unwanted cell for immune attack.

In some instances, the cleavage site may be a separate sequence and in other instances the cleavage site may be integrated into the T-cell epitope such that one sequence serves the function of both elements. This may apply to any of the embodiments described herein and is determined by the selection of the epitope sequences.

The cleavage sites can function in different ways to release the T-cell epitopes in the microenvironment of the unwanted cells. The cleavage may occur inside the unwanted cell or outside the unwanted cell, depending on the strategy employed. If cleavage occurs outside the unwanted cell, the T-cell epitope peptides can be presented without first being internalized into a cell and being engaged in the classical antigen-processing pathways. If cleavage occurs outside the unwanted cell, it may occur in the microenvironment surrounding the cell, including at the cell surface. For example, when the unwanted cell is a cancer cell, the cleavage may occur in the tumor microenvironment (outside of an in the vicinity of the cancer cell), including at the surface of the cancer cell.

In certain embodiments, at least one cleavage site may be cleaved by an enzyme expressed by the unwanted cells. Cancer cells, for instance, are known to express certain enzymes, such as proteases, and these may be employed in the TPEC strategy to cleave the TPEC's cleavage site. By way of nonlimiting example, cathepsin B cleaves FR, FK, VA and VR amongst others; cathepsin D cleaves PRSF-FRLGK (SEQ ID NO: 181), ADAM28 cleaves KPAKFFRL (SEQ ID NO: 182), DPAKFFRL (SEQ ID NO: 183), KPM-KFFRL (SEQ ID NO: 184) and LPAKFFRL (SEQ ID NO: 185); and MMP2 cleaves AIPVSLR (SEQ ID NO: 186).

In some embodiments, at least one cleavage site may be cleaved through a pH-sensitive cleavage reaction inside the unwanted cell. If the TPEC is internalized into the cell, the cleavage reaction may occur inside the cell and may be triggered by a change in pH between the microenvironment outside the unwanted cell and the interior of the cell. Specifically, some cancer types are known to have acidic environments in the interior of the cancer cells. Such an approach may be employed when the interior unwanted cell type has a characteristically different pH from the extracellular microenvironment, such as particularly the glycocalyx. Because pH cleavage can occur in all cells in the lysozymes, selection of a targeting agent when using a pH-sensitive cleavage site may require, when desired, more specificity. For example, when a pH-sensitive cleavage site is used, a targeting agent that binds only or highly preferably to cancer cells may be desired (such as, for example, an antibody binding to mesothelin for treatment of lung cancer).

In certain embodiments, at least one cleavage site may be cleaved by a complement-dependent cleavage reaction. Once TPECs bind to the unwanted cell, the patient's complement cascade may be triggered. In such a case, the complement cascade may also be used to cleave the T-cell epitope from the targeting agent by using a cleavage site sensitive to a complement protease. For example, C1r and C1s and the C3 convertases (C4B,2a and C3b,Bb) are serine proteases. C3/C5 and C5 are also complement proteases Mannose-associated binding proteins (RASP), serine proteases also involved in the complement cascade and responsible for cleaving C4 and C2 into C4b2b (a C3 convertase) may also be used. For example, and without limitation, C1s cleaves YLGRSYKV (SEQ ID NO: 177) and MQLGRX (SEQ ID NO: 178). MASP2 is believed to cleave SLGRKIQI (SEQ ID NO: 179). Complement component C2a and complement factor Bb are believed to cleave GLARSNLDE (SEQ ID NO: 180).

In some embodiments, at least one cleavage site may be cleaved by a protease that is colocalized to the unwanted cell by a targeting moiety that is the same or different from the targeting moiety in the TPEC. For example, any protease may be simultaneously directed to the microenvironment of the unwanted cells by conjugating the protease to a targeting agent that delivers the protease to that location. The targeting agent may be any targeting agent described herein. The protease may be affixed to the targeting agent through a peptide or chemical linker and may maintain sufficient enzymatic activity when bound to the targeting agent.

In some embodiments, the TPEC has a plurality of cleavage sites that are the same. In other embodiments, the TPEC has a plurality of cleavage sites that are not all identical, either in sequence and/or in type, as described above.

H. Preparation of the T-Cell Epitopes and Cleavage Sites

1. Preparation of Individual T-Cell Epitopes and Cleavage Sites to be Separately Conjugated to Targeting Agent Individual T-cell epitopes conjugated to cleavage sites may be prepared through standard peptide synthesis chemistry, such as by coupling the carboxyl group of the incoming amino acid to the N-terminus of the growing peptide chain using a N-terminal protecting group addition strategy, such as tert-butoxycaronyl (Boc) and 9-fluorenylmethoxycarbonyl (Fmoc), with their respective deprotection agents TFA and piperidine. Peptide synthesis may occur by hand or in an automated machine. Alternatively, services may be employed that prepare peptides upon order.

2. Preparation of Linear Polytopes

Polytopes up to ~50 amino acids could be made by standard peptide synthesis. This would allow up to about 5 epitopes to be incorporated into the polytope. In instances where more epitopes in the polytope are desired, or when human protein domains flank the epitopes in the polytope, then recombinant production of the polytope may occur. The DNA sequence for the polytope would be incorporated into a vector that would allow a cell line such as Chinese hamster ovary (CHO) cells to express the protein. The protein would be secreted by the cell line and could be purified from the cell culture supernatant. The purified polytope could then be conjugated to a targeting moiety through a chemical linker, as described herein. In another embodiment, nucleic acids encoding the polytope could be added on to an end of the DNA sequence encoding the targeting moiety to make one continuous polypeptide chain incorporating the targeting moiety and polytope. This could then be expressed in a cell line in the same way as the previous embodiment.

3. Preparation of Branched Polytope

Branched polytopes, such as shown in FIG. 2C, may also be prepared. Individual T-cell epitopes to be applied to a branched polytope may be prepared according to Section I.H.1 before being conjugated to a connecting stem. In some embodiments, the connecting stem may be comprised of amino acids and may be a peptide stem.

The peptide stem may comprise amino acids that have a reactive property that can be targeted by crosslinking reagents. In some embodiments, cysteine and lysine may be used as there are a large number of crosslinking reagents that may be used at these amino acids. In one embodiment, a connecting stem may be a peptide comprising a large number of lysine or cysteine residues to facilitate linking reactions by sulfo-SMCC, for example. In another embodiment, the connecting stem may comprise serine or threonine, so as to partner with a crosslinking agent that would link to hydroxyl groups on these amino acids.

In another embodiment, spacer amino acids may be used in between those that have a reactive property to the cross-linking reagents in order to allow for protease attack without being blocked by other peptides bound to the stem. In certain aspects, a basic spacer may include glycine and serine. In some embodiments, the incorporation of proline between reactive amino acids may be useful as proline induces a slight rotation of the peptide which may help to keep the protease cleavable peptides bound to the stem further apart.

In certain embodiments, the peptide stem may comprise from about 10 to 80, 20 to 80, or 40 to 80 amino acids. In one embodiment the peptide stem comprises from about 2 to 20 amino acids that are bound to a T-cell epitope and cleavage site.

The individual T-cell epitopes may be conjugated to the peptide stem using the chemical linker technology discussed in Section I.I below. The connecting stem comprising the individual T-cell epitopes may also be conjugated to the targeting moiety using the chemical linker technology discussed in Section I.I below. In some embodiments, a different chemical linker may be chosen for these two conjugations so as to have additional control over the conjugation process. In one embodiment, T-cell epitopes may be affixed to the connecting stem by sulfo-SMCC and the connecting stem comprising the T-cell epitopes to the targeting moiety by 3-MPA, for example.

I. Method of Conjugation to the Targeting Moiety

Different approaches may be employed to conjugate the cleavage site(s) and plurality of T-cell epitopes (whether as separate T-cell epitope and cleavage site pairs or whether as a polytope) to the targeting agent. In some aspects, a polytope comprising a plurality of cleavage sites and a plurality of T-cell epitopes are conjugated to the targeting agent using at least one peptide bond. In certain aspects, the conjugation occurs through at least one bond other than a peptide bond. Such a conjugation may be through a chemical linker A nonpeptide bond, such as using a chemical linker, may be employed for separately conjugated pairs of T-cell epitopes and cleavage sites or for polytopes.

In some instances, a chemical linker may be a heterobifunctional crosslinking reagent. Heterobifunctional crosslinking reagents covalently bind two proteins together by targeting different functional groups on separate proteins. The amine-to-sulphydryl crosslinking reagents contain an NHS-ester at one end of the reagent, which binds to free amine groups on a first protein/pep tide, predominantly on the amino acid lysine. At the other end of the reagent, a maleimide group binds to sulphydryl group of a second protein/peptide, which can be found on the amino acid cysteine. Examples of amine-to-sulphydryl crosslinking reagents may include (a) sulfosuccinimidyl-4-(N-maleimidomethyl)cyclohexane-1-carboxylate (Sulfo-SMCC, which is soluble in water) or succinimidyl-4-(N-maleimidomethyl) cyclohexane-1-carboxylate (SMCC, which has poor water solubility), (b) succinimidyl 4-(p-maleimidophenyl)butyrate (SMPB), (c) succinimidyl 6-[(beta-maleimidopropionamido)hexanoate] (SMPH); and (d) Sulfosuccinimidyl 6-(3'-[2-pyridyldithio]-propionamido) hexanoate (Sulfo-LC-SPDP); or (e) maleimide such as 3-maleimidopropionic acid.

Alternatively, another class of cross-linking reagents are the sulphydryl-to-carbohydrate reagents, which contain a maleimide group at one end and a hydrazide group at the other end. The maleimide group binds to a free sulphydryl on a first protein/peptide, such as that found on the amino acid cysteine, and the hydrazide group binds to an aldehyde group formed from an oxidized carbohydrate on a second protein/peptide. This family of reagents includes (a) 3,3'-N-[ε-Maleimidocaproic acid] hydrazide, trifluoroacetic acid salt (EMCH) and (b)N-beta-Maleimidopropionic acid hydrazide-trifluoroacetic acid (BMPH).

A third group of heterobifunctional cross-linking reagents are the photocleavable reagents including sulfosuccinimidyl 2-([4,4'-azipentanamido]ethyl)-1,3'-dithiopropionate (SDAD). These reagents have an NHS-ester at one end linking to free amines (lysine) and a diazrine group at the other end which can react with any amino acid side chain or peptide backbone upon activation with long-wave ultra violet light (330-370 nm) There are many other reagents from these groups and from other cross-linking groups that can be used in this technology.

J. Inclusion of Human Protein Domains

In certain embodiments, the T-cell epitopes are flanked on one or both ends by at least one human protein domain. In some embodiments, the cleavage sites reside between the T-cell epitopes and the human protein domains.

Various human protein domains may be used in this manner. For example, at least one human protein domain may be a beta barrel or a coiled coil. In some embodiments, the human protein may be a FN3 (Fibronectin type III) domain. In some embodiments, the human protein may be beta-sandwich, Lipocalin, EETI-II/AGRP, Kunitz domain (BPTI), Thioredoxin, Protein A, Ankyrin, gamma-B-crystallin/ubiquitin, CTLD3/Tetranexin, or and LDLR-A In some embodiments, the human protein may be human serum albumin, immunoglobulin CH2 domain, or camelid VHH domain.

In certain instances, a human protein domain may be a CL, CH2, and/or CH3 domain. For example, a T-cell epitope or plurality of T-cell epitopes may be flanked by CH2 sequences. Such CH2 sequences may be within the CH2 domain of an antibody or functional part serving as the targeting moiety. Such CH2 sequences may also be an additional CH2 domain distinct from the targeting moiety. In some embodiments, such as shown in FIG. 2B, framework regions may be employed in a polytope to give additional three dimensional organization to the polytope.

In some aspects, the human protein domain is not a human immunoglobulin protein domain.

In some aspects, the human protein domain displays the T-cell epitopes on its three-dimensional surface.

II. Pharmaceutical Compositions

The TPECs may be employed as pharmaceutical compositions. As such, they may be prepared along with a pharmaceutically acceptable carrier. If parenteral administration is desired, for instance, the TPECs may be provided in sterile, pyrogen-free water for injection or sterile, pyrogen-free saline. Alternatively, the TPECs may be provided in lyophilized form for resuspension with the addition of a sterile liquid carrier.

III. Methods of Treatment A. Reduction of Unwanted Cells, Retargeting of Immune Response, and Treatment of Cancer The TPECs described herein may be used in a method of treating a disease in a patient characterized by the presence of unwanted cells comprising administering a TPEC composition to the patient. This may include both treating and preventing a disorder. Additionally, the TPECs described herein may also be used in a method of retargeting (i.e., redirecting) a patient's own immune response to unwanted cells comprising administering a TPEC composition to the patient.

The amount of the agent administered to the patient may be chosen by the patient's physician so as to provide an effective amount to treat the condition in question.

The patient receiving treatment may be a human. The patient may be a primate or any mammal. Alternatively, the patient may be an animal, such as a domesticated animal (for example, a dog or cat), a laboratory animal (for example, a laboratory rodent, such as a mouse, rat, or rabbit), or an animal important in agriculture (such as horses, cattle, sheep, or goats).

The condition characterized by unwanted cells may include cancer. The cancer may be a solid or non-solid malignancy. The cancer may be any cancer such as breast cancer, ovarian cancer, endometrial cancer, cervical cancer, bladder cancer, renal cancer, melanoma, lung cancer, prostate cancer, testicular cancer, thyroid cancer, brain cancer, oesophageal cancer, gastric cancer, pancreatic cancer, colorectal cancer, liver cancer, leukaemia, myeloma, nonHodgkin's lymphoma, Hodgkin's lymphoma, acute myeloid leukaemia, acute lymphoblastic leukaemia, chronic lymphoblastic leukaemia, lymphoproliferative disorder, myelodysplastic disorder, myeloproliferative disease and premalignant disease.

The condition characterized by unwanted cells may also include an allergic or autoimmune disease. For instance, autoimmune diseases may include Addison's disease, celiac disease, dermatomyositis, Graves' disease, Hashimoto's thyroiditis, multiple sclerosis, myasthenia gravis, pernicious anemia, reactive arthritis, rheumatoid arthritis, Sjogren syndrome, and systemic lupus erythematosus.

The TPECs may be administered alone or in conjunction with other forms of therapy, including surgery, radiation, or traditional chemotherapy. In some embodiments, the activity of the TPECs may also be enhanced by boosting the patient's immune response against one or more of the T-cell epitopes used, such as by vaccinating the subject with the T-cell epitope or by administering immunostimulatory agents.

In some embodiments, the patient receives multiple doses of the composition over at least 30, 45, 60, 75, 90, 120, 150, or more days, or on an ongoing basis. In certain modes the patient receives multiple doses of the composition over at least 1, 2, 3, 4, 5, 6, 7, 8, 9, 10, 11, or 12 months, or on an ongoing basis. If approaches are employed to reduce the patient's immune response against the TPEC itself, additional benefits may be achieved by administering the composition to a patient in relapse who received the composition for an earlier round of therapy.

B. Reduction of Immune Response Against TPEC Itself

In certain aspects described herein, having multiple copies of the same T-cell epitope increases an immune response against the unwanted cell when the agent is administered to a patient and having a diversity of T-cell epitopes assures effectiveness across a wide variety of patients from different racial and ethnic groups. Nevertheless, if a physician desires to use a TPEC therapy over a continued period of time, optional steps may be taken to reduce the patient's own immune response against the TPEC itself.

In certain embodiments, the arrangement or composition of T-cell epitopes on the TPEC are random in nature. For example, if a mixture of T-cell epitopes are conjugated using a chemical linker to the targeting moiety, different combinations of T-cell epitopes may affix to the targeting moieties. This makes it significantly more difficult for the patient to mount an immune response against the TPECs themselves. Even in instances where the plurality of T-cell epitopes are the same, affixing them separately to the targeting moiety through a chemical linker may also result in a random placement of the T-cell epitopes along the targeting moiety, likewise damping the patient's own immune response against the TPEC.

Such approaches may ensure that the patient does not develop an immune response against the TPEC composition sufficient to inactivate the TPEC composition upon subsequent administrations, meaning that no more than about 0%, 10%, 20%, 30%, 40%, 50%, 60%, 70%, 80%, or 90% of the composition is inactivated by the patient's own antibodies to the TPEC.

Immunogenicity of a composition may be measured in an ELISA assay using human serum. For example, test compositions may be immobilized on a 96-well plate, blocked and diluted serum samples incubated for 1 hour. Antibodies against the test composition present in the human sera may bind to the test compositions on the plate. Biotinylated test agent or a biotinylated secondary antibody such as an anti-human IgG/IgA/IgM in combination with streptavidin-HRP and TMB could be used to generate a signal.

The present compositions are expected to be at least about 10%, 20%, 30%, 40%, 50%, 60%, 70%, 80%, or 90% less immunogenic than prior compositions.

EXAMPLES

Example 1

Preparation of T-cell Epitopes and Cleavage Sites

Peptides comprising T-cell epitopes and cleavage sites were ordered from external companies who synthesized them in standard solid phase peptide synthesis. The peptides were dissolved in DMSO to a final concentration of 10 mg/ml to be used for conjugation.

Example 2

Standard Operating Protocol for Conjugation of Polytope Using Sulfo-SMCC

The following procedure was used as a standard-operating protocol for conjugation of polytope peptide (comprising a plurality of T-cell epitopes and cleavage sites) to an antibody serving as a targeting moiety by using sulfo-SMCC.

1. Cysteinylated peptides dissolved in DMSO to final concentration of 10 mg/ml.

2. Weigh 1 mg Sulfosuccinimidyl 4-[N-maleimidomethyl]cyclohexane-1-carboxylate (Sulfo-SMCC) and dissolve in 200 µl phosphate buffered saline (PBS) (final concentration 5 mg/ml).

3. Add 100 µl antibody (10 mg/ml, 1 mg antibody) to 10 µl dissolved Sulfo-SMCC (5 mg/ml) and incubate at room temperature for 30 minutes.

4. Wash a ZebaSpin desalting column (Pierce) by firstly spinning the column at 1500 g for 60 seconds to remove the ethanol (storage buffer).

5. Add 300 µl PBS and spin at 1500 g for 60 seconds. Remove eluate and repeat a further three times.

6. Add up to 125 µl antibody-SMCC to each column, and centrifuge at 1500 g for 120 seconds, collecting the eluate.

7. To 100 µl antibody-SMCC conjugate, add 3 µl cysteinylated peptide (10 mg/ml) and incubate at room temperature for 30 minutes.

8. Wash a Protein A column (GE Healthcare) by firstly spinning the column at 100 g for 30 seconds to remove the ethanol (storage buffer).

9. Add 500 µl PBS and spin at 100 g for 30 seconds. Remove eluate and repeat a further two times.

10. Dilute antibody-peptide conjugate to 500 µl in PBS and add it to the protein A column, mixing the antibody with the beads. Leave at room temperature for 20 minutes, shaking.

11. Spin the column at 100 g and remove the eluate, the antibody-peptide complex should still be coupled to the beads.

12. Wash the column by adding 500 µl PBS and mixing the beads well before spinning at 100 g for 30 seconds and removing eluate. Repeat this step a further three times.

13. To elute the bound antibody, add 200 µl 0.1M citric acid to the beads and incubate for 5 minutes at room temperature. Place column in a 2 ml eppendorf containing 25 µl 1M Tris pH9 and spin at 100 g for 30 seconds; collect eluate.

14. Optionally repeat step 13.

15. Store antibody-peptide complex at 4° C.

Example 3

Standard Operating Protocol for Production of a TPEC Comprising Separately-conjugated Epitopes Using Sulfo-SMCC The following procedure was used as a standard-operating protocol for separately conjugating a plurality of T-cell epitopes and their corresponding cleavage sites to an antibody serving as a targeting moiety by using sulfo-SMCC.

1. Cysteinylated peptides dissolved in DMSO to final concentration of 10 mg/ml.

2. Weigh 1 mg Sulfosuccinimidyl 4-[N-maleimidomethyl]cyclohexane-1-carboxylate (Sulfo-SMCC) and dissolve in 200 µl phosphate buffered saline (PBS) (final concentration 5 mg/ml).

3. Add 100 µl antibody (10 mg/ml, 1 mg antibody) to 10 µl dissolved Sulfo-SMCC (5 mg/ml) and incubate at room temperature for 30 minutes.

4. Wash a ZebaSpin desalting column (Pierce) by firstly spinning the column at 1500 g for 60 seconds to remove the ethanol (storage buffer).

5. Add 300 µl PBS and spin at 1500 g for 60 seconds. Remove eluate and repeat a further three times.

6. Add up to 125 µl antibody-SMCC to each column, and centrifuge at 1500 g for 120 seconds, collecting the eluate.

7. Generate a mixture or required peptides in a tube so that there is a total of 30 µg of total peptide. Add the peptide mixture to 100 µl of antibody-SMCC complex and leave at room temperature for 30 minutes.

8. Wash a Protein A column (GE Healthcare) by firstly spinning the column at 100 g for 30 seconds to remove the ethanol (storage buffer).

9. Add 500 µl PBS and spin at 100 g for 30 seconds. Remove eluate and repeat a further two times.

10. Dilute antibody-peptide conjugate to 500 µl in PBS and add it to the protein A column, mixing the antibody with the beads. Leave at room temperature for 20 minutes, shaking.

11. Spin the column at 100 g and remove the eluate, the antibody-peptide complex should still be coupled to the beads.

12. Wash the column by adding 500 µl PBS and mixing the beads well before spinning at 100 g for 30 seconds and removing eluate. Repeat this step a further three times.

13. To elute the bound antibody, add 200 µl 0.1M citric acid to the beads and incubate for 5 minutes at room temperature. Place column in a 2 ml eppendorf containing 25 µl 1M Tris pH9 and spin at 100 g for 30 seconds; collect eluate.

14. Optionally repeat step 13.

15. Store antibody-peptide complex at 4° C.

Example 4

Standard Operating Protocol for Production of Polytope TPEC Using 3-maleimidopropionic Acid Linked Peptide The following procedure was used as a standard-operating protocol for separately conjugating a polytope to an antibody serving as a targeting moiety by using 3-MPA.

1. 3-maleimidopropioinc acid linked peptides dissolved in DMSO to final concentration of 10 mg/ml.

2. To 100 µl antibody (diluted in PBS if required), add 3 µl polytope peptide (10 mg/ml) and incubate at room temperature for 30 minutes.

3. Wash a Protein A column (GE Healthcare) by firstly spinning the column at 100 g for 30 seconds to remove the ethanol (storage buffer).

4. Add 500 µl PBS and spin at 100 g for 30 seconds. Remove eluate and repeat a further two times.

5. Dilute antibody-peptide conjugate to 500 µl in PBS and add it to the protein A column, mixing the antibody with the beads. Leave at room temperature for 20 minutes, shaking.

6. Spin the column at 100 g and remove the eluate, the antibody-peptide complex should still be coupled to the beads.

7. Wash the column by adding 500 µl PBS and mixing the beads well before spinning at 100 g for 30 seconds and removing eluate. Repeat this step a further three times.

8. To elute the bound antibody, add 200 µl 0.1M citric acid to the beads and incubate for 5 minutes at room temperature. Place column in a 2 ml eppendorf containing 25 µl 1M Tris pH9 and spin at 100 g for 30 seconds; collect eluate.

9. Optionally repeat step 8.

10. Store antibody-peptide complex at 4° C.

Example 5

Standard Operating Protocol for Production of a TPEC Comprising Separately-Conjugated Epitopes Using 3-maleimidopropionic Acid Linked Peptide The following procedure was used as a standard-operating protocol for separately conjugating a plurality of T-cell epitopes and their corresponding cleavage sites to an antibody serving as a targeting moiety by using 3-MPA.

1. 3-maleimidopropioinc acid linked peptides dissolved in DMSO to final concentration of 10 mg/ml.

2. Generate a mixture or required peptides in a tube so that there is a total of 30 µg of total peptide, add to 100 µl of antibody (diluted in PBS if required) and incubate at room temperature for 30 minutes.

3. Wash a Protein A column (GE Healthcare) by firstly spinning the column at 100 g for 30 seconds to remove the ethanol (storage buffer).

4. Add 500 µl PBS and spin at 100 g for 30 seconds. Remove eluate and repeat a further two times.

5. Dilute antibody-peptide conjugate to 500 µl in PBS and add it to the protein A column, mixing the antibody with the beads. Leave at room temperature for 20 minutes, shaking.

6. Spin the column at 100 g and remove the eluate, the antibody-peptide complex should still be coupled to the beads.

7. Wash the column by adding 500 µl PBS and mixing the beads well before spinning at 100 g for 30 seconds and removing eluate. Repeat this step a further three times.

8. To elute the bound antibody, add 200 µl 0.1M citric acid to the beads and incubate for 5 minutes at room temperature. Place column in a 2 ml eppendorf containing 25 µl 1M Tris pH9 and spin at 100 g for 30 seconds; collect eluate.

Optionally repeat step 8.

Store antibody-peptide complex at 4° C.

Example 6

TPEC Compositions Comprising Two Cytomegalovirus Peptides and Evaluation in B-Lymphoblastoid Cells We contacted B-lymphoblastoid cells (B-LCL) with an agent comprising Rituximab conjugated to two different cytomegalovirus peptides NLVPMVATV (SEQ ID NO: 1) and RPHERNGFTVL (SEQ ID NO: 2) each with a cleavage site for cathepsin B. Subsequent exposure to peptide-specific T cells resulted in the generation of a T cell response to the B-LCL.

Rituximab was conjugated with the peptides NLVPMVATVASGV{CIT}GC (SEQ ID NO: 3) and RPHERNGFTVLASGFKGC (SEQ ID NO: 4) at the following ratios from Table 3, wherein CIT represents citrulline, a type of amino acid that is similar to arginine

TABLE 3

Peptide Ratios

| TPEC | NLVPMVATVASGV{CIT}GC (SEQ ID NO: 3) | RPHERNGFTVLASGFKGC (SEQ ID NO: 4) |
|---|---|---|
| 1 | 0% | 100% |
| 2 | 10% | 90% |
| 3 | 20% | 80% |
| 4 | 30% | 70% |
| 5 | 40% | 60% |
| 6 | 50% | 50% |
| 7 | 60% | 40% |
| 8 | 70% | 30% |
| 9 | 80% | 20% |
| 10 | 90% | 10% |
| 11 | 100% | 0% |

After staining the cells with Rituximab conjugated to the mixture of peptides, labeled cells were washed and cultured overnight at 37° C. in the presence of peptide-specific T cells. Supernatant was harvested and assayed for the presence of IFN-γ.

Figure 3B:
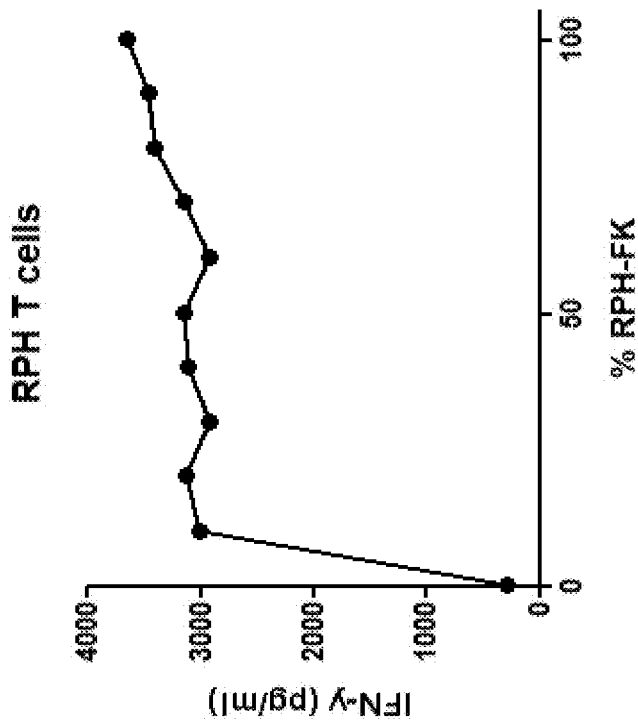
Figure 3A:
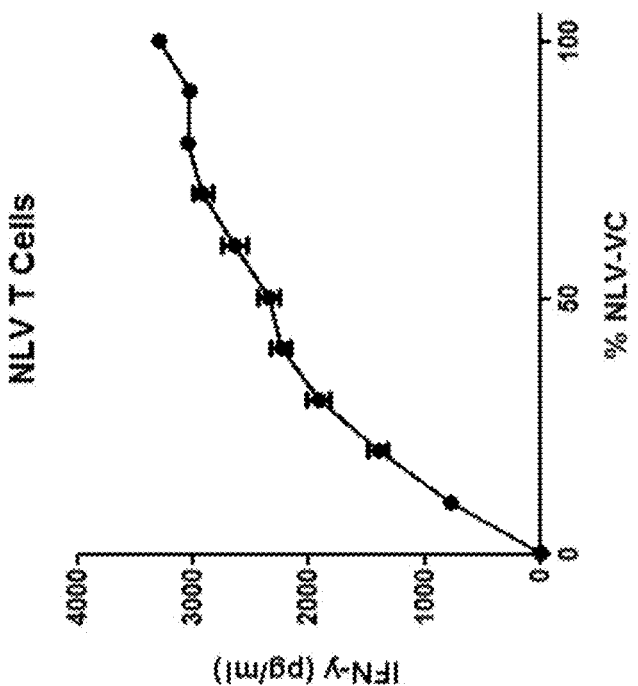
Figure 3C:
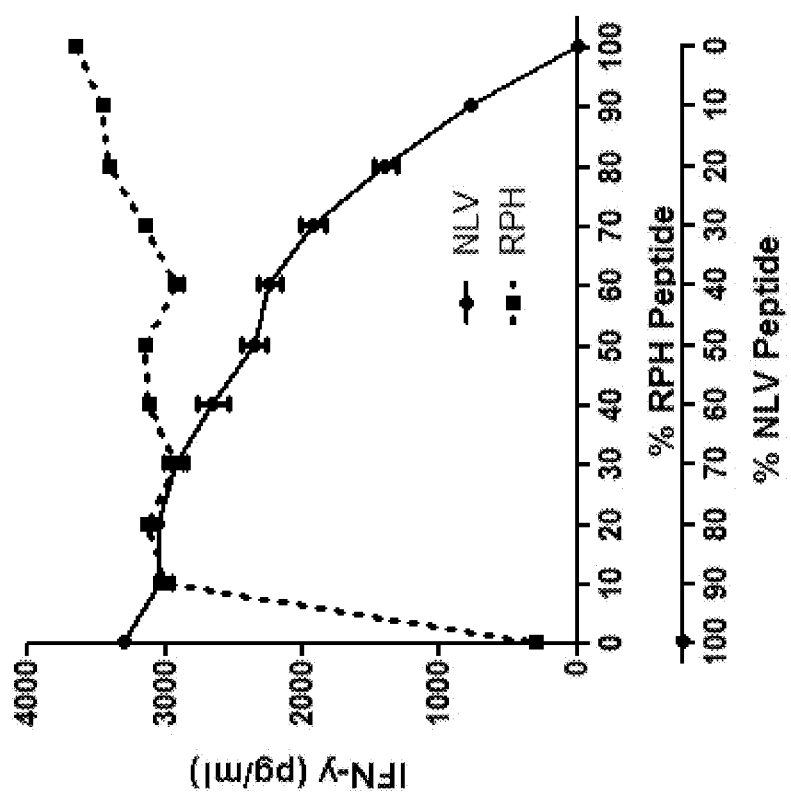

Using NLV-specific T cells, TPEC #11 was recognized strongly as seen by a large production of IFN-γ whereas TPEC #1 is not recognized at all as there was no production of IFN-γ. See FIG. 3A. Conversely, using RPH-specific T cells TPEC #1 was recognized strongly as seen by a large production of IFN-γ whereas TPEC #11 is not recognized at all as there was no production of IFN-γ. See FIG. 3B. There is production of IFN-γ by both NLV- and RPH-specific T cells towards TPEC #2-10, demonstrating the notion that conjugating more than one peptide to the antibody can allow one to engage with more than one specificity of peptide-specific T cell.

Example 7

TPEC Compositions Comprising Three Cytomegalovirus Peptides and Evaluation in B-Lymphoblastoid Cells We contacted B-lymphoblastoid cells (B-LCL) with an agent comprising Rituximab conjugated to three different cytomegalovirus peptides VLEETSVML (SEQ ID NO: 5), BRVLBBYVL (SEQ ID NO: 6) and YILEETSVM (SEQ ID NO: 7) each with a cleavage site for cathepsin B. Subsequent exposure to peptide-specific T cells resulted in the generation of a T cell response to the B-LCL.

Rituximab was conjugated with VLEETSVMLAS-GFKGC (SEQ ID NO: 8), BRVLBBYVLASGFKGC (SEQ ID NO: 9) where B is amino butyric acid, a homolog for cysteine, and YILEETSVMASGFKGC (SEQ ID NO: 10) at equal amounts of peptide. B-LCL cells were labeled with Rituximab TPEC and after incubation, washed to remove excess TPEC. Labeled target cells were incubated overnight at 37° C. in the presence of VLE-specific, CRV-specific or YIL-specific T cells. Supernatant from the cultures was used to assess the presence of IFN-γ.

Figure 4:
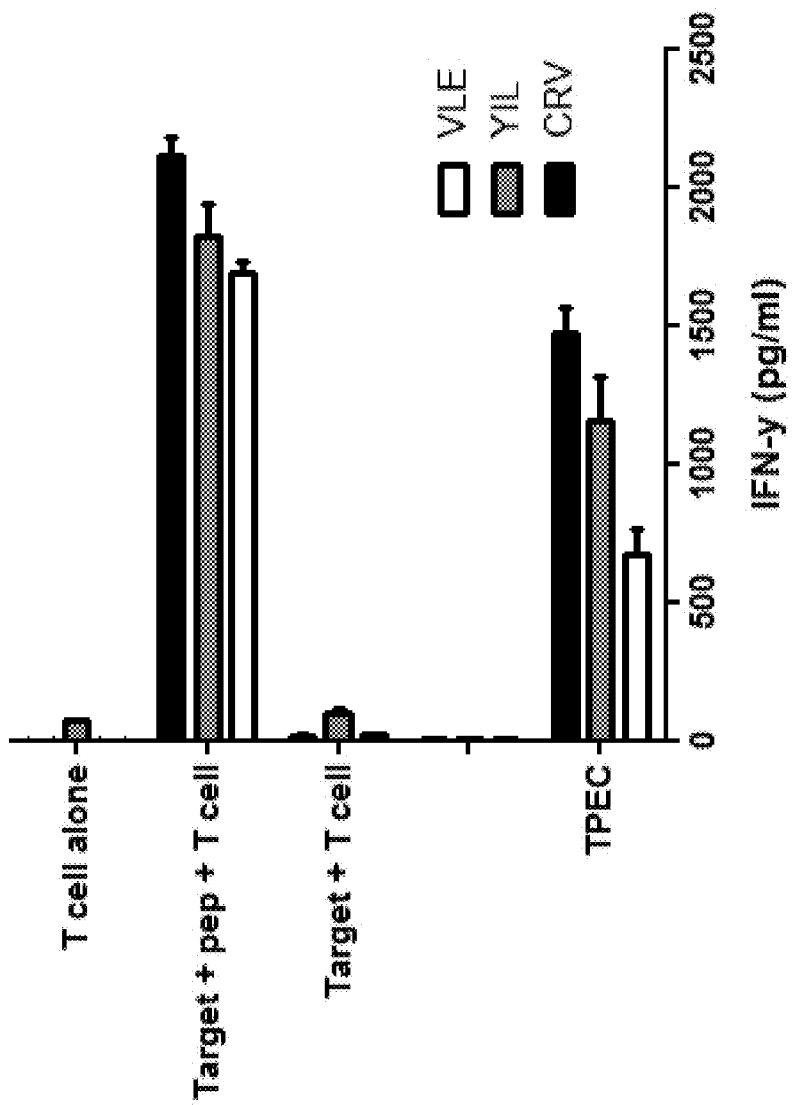

Results are shown in FIG. 4. There was IFN-γ released by all of the different peptide-specific T cells in response to the TPEC-labeled target cells suggesting that each of the three conjugated peptides could be released from the antibody and used to stimulate peptide-specific T cells.

Example 8

TPEC Compositions Comprising a Single Peptide Having Two Different Cytomegalovirus Peptides and Evaluation in B-Lymphoblastoid Cells We contacted B-lymphoblastoid cells (B-LCL) with an agent comprising Rituximab conjugated to a single peptide which comprised two different cytomegalovirus peptides: (i) NLVPMVATV (SEQ ID NO: 1) and RPHERNGFTVL (SEQ ID NO: 2) or (ii) NLVPMVATV (SEQ ID NO: 1) and VLEETSVML (SEQ ID NO: 5) each separated from the other by a cleavage site for cathepsin B. Subsequent exposure to NLV peptide-specific T cells resulted in the generation of a T cell response to the B-LCL.

Rituximab was conjugated with the peptides (i) CGVAN-LVPMVATVAVAVLEETSVML (SEQ ID NO: 11), (ii) CVARPHERNGFTVLVANLVPMVATV (SEQ ID NO: 12) and (iii) CGVANLVPMVATVARPHERNGFTVL (SEQ ID NO: 13). Target cells were labeled with TPEC and washed after incubation to remove excess TPEC. Target cells were cultured overnight at 37° C. in the presence of NLV-specific T cells and the supernatant assayed for the presence of IFN-γ the following day.

NLV-specific T cells were able to recognize target cells labeled with each of the three TPECs tested as determined by IFN-γ release. This demonstrates the ability of a peptide containing more than one cytomegalovirus derived peptide, separated by a protease cleavage site, to stimulate peptide-specific T cells. Furthermore, the position of the NLVPMVATV (SEQ ID NO: 1) peptide in the polytope appears to affect the magnitude of the response with the NLV peptide being furthest from the antibody CVARPHERNGFTVL-VANLVPMVATV (SEQ ID NO: 12) producing the largest response. However, both polytope peptides containing the NLV peptide closest to the antibody CGVANLVPMVATVA-VAVLEETSVML (SEQ ID NO: 11) and CGVANLVPM-VATVARPHERNGFTVL (SEQ ID NO: 13) also demonstrate a T cell response above background.

Results are shown in FIG. 5.

Example 9

Preparation of a TPEC Comprising Polytope Branched Peptide a TPEC Comprising Polytope Branched Peptide was Prepared A stem peptide that contains four azidonorleucine residues was provided along with peptides (branches) that contain propargyl glycine at the amino terminus (FIG. 6A). Each branched peptide has a $NH_2$ cap on the C-terminal end which can aid in peptide serum stability. The sequence of the stem peptide was SEEZSEEZSEEZSEEZ, wherein Z is Azidonorleucine (SEQ ID NO: 168). For Branched TPEC 1, the sequences of the branched peptides were BKPAKF-FRLTPRVTGGGAM-nh$_2$, wherein B is propargyl glycine (SEQ ID NO: 169), BKPAKFFRLRPHERNGFTVL-nh$_2$, wherein B is propargyl glycine (SEQ ID NO: 170), BKPAKFFRLRELRRKMMYM-nh$_2$, wherein B is propargyl glycine (SEQ ID NO: 171), and BKPAKFFRLNLVP-MVATV-nh$_2$, wherein B is propargyl glycine (SEQ ID NO: 172).

And for Branched TPEC 3, the sequences of the branched peptides were BAIPVSLRTPRVTGGGAM-nh$_2$, wherein B is propargyl glycine (SEQ ID NO: 173), BAIPVSLRRPH-ERNGFTVL-nh$_2$, wherein B is propargyl glycine (SEQ ID NO: 174), BAIPVSLRELRRKMMYM-nh$_2$, wherein B is propargyl glycine (SEQ ID NO: 175), and BAIPVSLVTE-HDTLLY-nh$_2$, wherein B is propargyl glycine (SEQ ID NO: 176).

Incubation of equimolar concentrations of the branches with the stem peptide in DMSO in the presence of 10 mg in 4 ml of the $CuSO_4.5H_2O$ catalyst mixed with 10 mg in 4 ml ascorbic acid overnight resulted in the formation of the branched peptide used for conjugation. The final concentration of DMSO for the reaction was 50%. The branched peptides were purified using HPLC and verified using mass spectrometry (FIG. 6B).

The branched peptide was conjugated to either Rituximab or Cetuximab by firstly reducing the antibody in the presence of approximately 0.1 mM (tris(2-carboxyethyl)phosphine (TCEP) for 90 minutes. The branched peptide is then added at 3× the concentration as TCEP for 60 minutes and N-acetyl cysteine is added to quench the free peptide using the same concentration as the branched peptide for 30 minutes. The free peptide is removed using protein A sepahrose beads to bind the TPEC whilst the free peptide is washed off. The TPEC is then collected from the protein A beads by eluting using 0.1M glycine and buffered using 1 m Tris pH8.

Example 10

In Vitro Targeting of a Transformed B Cell Line Using TPEC Comprising Polytope Branched Peptide Two agents comprised of Rituximab conjugated with a branched peptide consisting of four different viral epitopes, each linked to a single stem peptide. In Branched TPEC 1, each of the four peptides was separated from the stem peptide by an ADAM28 protease cleavage sequence. In Branched TPEC 3, each of the four peptides was separated from the stem peptide by an MMP2 cleavage sequence. The target cells were labelled with the Rituximab-TPEC before being incubated with CD8 T cells specific for one of two different viral epitopes. Specifically, TPR T cells were specific for the viral epitope TPRVTGGGAM (SEQ ID NO: 49) and this epitope was present in branches 1-1 and 3-1. RPH T cells were specific for the viral epitope RPHERNG-FTVL (SEQ ID NO: 2) and this epitope was present in branches 1-2 and 3-2.

Upon binding malignant cells (transformed B cell line), viral epitopes were released from the stem peptide by proteolytic cleavage releasing the viral epitopes TPRVTGGGAM (SEQ ID NO: 49), RPHERNGFTVL (SEQ ID NO: 2), ELRRKMMYM (SEQ ID NO: 24) and VTEH-DTLLY (SEQ ID NO: 53). Upon release, the peptides were presented on MHC class I molecules on the malignant cells where they could be recognized by the CD8 T cells. Recognition of malignant cells by the CD8 T cells was measured by release of IFN-γ by the T cells which can be used as a proxy for T cell killing.

Results are shown in FIGS. 7A and 7B. Target lymphoma cells labeled with branched peptide TPEC are recognized by T cells specific for the RPHERNGFTVL (SEQ ID NO: 2) and TPRVTGGGAM (SEQ ID NO: 49) peptides, especially using the Branch 1 TPEC. Untreated target cells were not recognized by the peptide-specific T cells (negative control) whereas free peptide pulsed target cells were strongly recognized by T cells (positive control).

These results demonstrate that branched TPECs can obtain positive results in a widely-recognized model for retargeting a T cell response.

Example 11

In Vitro Targeting of Ovarian Carcinoma Cell Line Using TPEC Comprising Polytope Branched Peptide Two agents comprised of Cetuximab conjugated with a branched peptide consisting of four different viral epitopes, all linked to a single stem peptide was provided. In Branched TPEC 1, each of the four peptides was separated from the stem peptide by an ADAM28 protease cleavage sequence. In Branched TPEC 3, each of the four peptides was separated from the stem peptide by an MMP2 cleavage sequence. The target cells were labelled with the Cetuximab-TPEC before being incubated with CD8 T cells specific for one of two different viral epitopes. Specifically, TPR T cells were specific for the viral epitope TPRVTGGGAM (SEQ ID NO: 49) and this epitope was present in branches 1-1 and 3-1. RPH T cells were specific for the viral epitope RPHERNG-FTVL (SEQ ID NO: 2) and this epitope was present in branches 1-2 and 3-2.

Upon binding malignant cells (ovarian carcinoma cell line), viral epitopes were released from the stem peptide by proteolytic cleavage releasing the viral epitopes TPRVTGGGAM (SEQ ID NO: 49), RPHERNGFTVL (SEQ ID NO: 2), ELRRKMMYM (SEQ ID NO: 24) and VTEHDTLLY (SEQ ID NO: 53). Upon release, the peptides were presented on MHC class I molecules on the malignant cells where they could be recognized by the CD8 T cells. Recognition of malignant cells by the CD8 T cells was measured by release of IFN-γ by the T cells.

Results are shown in FIGS. 8A and 8B. Target lymphoma cells labeled with branched peptide TPEC are recognized by T cells specific for the RPHERNGFTVL (SEQ ID NO: 2) and TPRVTGGGAM (SEQ ID NO: 49) peptides, especially using the Branch 1 TPEC. Untreated target cells were not recognized by the peptide-specific T cells (negative control) whereas free peptide pulsed target cells were strongly recognized by T cells (positive control).

These results demonstrate that branched TPECs can obtain positive results in a widely-recognized model for retargeting a T cell response.

Example 12

In Vitro Targeting of Ovarian Carcinoma Cell Line Using TPEC Containing a Bundled Polytope Domain DNA for an agent comprising Cetuximab containing an additional fibronectin type 3 domain (from fibronectin 1 protein) attached to each heavy chain (depicted in FIG. 2B) was synthesized (FIG. 9A). The fibronectin type 3 domain was mutated at the "BC", "DE" and "FG" loops to contain the viral epitopes TPRVTGGGAM (SEQ ID NO: 49), NLVPMVATV (SEQ ID NO: 1), and VLEETSVML (SEQ ID NO: 5). The viral epitopes were separated from the fibronectin type 3 domain by MMP2 protease cleavage sequences on both sides of the CMV epitope as depicted:

Cetuximab heavy chain--Domain--MMP2--Epitope--MMP2--Domain--MMP2--Epitope--MMP2--Domain--MMP2—Epitope This would allow release of the viral epitopes from the bundled domain and targeting agent (Cetuximab) after proteolytic cleavage by MMP2. The DNA for the bundled domain TPEC was transfected into Expi293 cells and the supernatant harvested 10 days post transfection. The bundled domain TPEC was purified from the supernatant using protein A sepharose beads. The target cells, ovarian carcinoma cell line, were labelled with the purified Cetuximab-TPEC with excess, unbound TPEC washed off. The labelled target cells were then incubated overnight in the presence of NLV-specific T cells.

Upon binding malignant cells (ovarian carcinoma cell line), viral epitopes were released from the additional protein domain by proteolytic cleavage. The released peptides were presented on MHC class I molecules on the malignant cells where they could be recognized by the CD8+ T cells. Recognition of malignant cells by the CD8+ T cells was measured by release of IFN-γ by the T cells.

Results are shown in FIG. 9. Target ovarian carcinoma cells labeled with bundled domain TPEC were recognized by T cells specific for the NLVPMVATV (SEQ ID NO: 1) peptide from four different bundled domain TPEC preparations. Untreated target cells were not recognized by the peptide-specific T cells (negative control) whereas free peptide pulsed target cells were strongly recognized by T cells (positive control).

These results demonstrate that bundled domain TPECs can obtain positive results in a widely-recognized model for retargeting a T cell response.

Example 13

In Vivo Targeting of B Cell Lymphoma Using the Separately Conjugated T-Cell Epitopes (i.e., "Hairbrush") (e.g., Chronic Lymphocytic Leukaemia)

An agent comprising Rituximab or an anti-CD22 antibody is conjugated with a peptide mixture containing equal parts of five different cytomegalovirus-derived peptides each containing a protease cleavage site specific for cathepsin B (i) NLVPMVATVASGV{CIT}GC (SEQ ID NO: 3), (ii) VLEETSVMLASGFKGC (SEQ ID NO: 8), (iii) RPHERNGFTVLASGFKGC (SEQ ID NO: 4), (iv) YILEETSVMASGFKGC (SEQ ID NO: 10) and (v) BRVLBBYVLASGFKGC (SEQ ID NO: 9). The patient is infused with the agent, which targets all B cells, healthy and malignant. Upon binding malignant cells, the agent comes into contact with proteases whereby cleavage of the protease recognition domain releases the T-cell epitopes (i) NLVPMVATV (SEQ ID NO: 1), (ii) VLEETSVML (SEQ ID NO: 5), (iii) RPHERNGFTVL (SEQ ID NO: 2), (iv) YILEETSVM (SEQ ID NO: 7) and (v) BRVLBBYVL (SEQ ID NO: 6), which subsequently bind to HLA molecules on the surface of the malignant B cell. The malignant B cells expressing the T-cell epitopes are targeted by the host immune system for cytolysis by T cells.

Example 14

In Vivo Targeting of B-Cell Lymphoma Using a TPEC Comprising Polytope (e.g., Chronic Lymphocytic Leukaemia)

An agent comprising Rituximab or an anti-CD22 antibody is conjugated with a peptide containing four different cytomegalovirus-derived epitopes (i) CGSFRVTEHDTLLYGSFRRPHERNGFTVLGSFRELKRKMIYMGSFRNLVPMVATV (SEQ ID NO: 14). Each of the four epitopes is separated from the next one by a protease cleavage site specific for cathepsin B in the conformation targeting agent-C-$E_1$-C-$E_2$-C-$E_3$-C-$E_4$ where C is protease cleavage and E is epitope. The patient is infused with the agent, which targets all B cells, healthy and malignant. Upon binding malignant cells, the agent comes into contact with proteases whereby cleavage of the protease recognition domain releases the T-cell epitopes (i) NLVPMVATV (SEQ ID NO: 1), (ii) VTEHDTLLY (SEQ ID NO: 53), RPHERNGFTVL (SEQ ID NO: 2), and (iv) ELKRKMIYM (SEQ ID NO: 23), which subsequently bind to HLA molecules on the surface of the malignant B cell. The cells expressing the T-cell epitopes are then targeted by the host immune system for cytolysis by T cells.

Example 15

In Vivo Targeting of B Cell Lymphoma Using the Separately Conjugated T-Cell Epitopes (i.e., "Hairbrush") (e.g., Chronic Lymphocytic Leukaemia)

An agent comprising Rituximab or an anti-CD22 antibody is conjugated with a peptide mixture containing equal parts of five different cytomegalovirus-derived peptides each containing a protease cleavage site specific for either ADAM28 or cathepsin D (i) CKPAKFFRLNLVPMVATV (SEQ ID NO: 58), (ii) CKPAKFFRLRPHERNGFTVL (SEQ ID NO: 59), (iii) CPRSFFRLGKVLEETSVML (SEQ ID NO: 60), (iv) CKPAKFFRLELKRKMIYM (SEQ ID NO: 61) and (v) CPRSFFRLGKQIKVRVDMV (SEQ ID NO: 62). The patient is infused with the agent, which targets all B cells, healthy and malignant. Upon binding malignant cells, the agent comes into contact with proteases whereby cleavage of the protease recognition domain releases the T-cell epitopes (i) NLVPMVATV (SEQ ID NO: 1), (ii) RPHERNGFTVL (SEQ ID NO: 2), (iii) VLEETSVML (SEQ ID NO: 5), (iv) ELKRKMIYM (SEQ ID NO: 23) and (v) QIKVRVDMV (SEQ ID NO: 38), which subsequently bind to HLA molecules on the surface of the malignant B cell. The malignant B cells expressing the T-cell epitopes on their HLA molecules at the cell surface are targeted by the host immune system for cytolysis by T cells.

Example 16

In Vivo Targeting of B-Cell Lymphoma Using a TPEC Comprising Polytope (e.g., Chronic Lymphocytic Leukaemia)

An agent comprising Rituximab or an anti-CD22 antibody is conjugated with a peptide containing four different cytomegalovirus-derived epitopes (i) CGSKPAKFFRLYSEHPTFTSQYGSPRSFFRLGKTPRVTGGGAMGSKPAKFFRLQIKVRVDMVGSPRSFFRLGKELRRKMMYM (SEQ ID NO: 63). Each of the four epitopes is separated from the next one by a protease cleavage site specific for either ADAM28 or cathepsin D in a potential conformation, but not limited to the conformation, Targeting agent-$C_i$-$E_1$-$C_{ii}$-$E_2$-$C_i$-$E_3$-$C_{ii}$-$E_4$ where C is protease cleavage and E is epitope. The patient is infused with the agent, which targets all B cells, healthy and malignant. Upon binding malignant cells, the agent comes into contact with proteases whereby cleavage of the protease recognition domain releases the T-cell epitopes (i) YSEHPTFTSQY (SEQ ID NO: 55), (ii) TPRVTGGGAM (SEQ ID NO: 49), (iii) QIKVRVDMV (SEQ ID NO: 38), and (iv) ELRRKMMYM (SEQ ID NO: 24), which subsequently bind to HLA molecules on the surface of the malignant B cell. The cells expressing the T-cell epitopes are then targeted by the host immune system for cytolysis by T cells.

Example 17

Embodiments Described Herein

Various embodiments are described in the following non-limiting items.

Item 1. A composition for retargeting an immune response to unwanted cells comprising a TPEC wherein:
  a. T is a targeting moiety that is capable of targeting unwanted cells;
  b. L is at least one linker capable of linkage to T, where L may be a peptide bond, at least one peptide, or a chemical linker;
  c. C is at least one cleavage site
    i. cleaved by an enzyme expressed by the unwanted cells;
    ii. cleaved through a pH-sensitive cleavage reaction inside the unwanted cell;
    iii. cleaved by a complement-dependent cleavage reaction; or
    iv. cleaved by a protease that is colocalized to the unwanted cell by a targeting moiety that is the same or different from the targeting moiety in the TPEC; and
  d. E is at least one T-cell epitope,
wherein the L, C, and E moieties are arranged in at least one of the following patterns:
  i. a plurality of L-C-E, each attached separately to T,
  ii. at least one of L-(C-E)n, n is an integer of at least 2 (optionally from about 2 to 50) and with each C-E attached to the L in parallel, and/or
  iii. at least one of L-(C-E)n, n is an integer of at least 2 (optionally from about 2 to 50) and with each C-E attached to the L in series.

Item 2. A composition for retargeting an immune response to unwanted cells comprising a TPEC comprising the formula T-(L-C-E)$_n$ or T-(L-$C_i$-$E_j$)$_n$, wherein:
  a. T is a targeting moiety that is capable of targeting unwanted cells;
  b. L is a linker capable of chemical linkage to T;
  c. C is a cleavage site
    i. cleaved by an enzyme expressed by the unwanted cells;
    ii. cleaved through a pH-sensitive cleavage reaction inside the unwanted cell;
    iii. cleaved by a complement-dependent cleavage reaction; or
    iv. cleaved by a protease that is colocalized to the unwanted cell by a targeting moiety that is the same or different from the targeting moiety in the TPEC; and
  d. E is a T-cell epitope
wherein n is an integer of at least 2 (optionally from about 2 to 50), i is an integer of at least 1 (optionally from about 1 to 50), and j is an integer of at least 2 (optionally from about 1 to 50).

Item 3. A composition for retargeting an immune response to unwanted cells comprising a TPEC comprising the formula T-L-($C_i$-$E_j$)$_n$, wherein:
  a. T is a targeting moiety that is capable of targeting unwanted cells;
  b. L is an optional linker capable of chemical or peptide linkage to T;
  c. C is a cleavage site
    i. cleaved by an enzyme expressed by the unwanted cells;
    ii. cleaved through a pH-sensitive cleavage reaction inside the unwanted cell;
    iii. cleaved by a complement-dependent cleavage reaction; or
    iv. cleaved by a protease that is colocalized to the unwanted cell by a targeting moiety that is the same or different from the targeting moiety in the TPEC; and
  d. E is a T-cell epitope;
wherein n is an integer of at least 2 (optionally from about 2 to 50), i is an integer of at least 1 (optionally from about 1 to 50), and j is an integer of at least 1 (optionally from about 1 to 50).

Item 4. A composition for retargeting an immune response to unwanted cells comprising a TPEC having:
  a. a targeting moiety that is capable of targeting unwanted cells;

b. a plurality of more than 10 T-cell epitopes conjugated to the targeting moiety with at least one cleavage site, wherein the cleavage site is
  i. cleaved by an enzyme expressed by the unwanted cells;
  ii. cleaved through a pH-sensitive cleavage reaction inside the unwanted cell;
  iii. cleaved by a complement-dependent cleavage reaction; or
  iv. cleaved by a protease that is colocalized to the unwanted cell by a targeting moiety that is the same or different from the targeting moiety in the TPEC.

Item 5. The composition of any one of items 1, 2, or 4, wherein the plurality of T-cell epitopes are individually conjugated to the targeting moiety, each T-cell epitope by a cleavage site.

Item 6. The composition of any one of items 1, 3, or 4, wherein the plurality of T-cell epitopes are conjugated as at least one bundle to the targeting moiety by one cleavage site.

Item 7. The composition of item 6, wherein the T-cell epitopes within a bundle have cleavage sites between them.

Item 8. The composition of any one of items 1, 3-4, 6-7, wherein at least two groups of a plurality of T-cell epitopes are conjugated to the targeting moiety, each group by one cleavage site.

Item 9. The composition of any one of items 1-8, wherein the plurality of T-cell epitopes are not all identical.

Item 10. The composition of any one of items 1-8, wherein the plurality of T-cell epitopes are the same.

Item 11. The composition of any one of items 1-8, wherein some the T-cell epitopes are the same and further wherein some are different.

Item 12. The composition of any one of items 1-11, wherein the agent has a plurality of cleavage sites that are the same.

Item 13. The composition of any one of items 1-11, wherein the agent has a plurality of cleavage sites that are not all identical.

Item 14. The composition of any one of items 1, 3-4, and 6-13, wherein the at least one cleavage site and the plurality of T-cell epitopes are conjugated to the targeting agent using at least one peptide bond.

Item 15. The composition of any one of items 1-13, wherein the at least one cleavage site and the plurality of T-cell epitopes are conjugated to the targeting agent through at least one bond other than a peptide bond.

Item 16. The composition of item 15, wherein the at least one cleavage site and the plurality of T-cell epitopes are conjugated to the targeting agent through a Sulfo-SMCC, SMCC, or maleimide linkage.

Item 17. The composition of any one of items 1-16 wherein at least one T-cell epitope is an MHC Class I restricted peptide.

Item 18. The composition of any one of items 1-17, wherein at least one T-cell epitope is an MHC Class II restricted peptide.

Item 19. The composition of any one of items 1-18, wherein the plurality of T-cell epitopes are from about 7 to about 14 amino acids in length.

Item 20. The composition of any one of items 1-19, wherein the plurality of T cell epitopes are about 8 to 13, about 9 to 12, about 9, or about 10 amino acids in length.

Item 21. The composition of any one of items 1-20, wherein the agent comprises about or at least about 2, 3, 4, 5, 6, 7, 8, 9, 10, 20, 30, 40, 50, 60, 70, 80, 90, or 100 T cell epitopes, optionally from 2 to 100 T cell epitopes.

Item 22. The composition of any one of items 1-21, wherein the T-cell epitopes are chosen from CMV, influenza, EBV, hepatitis, chicken pox, mumps, measles, diphtheria, Haemophilus influenzae, rubella, pertussis, polio, pneumococcus, rotavirus, tetanus, vaccinia, and yellow fever T-cell epitopes.

Item 23. The composition of any one of items 1-22, wherein the composition comprises T-cell epitopes from at least two different infectious agents.

Item 24. The composition of any one of items 1-23, wherein the TPEC comprises at least one CMV T-cell epitope.

Item 25. The composition of any one of items 1-9 and 11-24, wherein using a plurality of different T-cell epitopes allows the agent to stimulate a T-cell response in at least about 10%, 20%, 30%, 40%, 50%, 60%, 70%, 80%, or 90% of the human population.

Item 26. The composition of any one of items 1-25, wherein the T-cell epitopes are chosen from HLA-A, HLA-B, HLA-C, HLA-E, HLA-F, HLA-G, CD1d, and MR1.

Item 27. The composition of any one of items 1-26, wherein the T-cell epitopes are chosen from HLA-A*01, HLA-A*02, HLA-A*03, HLA-A*11, HLA-B*44, HLA-B*07, HLA-B*08, HLA-B*15, HLA-B*35, HLA-B*40, HLA-C*07, HLA-C*03, HLA-C*05, HLA-C*04, HLA-C*06, and HLA-E*0101 restricted antigens.

Item 28. The composition of any one of items 1-9 and 11-27, wherein the composition comprises at least the following T-cell epitopes: HLA-A*02, HLA-A*01, and HLA-A*03.

Item 29. The composition of any one of items 1-28, wherein having multiple copies of the same T-cell epitope increases an immune response against the unwanted cell when the agent is administered to a subject.

Item 30. The composition of any one of items 1-29, wherein the T-cell epitopes comprise at least one of SEQ ID NOS: 1-2, 5-7, 15-57.

Item 31. The composition of any one of items 1-30, wherein the targeting moiety targets the unwanted cells by specifically binding to the unwanted cells.

Item 32. The composition of any one of items 1-32, wherein the targeting moiety specifically binds the unwanted cells even while the plurality of T-cell epitopes are conjugated to the targeting moiety.

Item 33. The composition of any one of items 1-32, wherein the targeting moiety is an antibody or functional part thereof.

Item 34. The composition of any one of items 1-33, wherein the T-cell epitopes are flanked on one or both ends by at least one human protein domain.

Item 35. The composition of items 34, wherein at least one human protein domain is a beta barrel or a coiled coil.

Item 36. The composition of any one of items 34-35, wherein the human protein domain is a CL, CH2, and/or CH3 domain.

Item 37. The composition of any one of items 34-35, wherein the human protein domain is a FN3 domain, beta-sandwich, Lipocalin, EETI-II/AGRP, Kunitz domain (BPTI), Thioredoxin, Protein A, Ankyrin, gamma-B-crystallin/ubiquitin, CTLD3/Tetranexin LDLR-A, human serum albumin, immunoglobulin CH2 domain, or camelid VHH domain.

Item 38. The composition of any one of item 34-35 or 37, wherein the human protein domain is not a human immunoglobulin protein domain.

Item 39. The composition of any one of items 34-38, wherein the human protein domain displays the T-cell epitopes on its three-dimensional surface.

Item 40. The composition of any one of items 1-39, wherein the cleavage site is capable of being cleaved outside the unwanted cells.

Item 41. The composition of any one of items 1-40, wherein the enzyme expressed by the unwanted cells is a protease.

Item 42. The composition of any one of items 1-41, wherein the unwanted cells are cancer cells.

Item 43. A composition comprising a plurality of different TPECs of any one of items 1-42, wherein each targeting agent is conjugated to a plurality of identical T-cell epitopes.

Item 44. A composition comprising a plurality of compositions of any one of items 1-42, wherein at least some of the targeting agents in the composition are conjugated to a plurality of T-cell epitopes that are not identical.

Item 45. A composition comprising a plurality of compositions of item 44, wherein at least some of the compositions are not identical.

Item 46. A composition comprising a plurality of compositions of any one of items 43-45, wherein the composition comprises at least about 3, 4, 5, 6, 7, 8, 9, 10, 15, 20, 25, or more different TPECs.

Item 47. A pharmaceutical composition comprising a composition of any one of items 1-46 and a pharmaceutically acceptable carrier.

Item 48. A method of treating a disease in a patient characterized by the presence of unwanted cells comprising administering a composition of any one of items 1-47 to the patient.

Item 49. A method of retargeting an immune response of a patient to unwanted cells comprising administering a composition of any one of items 1-47 to the patient.

Item 50. The method of any of items 48-49, wherein the patient does not develop an immune response against the composition sufficient to inactivate the composition.

Item 51. The method of any one of items 48-50, wherein the patient receives multiple doses of the composition over at least 30, 45, 60, 75, 90, 120, 150, or more days or on an ongoing basis.

Item 52. The method of any one of items 48-50, wherein the patient receives multiple doses of the composition over at least 1, 2, 3, 4, 5, 6, 7, 8, 9, 10, 11, or 12 months or on an ongoing basis.

Item 53. The method of any one of items 48-52, wherein the composition can be administered to a patient in relapse who received the composition for an earlier round of therapy.

Item 54. The method of any one of items 48-53, wherein the patient has cancer.

EQUIVALENTS

The foregoing written specification is considered to be sufficient to enable one skilled in the art to practice the embodiments. The foregoing description and Examples detail certain embodiments and describes the best mode contemplated by the inventors. It will be appreciated, however, that no matter how detailed the foregoing may appear in text, the embodiment may be practiced in many ways and should be construed in accordance with the appended claims and any equivalents thereof.

As used herein, the term about refers to a numeric value, including, for example, whole numbers, fractions, and percentages, whether or not explicitly indicated. The term about generally refers to a range of numerical values (e.g., +/−5-10% of the recited range) that one of ordinary skill in the art would consider equivalent to the recited value (e.g., having the same function or result). When terms such as at least and about precede a list of numerical values or ranges, the terms modify all of the values or ranges provided in the list. In some instances, the term about may include numerical values that are rounded to the nearest significant figure.

What is claimed is:

1. A composition for retargeting a virus-specific existing T-cell immune response to cancer cells comprising a targeting moiety peptide epitope complex (TPEC) wherein:
   a. T is a targeting moiety that is an antibody or antigen-binding fragment thereof capable of targeting cancer cells;
   b. L is at least one linker capable of linkage to T where L is a peptide bond or at least one peptide;
   c. C is at least one cleavage site cleaved by an enzyme outside of the cancer cell and expressed by the cancer cell or cleaved by a protease that is outside of the cancer cell and colocalized to the cancer cell by a targeting moiety that is the same or different from the targeting moiety in the TPEC; and
   d. E is at least one viral T-cell epitope that elicits an existing immune response in a human subject and binds to a HLA molecule on the surface of the cancer cells of the human subject and has a HLA matched to the subject, wherein the L, C, and E moieties are arranged in a pattern of at least one of L-(C-E)n, wherein n is an integer of at least 2 and with each C-E attached to the L in series.

2. The composition of claim 1, wherein the composition comprises a plurality of more than 10 T-cell epitopes conjugated to the targeting moiety with at least one cleavage site.

3. The composition of claims 1, wherein the plurality of T-cell epitopes are not all identical.

4. The composition of claim 1, wherein at least one T-cell epitope is an MHC Class I restricted peptide.

5. The composition of claim 1, wherein at least one T-cell epitope is an MHC Class II restricted peptide.

6. The composition of claim 1, wherein the plurality of T-cell epitopes are from about 7 to about 14 amino acids in length.

7. The composition of claim 1, wherein the composition comprises at least about 2, 3, 4, 5, 6, 7, 8, 9, or 10 T cell epitopes.

8. The composition of claim 1, wherein the T-cell epitopes are chosen from CMV, influenza, EBV, hepatitis, chicken pox, mumps, measles, rubella, polio, rotavirus, vaccinia, and yellow fever T-cell epitopes.

9. The composition of claim 1, wherein the composition comprises T-cell epitopes from at least two different viruses.

10. The composition of claim 1, wherein the T-cell epitopes are chosen from HLA-A, HLA-B, HLA-C, HLA-E, HLA-F, HLA-G, CD1d, and MR1.

11. The composition of claim 1, wherein the T-cell epitopes are chosen from HLA-A*01, HLA-A*02, HLA-A*03, HLA-A*11, HLA-B*44, HLA-B*07, HLA-B*08, HLA-B*15, HLA-B*35, HLA-B*40, HLA-C*07, HLA-C*03, HLA-C*05, HLA-C*04, HLA-C*06, and HLA-E*0101 restricted antigens.

12. The composition of claim 1, wherein the composition comprises at least the following T-cell epitopes: HLA-A*02, HLA-A*01, and HLA-A*03.

13. The composition of claim 1, wherein the T-cell epitopes comprise at least one of SEQ ID NOS: 1-2, 5-7, 15-57.

14. The composition of claim 1, wherein the T-cell epitopes are flanked on one or both ends by at least one human protein domain.

15. The composition of claim 1, wherein the enzyme expressed by the cancer cells is a protease.

16. The composition of claim 1, wherein the antibody or antigen-binding fragment thereof is an anti-CEA or anti-CEACAM antibody or antigen-binding fragment thereof.

* * * * *

SEQUENCE LISTING

```
<160> NUMBER OF SEQ ID NOS: 188

<210> SEQ ID NO 1
<211> LENGTH: 9
<212> TYPE: PRT
<213> ORGANISM: Human cytomegalovirus

<400> SEQUENCE: 1

Asn Leu Val Pro Met Val Ala Thr Val
1               5

<210> SEQ ID NO 2
<211> LENGTH: 11
<212> TYPE: PRT
<213> ORGANISM: Human cytomegalovirus

<400> SEQUENCE: 2

Arg Pro His Glu Arg Asn Gly Phe Thr Val Leu
1               5                   10

<210> SEQ ID NO 3
<211> LENGTH: 16
<212> TYPE: PRT
<213> ORGANISM: Artificial Sequence
<220> FEATURE:
<223> OTHER INFORMATION: CMV TCE and cleavage site from capthepsin B
<220> FEATURE:
<221> NAME/KEY: MISC_FEATURE
<222> LOCATION: (13)..(14)
<223> OTHER INFORMATION: Cleavage site
<220> FEATURE:
<221> NAME/KEY: MISC_FEATURE
```

```
<222> LOCATION: (14)..(14)
<223> OTHER INFORMATION: X = citrulline

<400> SEQUENCE: 3

Asn Leu Val Pro Met Val Ala Thr Val Ala Ser Gly Val Xaa Gly Cys
1               5                   10                  15

<210> SEQ ID NO 4
<211> LENGTH: 18
<212> TYPE: PRT
<213> ORGANISM: Artificial Sequence
<220> FEATURE:
<223> OTHER INFORMATION: CMV TCE and cleavage site from capthepsin B
<220> FEATURE:
<221> NAME/KEY: MISC_FEATURE
<222> LOCATION: (12)..(18)
<223> OTHER INFORMATION: Cleavage site

<400> SEQUENCE: 4

Arg Pro His Glu Arg Asn Gly Phe Thr Val Leu Ala Ser Gly Phe Lys
1               5                   10                  15

Gly Cys

<210> SEQ ID NO 5
<211> LENGTH: 9
<212> TYPE: PRT
<213> ORGANISM: Human cytomegalovirus

<400> SEQUENCE: 5

Val Leu Glu Glu Thr Ser Val Met Leu
1               5

<210> SEQ ID NO 6
<211> LENGTH: 9
<212> TYPE: PRT
<213> ORGANISM: Artificial Sequence
<220> FEATURE:
<223> OTHER INFORMATION: CMV TCE, (IE1, 309-317, HLA-C7),
      (Peptidomimetic of SEQ ID NO: 17)
<220> FEATURE:
<221> NAME/KEY: MISC_FEATURE
<222> LOCATION: (1)..(9)
<223> OTHER INFORMATION: X = alpha-aminobutyric acid

<400> SEQUENCE: 6

Xaa Arg Val Leu Xaa Xaa Tyr Val Leu
1               5

<210> SEQ ID NO 7
<211> LENGTH: 9
<212> TYPE: PRT
<213> ORGANISM: Human cytomegalovirus

<400> SEQUENCE: 7

Tyr Ile Leu Glu Glu Thr Ser Val Met
1               5

<210> SEQ ID NO 8
<211> LENGTH: 16
<212> TYPE: PRT
<213> ORGANISM: Artificial Sequence
<220> FEATURE:
<223> OTHER INFORMATION: CMV TCE and cleavage site from capthepsin B
<220> FEATURE:
<221> NAME/KEY: MISC_FEATURE
<222> LOCATION: (10)..(16)
<223> OTHER INFORMATION: Cleavage site
```

```
<400> SEQUENCE: 8

Val Leu Glu Glu Thr Ser Val Met Leu Ala Ser Gly Phe Lys Gly Cys
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: CMV TCE and cleavage site from capthepsin B
<220> FEATURE:
<221> NAME/KEY: MISC_FEATURE
<222> LOCATION: (1)..(16)
<223> OTHER INFORMATION: X = alpha-aminobutyric acid
<220> FEATURE:
<221> NAME/KEY: MISC_FEATURE
<222> LOCATION: (10)..(16)
<223> OTHER INFORMATION: Cleavage site

<400> SEQUENCE: 9

Xaa Arg Val Leu Xaa Xaa Tyr Val Leu Ala Ser Gly Phe Lys Gly Cys
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: CMV TCE and cleavage site from capthepsin B
<220> FEATURE:
<221> NAME/KEY: MISC_FEATURE
<222> LOCATION: (10)..(16)
<223> OTHER INFORMATION: Cleavage site

<400> SEQUENCE: 10

Tyr Ile Leu Glu Glu Thr Ser Val Met Ala Ser Gly Phe Lys Gly Cys
1               5                   10                  15

<210> SEQ ID NO 11
<211> LENGTH: 25
<212> TYPE: PRT
<213> ORGANISM: Artificial Sequence
<220> FEATURE:
<223> OTHER INFORMATION: Polytope containing two different CMV-derived
      epitopes separated by cathepsin B cleavage site
<220> FEATURE:
<221> NAME/KEY: MISC_FEATURE
<222> LOCATION: (1)..(4)
<223> OTHER INFORMATION: Cleavage site
<220> FEATURE:
<221> NAME/KEY: MISC_FEATURE
<222> LOCATION: (15)..(16)
<223> OTHER INFORMATION: Cleavage site

<400> SEQUENCE: 11

Cys Gly Val Ala Asn Leu Val Pro Met Val Ala Thr Val Ala Val Ala
1               5                   10                  15

Val Leu Glu Glu Thr Ser Val Met Leu
            20                  25

<210> SEQ ID NO 12
<211> LENGTH: 25
<212> TYPE: PRT
<213> ORGANISM: Artificial Sequence
<220> FEATURE:
<223> OTHER INFORMATION: Polytope containing two different CMV-derived
      epitopes separated by cathepsin B cleavage site
<220> FEATURE:
<221> NAME/KEY: MISC_FEATURE
<222> LOCATION: (1)..(3)
```

```
<223> OTHER INFORMATION: Cleavage site
<220> FEATURE:
<221> NAME/KEY: MISC_FEATURE
<222> LOCATION: (15)..(16)
<223> OTHER INFORMATION: Cleavage site

<400> SEQUENCE: 12

Cys Val Ala Arg Pro His Glu Arg Asn Gly Phe Thr Val Leu Val Ala
1               5                   10                  15

Asn Leu Val Pro Met Val Ala Thr Val
            20                  25

<210> SEQ ID NO 13
<211> LENGTH: 25
<212> TYPE: PRT
<213> ORGANISM: Artificial Sequence
<220> FEATURE:
<223> OTHER INFORMATION: Polytope containing two different CMV-derived
      epitopes separated by cathepsin B cleavage site
<220> FEATURE:
<221> NAME/KEY: MISC_FEATURE
<222> LOCATION: (1)..(4)
<223> OTHER INFORMATION: Cleavage site
<220> FEATURE:
<221> NAME/KEY: MISC_FEATURE
<222> LOCATION: (14)..(14)
<223> OTHER INFORMATION: Cleavage site

<400> SEQUENCE: 13

Cys Gly Val Ala Asn Leu Val Pro Met Val Ala Thr Val Ala Arg Pro
1               5                   10                  15

His Glu Arg Asn Gly Phe Thr Val Leu
            20                  25

<210> SEQ ID NO 14
<211> LENGTH: 55
<212> TYPE: PRT
<213> ORGANISM: Artificial Sequence
<220> FEATURE:
<223> OTHER INFORMATION: Polytope containing five different CMV-derived
      epitopes separated by cathepsin B cleavage sites
<220> FEATURE:
<221> NAME/KEY: MISC_FEATURE
<222> LOCATION: (2)..(5)
<223> OTHER INFORMATION: Cleavage site
<220> FEATURE:
<221> NAME/KEY: MISC_FEATURE
<222> LOCATION: (15)..(18)
<223> OTHER INFORMATION: Cleavage site
<220> FEATURE:
<221> NAME/KEY: MISC_FEATURE
<222> LOCATION: (30)..(33)
<223> OTHER INFORMATION: Cleavage site
<220> FEATURE:
<221> NAME/KEY: MISC_FEATURE
<222> LOCATION: (43)..(46)
<223> OTHER INFORMATION: Cleavage site

<400> SEQUENCE: 14

Cys Gly Ser Phe Arg Val Thr Glu His Asp Thr Leu Leu Tyr Gly Ser
1               5                   10                  15

Phe Arg Arg Pro His Glu Arg Asn Gly Phe Thr Val Leu Gly Ser Phe
            20                  25                  30

Arg Glu Leu Lys Arg Lys Met Ile Tyr Met Gly Ser Phe Arg Asn Leu
        35                  40                  45

Val Pro Met Val Ala Thr Val
        50                  55
```

```
<210> SEQ ID NO 15
<211> LENGTH: 10
<212> TYPE: PRT
<213> ORGANISM: Human cytomegalovirus

<400> SEQUENCE: 15

Ala Thr Thr Phe Leu Gln Thr Met Leu Arg
1               5                   10

<210> SEQ ID NO 16
<211> LENGTH: 12
<212> TYPE: PRT
<213> ORGANISM: Human cytomegalovirus

<400> SEQUENCE: 16

Cys Pro Ser Gln Glu Pro Met Ser Ile Tyr Val Tyr
1               5                   10

<210> SEQ ID NO 17
<211> LENGTH: 9
<212> TYPE: PRT
<213> ORGANISM: Human cytomegalovirus

<400> SEQUENCE: 17

Cys Arg Val Leu Cys Cys Tyr Val Leu
1               5

<210> SEQ ID NO 18
<211> LENGTH: 9
<212> TYPE: PRT
<213> ORGANISM: Human cytomegalovirus

<400> SEQUENCE: 18

Cys Val Glu Thr Met Cys Asn Glu Tyr
1               5

<210> SEQ ID NO 19
<211> LENGTH: 9
<212> TYPE: PRT
<213> ORGANISM: Human cytomegalovirus

<400> SEQUENCE: 19

Asp Glu Leu Arg Arg Lys Met Met Tyr
1               5

<210> SEQ ID NO 20
<211> LENGTH: 10
<212> TYPE: PRT
<213> ORGANISM: Human cytomegalovirus

<400> SEQUENCE: 20

Asp Thr Pro Val Leu Pro His Glu Thr Arg
1               5                   10

<210> SEQ ID NO 21
<211> LENGTH: 9
<212> TYPE: PRT
<213> ORGANISM: Human cytomegalovirus

<400> SEQUENCE: 21

Glu Glu Ala Ile Val Ala Tyr Thr Leu
1               5

<210> SEQ ID NO 22
<211> LENGTH: 9
```

```
<212> TYPE: PRT
<213> ORGANISM: Human cytomegalovirus

<400> SEQUENCE: 22

Glu Phe Phe Asp Ala Asn Asp Ile Tyr
1               5

<210> SEQ ID NO 23
<211> LENGTH: 9
<212> TYPE: PRT
<213> ORGANISM: Human cytomegalovirus

<400> SEQUENCE: 23

Glu Leu Lys Arg Lys Met Ile Tyr Met
1               5

<210> SEQ ID NO 24
<211> LENGTH: 9
<212> TYPE: PRT
<213> ORGANISM: Human cytomegalovirus

<400> SEQUENCE: 24

Glu Leu Arg Arg Lys Met Met Tyr Met
1               5

<210> SEQ ID NO 25
<211> LENGTH: 9
<212> TYPE: PRT
<213> ORGANISM: Human cytomegalovirus

<400> SEQUENCE: 25

Glu Val Ile Ser Val Met Lys Arg Arg
1               5

<210> SEQ ID NO 26
<211> LENGTH: 9
<212> TYPE: PRT
<213> ORGANISM: Human cytomegalovirus

<400> SEQUENCE: 26

Phe Glu Gln Pro Thr Glu Thr Pro Pro
1               5

<210> SEQ ID NO 27
<211> LENGTH: 11
<212> TYPE: PRT
<213> ORGANISM: Human cytomegalovirus

<400> SEQUENCE: 27

Phe Pro Lys Thr Thr Asn Gly Cys Ser Gln Ala
1               5                   10

<210> SEQ ID NO 28
<211> LENGTH: 8
<212> TYPE: PRT
<213> ORGANISM: Human cytomegalovirus

<400> SEQUENCE: 28

Phe Pro Thr Lys Asp Val Ala Leu
1               5

<210> SEQ ID NO 29
<211> LENGTH: 11
<212> TYPE: PRT
<213> ORGANISM: Human cytomegalovirus
```

<400> SEQUENCE: 29

Phe Thr Ser Gln Tyr Arg Ile Gln Gly Lys Leu
1               5                   10

<210> SEQ ID NO 30
<211> LENGTH: 11
<212> TYPE: PRT
<213> ORGANISM: Human cytomegalovirus

<400> SEQUENCE: 30

Phe Val Phe Pro Thr Lys Asp Val Ala Leu Arg
1               5                   10

<210> SEQ ID NO 31
<211> LENGTH: 10
<212> TYPE: PRT
<213> ORGANISM: Human cytomegalovirus

<400> SEQUENCE: 31

Ile Ile Tyr Thr Arg Asn His Glu Val Lys
1               5                   10

<210> SEQ ID NO 32
<211> LENGTH: 9
<212> TYPE: PRT
<213> ORGANISM: Human cytomegalovirus

<400> SEQUENCE: 32

Ile Pro Ser Ile Asn Val His His Tyr
1               5

<210> SEQ ID NO 33
<211> LENGTH: 9
<212> TYPE: PRT
<213> ORGANISM: Human cytomegalovirus

<400> SEQUENCE: 33

Lys Ala Arg Asp His Leu Ala Val Leu
1               5

<210> SEQ ID NO 34
<211> LENGTH: 9
<212> TYPE: PRT
<213> ORGANISM: Human cytomegalovirus

<400> SEQUENCE: 34

Lys Glu Val Asn Ser Gln Leu Ser Leu
1               5

<210> SEQ ID NO 35
<211> LENGTH: 9
<212> TYPE: PRT
<213> ORGANISM: Human cytomegalovirus

<400> SEQUENCE: 35

Lys Arg Lys Met Ile Tyr Met Cys Tyr
1               5

<210> SEQ ID NO 36
<211> LENGTH: 9
<212> TYPE: PRT
<213> ORGANISM: Human cytomegalovirus

<400> SEQUENCE: 36

Met Leu Asn Ile Pro Ser Ile Asn Val
1               5

<210> SEQ ID NO 37
<211> LENGTH: 9
<212> TYPE: PRT
<213> ORGANISM: Human cytomegalovirus

<400> SEQUENCE: 37

Asn Val Arg Arg Ser Trp Glu Glu Leu
1               5

<210> SEQ ID NO 38
<211> LENGTH: 9
<212> TYPE: PRT
<213> ORGANISM: Human cytomegalovirus

<400> SEQUENCE: 38

Gln Ile Lys Val Arg Val Asp Met Val
1               5

<210> SEQ ID NO 39
<211> LENGTH: 10
<212> TYPE: PRT
<213> ORGANISM: Human cytomegalovirus

<400> SEQUENCE: 39

Gln Pro Ser Leu Ile Leu Val Ser Gln Tyr
1               5                   10

<210> SEQ ID NO 40
<211> LENGTH: 11
<212> TYPE: PRT
<213> ORGANISM: Human cytomegalovirus

<400> SEQUENCE: 40

Gln Thr Val Thr Ser Thr Pro Val Gln Gly Arg
1               5                   10

<210> SEQ ID NO 41
<211> LENGTH: 9
<212> TYPE: PRT
<213> ORGANISM: Human cytomegalovirus

<400> SEQUENCE: 41

Gln Tyr Asp Val Pro Ala Ala Leu Phe
1               5

<210> SEQ ID NO 42
<211> LENGTH: 10
<212> TYPE: PRT
<213> ORGANISM: Human cytomegalovirus

<400> SEQUENCE: 42

Gln Tyr Val Lys Val Tyr Leu Glu Ser Phe
1               5                   10

<210> SEQ ID NO 43
<211> LENGTH: 9
<212> TYPE: PRT
<213> ORGANISM: Human cytomegalovirus

<400> SEQUENCE: 43

Arg Gly Asp Pro Phe Asp Lys Asn Tyr

```
<210> SEQ ID NO 44
<211> LENGTH: 9
<212> TYPE: PRT
<213> ORGANISM: Human cytomegalovirus

<400> SEQUENCE: 44

Arg Ile Phe Ala Glu Leu Glu Gly Val
1               5

<210> SEQ ID NO 45
<211> LENGTH: 9
<212> TYPE: PRT
<213> ORGANISM: Human cytomegalovirus

<400> SEQUENCE: 45

Arg Ile Trp Cys Leu Val Val Cys Val
1               5

<210> SEQ ID NO 46
<211> LENGTH: 9
<212> TYPE: PRT
<213> ORGANISM: Human cytomegalovirus

<400> SEQUENCE: 46

Arg Arg Ile Glu Glu Ile Cys Met Lys
1               5

<210> SEQ ID NO 47
<211> LENGTH: 9
<212> TYPE: PRT
<213> ORGANISM: Human cytomegalovirus

<400> SEQUENCE: 47

Arg Arg Lys Met Met Tyr Met Cys Tyr
1               5

<210> SEQ ID NO 48
<211> LENGTH: 10
<212> TYPE: PRT
<213> ORGANISM: Human cytomegalovirus

<400> SEQUENCE: 48

Ser Glu His Pro Thr Phe Thr Ser Gln Tyr
1               5                   10

<210> SEQ ID NO 49
<211> LENGTH: 10
<212> TYPE: PRT
<213> ORGANISM: Human cytomegalovirus

<400> SEQUENCE: 49

Thr Pro Arg Val Thr Gly Gly Gly Ala Met
1               5                   10

<210> SEQ ID NO 50
<211> LENGTH: 11
<212> TYPE: PRT
<213> ORGANISM: Human cytomegalovirus

<400> SEQUENCE: 50

Thr Thr Val Tyr Pro Pro Ser Ser Thr Ala Lys
1               5                   10
```

```
<210> SEQ ID NO 51
<211> LENGTH: 9
<212> TYPE: PRT
<213> ORGANISM: Human cytomegalovirus

<400> SEQUENCE: 51

Thr Val Arg Ser His Cys Val Ser Lys
1               5

<210> SEQ ID NO 52
<211> LENGTH: 9
<212> TYPE: PRT
<213> ORGANISM: Human cytomegalovirus

<400> SEQUENCE: 52

Val Leu Ala Glu Leu Val Lys Gln Ile
1               5

<210> SEQ ID NO 53
<211> LENGTH: 9
<212> TYPE: PRT
<213> ORGANISM: Human cytomegalovirus

<400> SEQUENCE: 53

Val Thr Glu His Asp Thr Leu Leu Tyr
1               5

<210> SEQ ID NO 54
<211> LENGTH: 9
<212> TYPE: PRT
<213> ORGANISM: Human cytomegalovirus

<400> SEQUENCE: 54

Val Tyr Ala Leu Pro Leu Lys Met Leu
1               5

<210> SEQ ID NO 55
<211> LENGTH: 11
<212> TYPE: PRT
<213> ORGANISM: Human cytomegalovirus

<400> SEQUENCE: 55

Tyr Ser Glu His Pro Thr Phe Thr Ser Gln Tyr
1               5                   10

<210> SEQ ID NO 56
<211> LENGTH: 10
<212> TYPE: PRT
<213> ORGANISM: Human cytomegalovirus

<400> SEQUENCE: 56

Tyr Thr Pro Asp Ser Thr Pro Cys His Arg
1               5                   10

<210> SEQ ID NO 57
<211> LENGTH: 9
<212> TYPE: PRT
<213> ORGANISM: Human cytomegalovirus

<400> SEQUENCE: 57

Tyr Val Leu Glu Glu Thr Ser Val Met
1               5

<210> SEQ ID NO 58
```

```
<211> LENGTH: 18
<212> TYPE: PRT
<213> ORGANISM: Artificial Sequence
<220> FEATURE:
<223> OTHER INFORMATION: CMV TCE and cleavage site from ADAM28
<220> FEATURE:
<221> NAME/KEY: MISC_FEATURE
<222> LOCATION: (2)..(9)
<223> OTHER INFORMATION: Cleavage site

<400> SEQUENCE: 58

Cys Lys Pro Ala Lys Phe Phe Arg Leu Asn Leu Val Pro Met Val Ala
1               5                   10                  15

Thr Val

<210> SEQ ID NO 59
<211> LENGTH: 20
<212> TYPE: PRT
<213> ORGANISM: Artificial Sequence
<220> FEATURE:
<223> OTHER INFORMATION: CMV TCE and cleavage site from ADAM28
<220> FEATURE:
<221> NAME/KEY: MISC_FEATURE
<222> LOCATION: (2)..(9)
<223> OTHER INFORMATION: Cleavage site

<400> SEQUENCE: 59

Cys Lys Pro Ala Lys Phe Phe Arg Leu Arg Pro His Glu Arg Asn Gly
1               5                   10                  15

Phe Thr Val Leu
            20

<210> SEQ ID NO 60
<211> LENGTH: 19
<212> TYPE: PRT
<213> ORGANISM: Artificial Sequence
<220> FEATURE:
<223> OTHER INFORMATION: CMV TCE and cleavage site from capthepsin D
<220> FEATURE:
<221> NAME/KEY: MISC_FEATURE
<222> LOCATION: (2)..(10)
<223> OTHER INFORMATION: Cleavage site

<400> SEQUENCE: 60

Cys Pro Arg Ser Phe Phe Arg Leu Gly Lys Val Leu Glu Glu Thr Ser
1               5                   10                  15

Val Met Leu

<210> SEQ ID NO 61
<211> LENGTH: 18
<212> TYPE: PRT
<213> ORGANISM: Artificial Sequence
<220> FEATURE:
<223> OTHER INFORMATION: CMV TCE and cleavage site from ADAM28
<220> FEATURE:
<221> NAME/KEY: MISC_FEATURE
<222> LOCATION: (2)..(9)
<223> OTHER INFORMATION: Cleavage site

<400> SEQUENCE: 61

Cys Lys Pro Ala Lys Phe Phe Arg Leu Glu Leu Lys Arg Lys Met Ile
1               5                   10                  15

Tyr Met

<210> SEQ ID NO 62
<211> LENGTH: 19
<212> TYPE: PRT
```

<213> ORGANISM: Artificial Sequence
<220> FEATURE:
<223> OTHER INFORMATION: CMV TCE and cleavage site from capthepsin D
<220> FEATURE:
<221> NAME/KEY: MISC_FEATURE
<222> LOCATION: (2)..(10)
<223> OTHER INFORMATION: Cleavage site

<400> SEQUENCE: 62

Cys Pro Arg Ser Phe Phe Arg Leu Gly Lys Gln Ile Lys Val Arg Val
1               5                   10                  15

Asp Met Val

<210> SEQ ID NO 63
<211> LENGTH: 82
<212> TYPE: PRT
<213> ORGANISM: Artificial Sequence
<220> FEATURE:
<223> OTHER INFORMATION: Polytope comprising four different
      cytomegalovirus epitopes, each separated by either an ADAM28 or
      cathepsin D cleavage site
<220> FEATURE:
<221> NAME/KEY: MISC_FEATURE
<222> LOCATION: (4)..(11)
<223> OTHER INFORMATION: Cleavage site
<220> FEATURE:
<221> NAME/KEY: MISC_FEATURE
<222> LOCATION: (25)..(33)
<223> OTHER INFORMATION: Cleavage site
<220> FEATURE:
<221> NAME/KEY: MISC_FEATURE
<222> LOCATION: (46)..(53)
<223> OTHER INFORMATION: Cleavage site
<220> FEATURE:
<221> NAME/KEY: MISC_FEATURE
<222> LOCATION: (65)..(73)
<223> OTHER INFORMATION: Cleavage site

<400> SEQUENCE: 63

Cys Gly Ser Lys Pro Ala Lys Phe Phe Arg Leu Tyr Ser Glu His Pro
1               5                   10                  15

Thr Phe Thr Ser Gln Tyr Gly Ser Pro Arg Ser Phe Phe Arg Leu Gly
                20                  25                  30

Lys Thr Pro Arg Val Thr Gly Gly Ala Met Gly Ser Lys Pro Ala
            35                  40                  45

Lys Phe Phe Arg Leu Gln Ile Lys Val Arg Val Asp Met Val Gly Ser
        50                  55                  60

Pro Arg Ser Phe Phe Arg Leu Gly Lys Glu Leu Arg Arg Lys Met Met
65                  70                  75                  80

Tyr Met

<210> SEQ ID NO 64
<211> LENGTH: 9
<212> TYPE: PRT
<213> ORGANISM: Epstein Barr Virus

<400> SEQUENCE: 64

Arg Pro Gln Lys Arg Pro Ser Cys Ile
1               5

<210> SEQ ID NO 65
<211> LENGTH: 9
<212> TYPE: PRT
<213> ORGANISM: Epstein Barr Virus

<400> SEQUENCE: 65

```
His Pro Val Gly Glu Ala Asp Tyr Phe
1               5

<210> SEQ ID NO 66
<211> LENGTH: 11
<212> TYPE: PRT
<213> ORGANISM: Epstein Barr Virus

<400> SEQUENCE: 66

His Pro Val Gly Glu Ala Asp Tyr Phe Glu Tyr
1               5                   10

<210> SEQ ID NO 67
<211> LENGTH: 9
<212> TYPE: PRT
<213> ORGANISM: Epstein Barr Virus

<400> SEQUENCE: 67

Ile Pro Gln Cys Arg Leu Thr Pro Leu
1               5

<210> SEQ ID NO 68
<211> LENGTH: 9
<212> TYPE: PRT
<213> ORGANISM: Epstein Barr Virus

<400> SEQUENCE: 68

Val Leu Lys Asp Ala Ile Lys Asp Leu
1               5

<210> SEQ ID NO 69
<211> LENGTH: 10
<212> TYPE: PRT
<213> ORGANISM: Epstein Barr Virus

<400> SEQUENCE: 69

Tyr His Leu Ile Val Asp Thr Asp Ser Leu
1               5                   10

<210> SEQ ID NO 70
<211> LENGTH: 10
<212> TYPE: PRT
<213> ORGANISM: Epstein Barr Virus

<400> SEQUENCE: 70

Asp Thr Pro Leu Ile Pro Leu Thr Ile Phe
1               5                   10

<210> SEQ ID NO 71
<211> LENGTH: 9
<212> TYPE: PRT
<213> ORGANISM: Epstein Barr Virus

<400> SEQUENCE: 71

Arg Pro Thr Glu Leu Gln Pro Thr Pro
1               5

<210> SEQ ID NO 72
<211> LENGTH: 9
<212> TYPE: PRT
<213> ORGANISM: Epstein Barr Virus

<400> SEQUENCE: 72

Gln Ala Lys Trp Arg Leu Gln Thr Leu
1               5
```

```
<210> SEQ ID NO 73
<211> LENGTH: 9
<212> TYPE: PRT
<213> ORGANISM: Epstein Barr Virus

<400> SEQUENCE: 73

Ala Tyr Ser Ser Trp Met Tyr Ser Tyr
1               5

<210> SEQ ID NO 74
<211> LENGTH: 8
<212> TYPE: PRT
<213> ORGANISM: Epstein Barr Virus

<400> SEQUENCE: 74

Arg Tyr Ser Ile Phe Phe Asp Tyr
1               5

<210> SEQ ID NO 75
<211> LENGTH: 9
<212> TYPE: PRT
<213> ORGANISM: Epstein Barr Virus

<400> SEQUENCE: 75

Phe Leu Arg Gly Arg Ala Tyr Gly Leu
1               5

<210> SEQ ID NO 76
<211> LENGTH: 10
<212> TYPE: PRT
<213> ORGANISM: Epstein Barr Virus

<400> SEQUENCE: 76

Lys Arg Pro Pro Ile Phe Ile Arg Arg Leu
1               5                   10

<210> SEQ ID NO 77
<211> LENGTH: 9
<212> TYPE: PRT
<213> ORGANISM: Epstein Barr Virus

<400> SEQUENCE: 77

Arg Pro Pro Ile Phe Ile Arg Arg Leu
1               5

<210> SEQ ID NO 78
<211> LENGTH: 9
<212> TYPE: PRT
<213> ORGANISM: Epstein Barr Virus

<400> SEQUENCE: 78

Leu Glu Lys Ala Arg Gly Ser Thr Tyr
1               5

<210> SEQ ID NO 79
<211> LENGTH: 9
<212> TYPE: PRT
<213> ORGANISM: Epstein Barr Virus

<400> SEQUENCE: 79

His Leu Ala Ala Gln Gly Met Ala Tyr
1               5
```

```
<210> SEQ ID NO 80
<211> LENGTH: 9
<212> TYPE: PRT
<213> ORGANISM: Epstein Barr Virus

<400> SEQUENCE: 80

Tyr Pro Leu His Glu Gln His Gly Met
1               5

<210> SEQ ID NO 81
<211> LENGTH: 9
<212> TYPE: PRT
<213> ORGANISM: Epstein Barr Virus

<400> SEQUENCE: 81

Val Phe Ser Asp Gly Arg Val Ala Cys
1               5

<210> SEQ ID NO 82
<211> LENGTH: 9
<212> TYPE: PRT
<213> ORGANISM: Epstein Barr Virus

<400> SEQUENCE: 82

Val Pro Ala Pro Ala Gly Pro Ile Val
1               5

<210> SEQ ID NO 83
<211> LENGTH: 9
<212> TYPE: PRT
<213> ORGANISM: Epstein Barr Virus

<400> SEQUENCE: 83

Ser Val Arg Asp Arg Leu Ala Arg Leu
1               5

<210> SEQ ID NO 84
<211> LENGTH: 9
<212> TYPE: PRT
<213> ORGANISM: Epstein Barr Virus

<400> SEQUENCE: 84

Arg Leu Arg Ala Glu Ala Gln Val Lys
1               5

<210> SEQ ID NO 85
<211> LENGTH: 10
<212> TYPE: PRT
<213> ORGANISM: Epstein Barr Virus

<400> SEQUENCE: 85

Val Gln Pro Pro Gln Leu Thr Leu Gln Val
1               5                   10

<210> SEQ ID NO 86
<211> LENGTH: 9
<212> TYPE: PRT
<213> ORGANISM: Epstein Barr Virus

<400> SEQUENCE: 86

His Arg Cys Gln Ala Ile Arg Lys Lys
1               5

<210> SEQ ID NO 87
<211> LENGTH: 9
```

```
<212> TYPE: PRT
<213> ORGANISM: Epstein Barr Virus

<400> SEQUENCE: 87

Thr Tyr Ser Ala Gly Ile Val Gln Ile
1               5

<210> SEQ ID NO 88
<211> LENGTH: 11
<212> TYPE: PRT
<213> ORGANISM: Epstein Barr Virus

<400> SEQUENCE: 88

Arg Arg Ala Arg Ser Leu Ser Ala Glu Arg Tyr
1               5                   10

<210> SEQ ID NO 89
<211> LENGTH: 9
<212> TYPE: PRT
<213> ORGANISM: Epstein Barr Virus

<400> SEQUENCE: 89

Val Ser Phe Ile Glu Phe Val Gly Trp
1               5

<210> SEQ ID NO 90
<211> LENGTH: 10
<212> TYPE: PRT
<213> ORGANISM: Epstein Barr Virus

<400> SEQUENCE: 90

Ala Val Phe Asp Arg Lys Ser Asp Ala Lys
1               5                   10

<210> SEQ ID NO 91
<211> LENGTH: 9
<212> TYPE: PRT
<213> ORGANISM: Epstein Barr Virus

<400> SEQUENCE: 91

Ile Val Thr Asp Phe Ser Val Ile Lys
1               5

<210> SEQ ID NO 92
<211> LENGTH: 9
<212> TYPE: PRT
<213> ORGANISM: Epstein Barr Virus

<400> SEQUENCE: 92

Ala Val Leu Leu His Glu Glu Ser Met
1               5

<210> SEQ ID NO 93
<211> LENGTH: 10
<212> TYPE: PRT
<213> ORGANISM: Epstein Barr Virus

<400> SEQUENCE: 93

Val Glu Ile Thr Pro Tyr Lys Pro Thr Trp
1               5                   10

<210> SEQ ID NO 94
<211> LENGTH: 9
<212> TYPE: PRT
<213> ORGANISM: Epstein Barr Virus
```

<400> SEQUENCE: 94

Glu Gly Gly Val Gly Trp Arg His Trp
1               5

<210> SEQ ID NO 95
<211> LENGTH: 10
<212> TYPE: PRT
<213> ORGANISM: Epstein Barr Virus

<400> SEQUENCE: 95

Gln Asn Gly Ala Leu Ala Ile Asn Thr Phe
1               5                   10

<210> SEQ ID NO 96
<211> LENGTH: 10
<212> TYPE: PRT
<213> ORGANISM: Epstein Barr Virus

<400> SEQUENCE: 96

Leu Arg Gly Lys Trp Gln Arg Arg Tyr Arg
1               5                   10

<210> SEQ ID NO 97
<211> LENGTH: 9
<212> TYPE: PRT
<213> ORGANISM: Epstein Barr Virus

<400> SEQUENCE: 97

Arg Arg Ile Tyr Asp Leu Ile Glu Leu
1               5

<210> SEQ ID NO 98
<211> LENGTH: 8
<212> TYPE: PRT
<213> ORGANISM: Epstein Barr Virus

<400> SEQUENCE: 98

His His Ile Trp Gln Asn Leu Leu
1               5

<210> SEQ ID NO 99
<211> LENGTH: 10
<212> TYPE: PRT
<213> ORGANISM: Epstein Barr Virus

<400> SEQUENCE: 99

Glu Glu Asn Leu Leu Asp Phe Val Arg Phe
1               5                   10

<210> SEQ ID NO 100
<211> LENGTH: 10
<212> TYPE: PRT
<213> ORGANISM: Epstein Barr Virus

<400> SEQUENCE: 100

Leu Leu Asp Phe Val Arg Phe Met Gly Val
1               5                   10

<210> SEQ ID NO 101
<211> LENGTH: 9
<212> TYPE: PRT
<213> ORGANISM: Epstein Barr Virus

<400> SEQUENCE: 101

Leu Asp Phe Val Arg Phe Met Gly Val
1               5

<210> SEQ ID NO 102
<211> LENGTH: 9
<212> TYPE: PRT
<213> ORGANISM: Epstein Barr Virus

<400> SEQUENCE: 102

Lys Glu His Val Ile Gln Asn Ala Phe
1               5

<210> SEQ ID NO 103
<211> LENGTH: 9
<212> TYPE: PRT
<213> ORGANISM: Epstein Barr Virus

<400> SEQUENCE: 103

Phe Arg Lys Ala Gln Ile Gln Gly Leu
1               5

<210> SEQ ID NO 104
<211> LENGTH: 9
<212> TYPE: PRT
<213> ORGANISM: Epstein Barr Virus

<400> SEQUENCE: 104

Gln Pro Arg Ala Pro Ile Arg Pro Ile
1               5

<210> SEQ ID NO 105
<211> LENGTH: 9
<212> TYPE: PRT
<213> ORGANISM: Epstein Barr Virus

<400> SEQUENCE: 105

Ser Leu Arg Glu Trp Leu Leu Arg Ile
1               5

<210> SEQ ID NO 106
<211> LENGTH: 9
<212> TYPE: PRT
<213> ORGANISM: Epstein Barr Virus

<400> SEQUENCE: 106

Phe Trp Leu Tyr Ile Val Met Ser Asp
1               5

<210> SEQ ID NO 107
<211> LENGTH: 11
<212> TYPE: PRT
<213> ORGANISM: Epstein Barr Virus

<400> SEQUENCE: 107

Phe Arg Arg Asp Leu Leu Cys Pro Leu Gly Ala
1               5                   10

<210> SEQ ID NO 108
<211> LENGTH: 9
<212> TYPE: PRT
<213> ORGANISM: Epstein Barr Virus

<400> SEQUENCE: 108

Tyr Leu Leu Glu Met Leu Trp Arg Leu

```
<210> SEQ ID NO 109
<211> LENGTH: 9
<212> TYPE: PRT
<213> ORGANISM: Epstein Barr Virus

<400> SEQUENCE: 109

Tyr Leu Gln Gln Asn Trp Trp Thr Leu
1               5

<210> SEQ ID NO 110
<211> LENGTH: 9
<212> TYPE: PRT
<213> ORGANISM: Epstein Barr Virus

<400> SEQUENCE: 110

Thr Leu Leu Val Asp Leu Leu Trp Leu
1               5

<210> SEQ ID NO 111
<211> LENGTH: 12
<212> TYPE: PRT
<213> ORGANISM: Epstein Barr Virus

<400> SEQUENCE: 111

Asp Pro His Gly Pro Val Gln Leu Ser Tyr Tyr Asp
1               5                   10

<210> SEQ ID NO 112
<211> LENGTH: 9
<212> TYPE: PRT
<213> ORGANISM: Epstein Barr Virus

<400> SEQUENCE: 112

Met Gly Ser Leu Glu Met Val Pro Met
1               5

<210> SEQ ID NO 113
<211> LENGTH: 15
<212> TYPE: PRT
<213> ORGANISM: Epstein Barr Virus

<400> SEQUENCE: 113

Glu Asp Pro Tyr Trp Gly Asn Gly Asp Arg His Ser Asp Tyr Gln
1               5                   10                  15

<210> SEQ ID NO 114
<211> LENGTH: 14
<212> TYPE: PRT
<213> ORGANISM: Epstein Barr Virus

<400> SEQUENCE: 114

Asn Pro Val Cys Leu Pro Val Ile Val Ala Pro Tyr Leu Phe
1               5                   10

<210> SEQ ID NO 115
<211> LENGTH: 9
<212> TYPE: PRT
<213> ORGANISM: Epstein Barr Virus

<400> SEQUENCE: 115

Leu Pro Val Ile Val Ala Pro Tyr Leu
1               5
```

<210> SEQ ID NO 116
<211> LENGTH: 9
<212> TYPE: PRT
<213> ORGANISM: Epstein Barr Virus

<400> SEQUENCE: 116

Pro Tyr Leu Phe Trp Leu Ala Ala Ile
1               5

<210> SEQ ID NO 117
<211> LENGTH: 14
<212> TYPE: PRT
<213> ORGANISM: Epstein Barr Virus

<400> SEQUENCE: 117

Ala Ser Cys Phe Thr Ala Ser Val Ser Thr Val Val Thr Ala
1               5                   10

<210> SEQ ID NO 118
<211> LENGTH: 9
<212> TYPE: PRT
<213> ORGANISM: Epstein Barr Virus

<400> SEQUENCE: 118

Phe Thr Ala Ser Val Ser Thr Val Val
1               5

<210> SEQ ID NO 119
<211> LENGTH: 9
<212> TYPE: PRT
<213> ORGANISM: Epstein Barr Virus

<400> SEQUENCE: 119

Ile Glu Asp Pro Pro Phe Asn Ser Leu
1               5

<210> SEQ ID NO 120
<211> LENGTH: 9
<212> TYPE: PRT
<213> ORGANISM: Epstein Barr Virus

<400> SEQUENCE: 120

Arg Arg Arg Trp Arg Arg Leu Thr Val
1               5

<210> SEQ ID NO 121
<211> LENGTH: 9
<212> TYPE: PRT
<213> ORGANISM: Epstein Barr Virus

<400> SEQUENCE: 121

Arg Arg Trp Arg Arg Leu Thr Val Cys
1               5

<210> SEQ ID NO 122
<211> LENGTH: 11
<212> TYPE: PRT
<213> ORGANISM: Epstein Barr Virus

<400> SEQUENCE: 122

Arg Arg Leu Thr Val Cys Gly Gly Ile Met Phe
1               5                   10

<210> SEQ ID NO 123

```
<211> LENGTH: 9
<212> TYPE: PRT
<213> ORGANISM: Epstein Barr Virus

<400> SEQUENCE: 123

Thr Val Cys Gly Gly Ile Met Phe Leu
1               5

<210> SEQ ID NO 124
<211> LENGTH: 14
<212> TYPE: PRT
<213> ORGANISM: Epstein Barr Virus

<400> SEQUENCE: 124

Met Phe Leu Ala Cys Val Leu Val Leu Ile Val Asp Ala Val
1               5                   10

<210> SEQ ID NO 125
<211> LENGTH: 9
<212> TYPE: PRT
<213> ORGANISM: Epstein Barr Virus

<400> SEQUENCE: 125

Leu Ile Val Asp Ala Val Leu Gln Leu
1               5

<210> SEQ ID NO 126
<211> LENGTH: 9
<212> TYPE: PRT
<213> ORGANISM: Epstein Barr Virus

<400> SEQUENCE: 126

Gly Leu Gly Thr Leu Gly Ala Ala Ile
1               5

<210> SEQ ID NO 127
<211> LENGTH: 9
<212> TYPE: PRT
<213> ORGANISM: Epstein Barr Virus

<400> SEQUENCE: 127

Leu Leu Trp Thr Leu Val Val Leu Leu
1               5

<210> SEQ ID NO 128
<211> LENGTH: 11
<212> TYPE: PRT
<213> ORGANISM: Epstein Barr Virus

<400> SEQUENCE: 128

Ser Ser Cys Ser Ser Cys Pro Leu Ser Lys Ile
1               5                   10

<210> SEQ ID NO 129
<211> LENGTH: 9
<212> TYPE: PRT
<213> ORGANISM: Epstein Barr Virus

<400> SEQUENCE: 129

Ile Leu Leu Ala Arg Leu Phe Leu Tyr
1               5

<210> SEQ ID NO 130
<211> LENGTH: 9
<212> TYPE: PRT
```

<213> ORGANISM: Epstein Barr Virus

<400> SEQUENCE: 130

Phe Leu Tyr Ala Leu Ala Leu Leu Leu
1               5

<210> SEQ ID NO 131
<211> LENGTH: 9
<212> TYPE: PRT
<213> ORGANISM: Epstein Barr Virus

<400> SEQUENCE: 131

Thr Tyr Gly Pro Val Phe Met Cys Leu
1               5

<210> SEQ ID NO 132
<211> LENGTH: 9
<212> TYPE: PRT
<213> ORGANISM: Epstein Barr Virus

<400> SEQUENCE: 132

Cys Leu Gly Gly Leu Leu Thr Met Val
1               5

<210> SEQ ID NO 133
<211> LENGTH: 10
<212> TYPE: PRT
<213> ORGANISM: Epstein Barr Virus

<400> SEQUENCE: 133

Val Met Ser Asn Thr Leu Leu Ser Ala Trp
1               5                   10

<210> SEQ ID NO 134
<211> LENGTH: 9
<212> TYPE: PRT
<213> ORGANISM: Epstein Barr Virus

<400> SEQUENCE: 134

Leu Thr Ala Gly Phe Leu Ile Phe Leu
1               5

<210> SEQ ID NO 135
<211> LENGTH: 9
<212> TYPE: PRT
<213> ORGANISM: Epstein Barr Virus

<400> SEQUENCE: 135

Leu Leu Ser Ala Trp Ile Leu Thr Ala
1               5

<210> SEQ ID NO 136
<211> LENGTH: 14
<212> TYPE: PRT
<213> ORGANISM: Epstein Barr Virus

<400> SEQUENCE: 136

Leu Val Ser Asp Tyr Cys Asn Val Leu Asn Lys Glu Phe Thr
1               5                   10

<210> SEQ ID NO 137
<211> LENGTH: 9
<212> TYPE: PRT
<213> ORGANISM: Epstein Barr Virus

<400> SEQUENCE: 137

Leu Val Ser Asp Tyr Cys Asn Val Leu
1               5

<210> SEQ ID NO 138
<211> LENGTH: 10
<212> TYPE: PRT
<213> ORGANISM: Epstein Barr Virus

<400> SEQUENCE: 138

Asp Tyr Cys Asn Val Leu Asn Lys Glu Phe
1               5                   10

<210> SEQ ID NO 139
<211> LENGTH: 9
<212> TYPE: PRT
<213> ORGANISM: Epstein Barr Virus

<400> SEQUENCE: 139

Ala Glu Asn Ala Gly Asn Asp Ala Cys
1               5

<210> SEQ ID NO 140
<211> LENGTH: 16
<212> TYPE: PRT
<213> ORGANISM: Epstein Barr Virus

<400> SEQUENCE: 140

Ile Ala Cys Pro Ile Val Met Arg Tyr Tyr Val Leu Asp His Leu Ile
1               5                   10                  15

<210> SEQ ID NO 141
<211> LENGTH: 9
<212> TYPE: PRT
<213> ORGANISM: Epstein Barr Virus

<400> SEQUENCE: 141

Tyr Val Leu Asp His Leu Ile Val Val
1               5

<210> SEQ ID NO 142
<211> LENGTH: 15
<212> TYPE: PRT
<213> ORGANISM: Epstein Barr Virus

<400> SEQUENCE: 142

Phe Phe Ile Gln Ala Pro Ser Asn Arg Val Met Ile Pro Ala Thr
1               5                   10                  15

<210> SEQ ID NO 143
<211> LENGTH: 9
<212> TYPE: PRT
<213> ORGANISM: Epstein Barr Virus

<400> SEQUENCE: 143

Ala Thr Ile Gly Thr Ala Met Tyr Lys
1               5

<210> SEQ ID NO 144
<211> LENGTH: 15
<212> TYPE: PRT
<213> ORGANISM: Epstein Barr Virus

<400> SEQUENCE: 144

Lys His Ser Arg Val Arg Ala Tyr Thr Tyr Ser Lys Val Leu Gly
1               5                   10                  15

<210> SEQ ID NO 145
<211> LENGTH: 15
<212> TYPE: PRT
<213> ORGANISM: Epstein Barr Virus

<400> SEQUENCE: 145

Arg Ala Leu Ile Lys Thr Leu Pro Arg Ala Ser Tyr Ser Ser His
1               5                   10                  15

<210> SEQ ID NO 146
<211> LENGTH: 15
<212> TYPE: PRT
<213> ORGANISM: Epstein Barr Virus

<400> SEQUENCE: 146

Glu Arg Pro Ile Phe Pro His Pro Ser Lys Pro Thr Phe Leu Pro
1               5                   10                  15

<210> SEQ ID NO 147
<211> LENGTH: 14
<212> TYPE: PRT
<213> ORGANISM: Epstein Barr Virus

<400> SEQUENCE: 147

Gln Lys Glu Glu Ala Ala Ile Cys Gly Gln Met Asp Leu Ser
1               5                   10

<210> SEQ ID NO 148
<211> LENGTH: 15
<212> TYPE: PRT
<213> ORGANISM: Epstein Barr Virus

<400> SEQUENCE: 148

Glu Val Cys Gln Pro Lys Arg Ile Arg Pro Phe His Pro Pro Gly
1               5                   10                  15

<210> SEQ ID NO 149
<211> LENGTH: 13
<212> TYPE: PRT
<213> ORGANISM: Epstein Barr Virus

<400> SEQUENCE: 149

Leu Pro Glu Pro Leu Pro Gln Gly Gln Leu Thr Ala Tyr
1               5                   10

<210> SEQ ID NO 150
<211> LENGTH: 11
<212> TYPE: PRT
<213> ORGANISM: Epstein Barr Virus

<400> SEQUENCE: 150

Glu Pro Leu Pro Gln Gly Gln Leu Thr Ala Tyr
1               5                   10

<210> SEQ ID NO 151
<211> LENGTH: 9
<212> TYPE: PRT
<213> ORGANISM: Epstein Barr Virus

<400> SEQUENCE: 151

Ala Pro Glu Asn Ala Tyr Gln Ala Tyr
1               5

<210> SEQ ID NO 152
<211> LENGTH: 9
<212> TYPE: PRT
<213> ORGANISM: Epstein Barr Virus

<400> SEQUENCE: 152

Leu Gln His Tyr Arg Glu Val Ala Ala
1               5

<210> SEQ ID NO 153
<211> LENGTH: 12
<212> TYPE: PRT
<213> ORGANISM: Epstein Barr Virus

<400> SEQUENCE: 153

Asp Ser Glu Leu Glu Ile Lys Arg Tyr Lys Asn Arg
1               5                   10

<210> SEQ ID NO 154
<211> LENGTH: 16
<212> TYPE: PRT
<213> ORGANISM: Epstein Barr Virus

<400> SEQUENCE: 154

Arg Lys Cys Cys Arg Ala Lys Phe Lys Gln Leu Leu Gln His Tyr Arg
1               5                   10                  15

<210> SEQ ID NO 155
<211> LENGTH: 8
<212> TYPE: PRT
<213> ORGANISM: Epstein Barr Virus

<400> SEQUENCE: 155

Arg Ala Lys Phe Lys Gln Leu Leu
1               5

<210> SEQ ID NO 156
<211> LENGTH: 9
<212> TYPE: PRT
<213> ORGANISM: Epstein Barr Virus

<400> SEQUENCE: 156

Ser Glu Asn Asp Arg Leu Arg Leu Leu
1               5

<210> SEQ ID NO 157
<211> LENGTH: 9
<212> TYPE: PRT
<213> ORGANISM: Influenza A Virus

<400> SEQUENCE: 157

Cys Thr Glu Leu Lys Leu Ser Asp Tyr
1               5

<210> SEQ ID NO 158
<211> LENGTH: 9
<212> TYPE: PRT
<213> ORGANISM: Influenza A Virus

<400> SEQUENCE: 158

Val Ser Asp Gly Gly Pro Asn Leu Tyr
1               5

<210> SEQ ID NO 159
<211> LENGTH: 9
<212> TYPE: PRT
<213> ORGANISM: Influenza A Virus

<400> SEQUENCE: 159

Gly Ile Leu Gly Phe Val Phe Thr Leu
1               5

<210> SEQ ID NO 160
<211> LENGTH: 10
<212> TYPE: PRT
<213> ORGANISM: Influenza A Virus

<400> SEQUENCE: 160

Ile Leu Gly Phe Val Phe Thr Leu Thr Val
1               5                   10

<210> SEQ ID NO 161
<211> LENGTH: 9
<212> TYPE: PRT
<213> ORGANISM: Influenza A Virus

<400> SEQUENCE: 161

Ile Leu Arg Gly Ser Val Ala His Lys
1               5

<210> SEQ ID NO 162
<211> LENGTH: 9
<212> TYPE: PRT
<213> ORGANISM: Influenza A Virus

<400> SEQUENCE: 162

Ser Ile Ile Pro Ser Gly Pro Leu Lys
1               5

<210> SEQ ID NO 163
<211> LENGTH: 10
<212> TYPE: PRT
<213> ORGANISM: Influenza A Virus

<400> SEQUENCE: 163

Arg Met Val Leu Ala Ser Thr Thr Ala Lys
1               5                   10

<210> SEQ ID NO 164
<211> LENGTH: 9
<212> TYPE: PRT
<213> ORGANISM: Influenza A Virus

<400> SEQUENCE: 164

Lys Ser Met Arg Glu Glu Tyr Arg Lys
1               5

<210> SEQ ID NO 165
<211> LENGTH: 9
<212> TYPE: PRT
<213> ORGANISM: Influenza A Virus

<400> SEQUENCE: 165

Ser Pro Ile Val Pro Ser Phe Asp Met
1               5

<210> SEQ ID NO 166
<211> LENGTH: 9

<212> TYPE: PRT
<213> ORGANISM: Influenza A Virus

<400> SEQUENCE: 166

Gln Pro Glu Trp Phe Arg Asn Val Leu
1 5

<210> SEQ ID NO 167
<211> LENGTH: 9
<212> TYPE: PRT
<213> ORGANISM: Influenza A Virus

<400> SEQUENCE: 167

Ser Arg Tyr Trp Ala Ile Arg Thr Arg
1 5

<210> SEQ ID NO 168
<211> LENGTH: 16
<212> TYPE: PRT
<213> ORGANISM: Artificial Sequence
<220> FEATURE:
<223> OTHER INFORMATION: Stem for branched peptide
<220> FEATURE:
<221> NAME/KEY: MISC_FEATURE
<222> LOCATION: (1)..(16)
<223> OTHER INFORMATION: X = Azidonorleucine

<400> SEQUENCE: 168

Ser Glu Glu Xaa Ser Glu Glu Xaa Ser Glu Glu Xaa Ser Glu Glu Xaa
1 5 10 15

<210> SEQ ID NO 169
<211> LENGTH: 19
<212> TYPE: PRT
<213> ORGANISM: Artificial Sequence
<220> FEATURE:
<223> OTHER INFORMATION: Branch 1-1 for branched peptide
<220> FEATURE:
<221> NAME/KEY: MISC_FEATURE
<222> LOCATION: (1)..(19)
<223> OTHER INFORMATION: X = propargyl glycine

<400> SEQUENCE: 169

Xaa Lys Pro Ala Lys Phe Phe Arg Leu Thr Pro Arg Val Thr Gly Gly
1 5 10 15

Gly Ala Met

<210> SEQ ID NO 170
<211> LENGTH: 20
<212> TYPE: PRT
<213> ORGANISM: Artificial Sequence
<220> FEATURE:
<223> OTHER INFORMATION: Branch 1-2 for branched peptide
<220> FEATURE:
<221> NAME/KEY: MISC_FEATURE
<222> LOCATION: (1)..(20)
<223> OTHER INFORMATION: X = propargyl glycine

<400> SEQUENCE: 170

Xaa Lys Pro Ala Lys Phe Phe Arg Leu Arg Pro His Glu Arg Asn Gly
1 5 10 15

Phe Thr Val Leu
20

<210> SEQ ID NO 171
<211> LENGTH: 19
<212> TYPE: PRT

```
<213> ORGANISM: Artificial Sequence
<220> FEATURE:
<223> OTHER INFORMATION: Branch 1-3 for branched peptide
<220> FEATURE:
<221> NAME/KEY: MISC_FEATURE
<222> LOCATION: (1)..(19)
<223> OTHER INFORMATION: X = propargyl glycine

<400> SEQUENCE: 171

Xaa Lys Pro Ala Lys Phe Phe Arg Leu Arg Glu Leu Arg Arg Lys Met
1               5                   10                  15

Met Tyr Met

<210> SEQ ID NO 172
<211> LENGTH: 18
<212> TYPE: PRT
<213> ORGANISM: Artificial Sequence
<220> FEATURE:
<223> OTHER INFORMATION: Branch 1-4 for branched peptide
<220> FEATURE:
<221> NAME/KEY: MISC_FEATURE
<222> LOCATION: (1)..(18)
<223> OTHER INFORMATION: X = propargyl glycine

<400> SEQUENCE: 172

Xaa Lys Pro Ala Lys Phe Phe Arg Leu Asn Leu Val Pro Met Val Ala
1               5                   10                  15

Thr Val

<210> SEQ ID NO 173
<211> LENGTH: 18
<212> TYPE: PRT
<213> ORGANISM: Artificial Sequence
<220> FEATURE:
<223> OTHER INFORMATION: Branch 3-1 for branched peptide
<220> FEATURE:
<221> NAME/KEY: MISC_FEATURE
<222> LOCATION: (1)..(18)
<223> OTHER INFORMATION: X = propargyl glycine

<400> SEQUENCE: 173

Xaa Ala Ile Pro Val Ser Leu Arg Thr Pro Arg Val Thr Gly Gly Gly
1               5                   10                  15

Ala Met

<210> SEQ ID NO 174
<211> LENGTH: 19
<212> TYPE: PRT
<213> ORGANISM: Artificial Sequence
<220> FEATURE:
<223> OTHER INFORMATION: Branch 3-2 for branched peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 174

Xaa Ala Ile Pro Val Ser Leu Arg Arg Pro His Glu Arg Asn Gly Phe
1               5                   10                  15

Thr Val Leu

<210> SEQ ID NO 175
<211> LENGTH: 17
<212> TYPE: PRT
<213> ORGANISM: Artificial Sequence
<220> FEATURE:
<223> OTHER INFORMATION: Branch 3-3 for branched peptide
```

```
<220> FEATURE:
<221> NAME/KEY: MISC_FEATURE
<222> LOCATION: (1)..(17)
<223> OTHER INFORMATION: X = propargyl glycine

<400> SEQUENCE: 175

Xaa Ala Ile Pro Val Ser Leu Arg Glu Leu Arg Arg Lys Met Met Tyr
1               5                   10                  15

Met

<210> SEQ ID NO 176
<211> LENGTH: 16
<212> TYPE: PRT
<213> ORGANISM: Artificial Sequence
<220> FEATURE:
<223> OTHER INFORMATION: Branch 3-4 for branched peptide
<220> FEATURE:
<221> NAME/KEY: MISC_FEATURE
<222> LOCATION: (1)..(16)
<223> OTHER INFORMATION: X = propargyl glycine

<400> SEQUENCE: 176

Xaa Ala Ile Pro Val Ser Leu Val Thr Glu His Asp Thr Leu Leu Tyr
1               5                   10                  15

<210> SEQ ID NO 177
<211> LENGTH: 8
<212> TYPE: PRT
<213> ORGANISM: Artificial Sequence
<220> FEATURE:
<223> OTHER INFORMATION: C1s cleavage site

<400> SEQUENCE: 177

Tyr Leu Gly Arg Ser Tyr Lys Val
1               5

<210> SEQ ID NO 178
<211> LENGTH: 6
<212> TYPE: PRT
<213> ORGANISM: Artificial Sequence
<220> FEATURE:
<223> OTHER INFORMATION: C1s cleavage site
<220> FEATURE:
<221> NAME/KEY: misc_feature
<222> LOCATION: (6)..(6)
<223> OTHER INFORMATION: Xaa can be any naturally occurring amino acid

<400> SEQUENCE: 178

Met Gln Leu Gly Arg Xaa
1               5

<210> SEQ ID NO 179
<211> LENGTH: 8
<212> TYPE: PRT
<213> ORGANISM: Artificial Sequence
<220> FEATURE:
<223> OTHER INFORMATION: MASP2 cleavage site

<400> SEQUENCE: 179

Ser Leu Gly Arg Lys Ile Gln Ile
1               5

<210> SEQ ID NO 180
<211> LENGTH: 9
<212> TYPE: PRT
<213> ORGANISM: Artificial Sequence
<220> FEATURE:
<223> OTHER INFORMATION: C2a cleavage site
```

<400> SEQUENCE: 180

Gly Leu Ala Arg Ser Asn Leu Asp Glu
1               5

<210> SEQ ID NO 181
<211> LENGTH: 9
<212> TYPE: PRT
<213> ORGANISM: Artificial Sequence
<220> FEATURE:
<223> OTHER INFORMATION: Cathepsin D cleavage site

<400> SEQUENCE: 181

Pro Arg Ser Phe Phe Arg Leu Gly Lys
1               5

<210> SEQ ID NO 182
<211> LENGTH: 8
<212> TYPE: PRT
<213> ORGANISM: Artificial Sequence
<220> FEATURE:
<223> OTHER INFORMATION: ADAM28 cleavage site

<400> SEQUENCE: 182

Lys Pro Ala Lys Phe Phe Arg Leu
1               5

<210> SEQ ID NO 183
<211> LENGTH: 8
<212> TYPE: PRT
<213> ORGANISM: Artificial Sequence
<220> FEATURE:
<223> OTHER INFORMATION: ADAM28 cleavage site

<400> SEQUENCE: 183

Asp Pro Ala Lys Phe Phe Arg Leu
1               5

<210> SEQ ID NO 184
<211> LENGTH: 8
<212> TYPE: PRT
<213> ORGANISM: Artificial Sequence
<220> FEATURE:
<223> OTHER INFORMATION: ADAM28 cleavage site

<400> SEQUENCE: 184

Lys Pro Met Lys Phe Phe Arg Leu
1               5

<210> SEQ ID NO 185
<211> LENGTH: 8
<212> TYPE: PRT
<213> ORGANISM: Artificial Sequence
<220> FEATURE:
<223> OTHER INFORMATION: ADAM28 cleavage site

<400> SEQUENCE: 185

Leu Pro Ala Lys Phe Phe Arg Leu
1               5

<210> SEQ ID NO 186
<211> LENGTH: 7
<212> TYPE: PRT
<213> ORGANISM: Artificial Sequence
<220> FEATURE:
<223> OTHER INFORMATION: MMP2 cleavage site

```
<400> SEQUENCE: 186

Ala Ile Pro Val Ser Leu Arg
1               5

<210> SEQ ID NO 187
<211> LENGTH: 220
<212> TYPE: PRT
<213> ORGANISM: Artificial Sequence
<220> FEATURE:
<223> OTHER INFORMATION: Bundled domain sequence

<400> SEQUENCE: 187

Ser Ala Ser Gly Gly Ser Gly Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Asp Ala Pro Ala Val Gly Gly Gly Ser Gly Gly Gly Ser
            35                  40                  45

Thr Ile Pro Val Ser Leu Arg Ser Thr Pro Arg Val Thr Gly Gly
            50                  55                  60

Ala Met Thr Ile Pro Val Ser Leu Arg Ser Gly Gly Gly Ser Gly
65                  70                  75                  80

Gly Gly Ser Thr Val Arg Tyr Tyr Arg Ile Thr Tyr Gly Glu Thr
                85                  90                  95

Gly Gly Asn Ser Pro Val Gln Glu Phe Thr Val Pro Gly Ser Lys Ser
                100                 105                 110

Thr Ala Thr Ile Ser Gly Leu Lys Pro Gly Val Asp Tyr Thr Ile Thr
            115                 120                 125

Val Tyr Ala Val Thr Gly Gly Gly Gly Ser Gly Gly Gly Ser
        130                 135                 140

Thr Ile Pro Val Ser Leu Arg Ser Asn Leu Val Pro Met Val Ala Thr
145                 150                 155                 160

Val Thr Ile Pro Val Ser Leu Arg Ser Gly Gly Gly Ser Gly Gly
                165                 170                 175

Gly Gly Ser Ser Pro Ala Ser Ser Lys Pro Ile Ser Ile Asn Tyr Arg
            180                 185                 190

Thr Gly Gly Gly Gly Ser Gly Gly Gly Ser Thr Ile Pro Val Ser
            195                 200                 205

Leu Arg Ser Val Leu Glu Glu Thr Ser Val Met Leu
        210                 215                 220

<210> SEQ ID NO 188
<211> LENGTH: 8
<212> TYPE: PRT
<213> ORGANISM: Artificial Sequence
<220> FEATURE:
<223> OTHER INFORMATION: MMP2 cleavage site

<400> SEQUENCE: 188

Thr Ile Pro Val Ser Leu Arg Ser
1               5
```